US012747209B2

(12) United States Patent
Liu et al.

(10) Patent No.: US 12,747,209 B2
(45) Date of Patent: Sep. 29, 2026

(54) SUBSTITUTED DIARYL COMPOUND AS WELL AS PREPARATION METHOD AND APPLICATION THEREOF

(71) Applicant: SHANDONG FIRST MEDICAL UNIV & SHANDONG ACADEMY OF MEDICAL SCIENCES, Jinan City (CN)

(72) Inventors: Bo Liu, Jinan City (CN); Qingqiang Yao, Jinan City (CN); Haijiao Chen, Jinan City (CN); Xinmei Yang, Jinan City (CN); Ying Zhi, Jinan City (CN); Ying Li, Jinan City (CN); Haiyang Wang, Jinan City (CN); Zhengguo Cui, Jinan City (CN); Xiaoxiang Liu, Jinan City (CN); Guodong Hu, Jinan City (CN); Tiandi Ding, Jinan City (CN); Feipeng Zhang, Jinan City (CN)

(73) Assignee: SHANDONG FIRST MEDICAL. UNIV & SHANDONG ACADEMY OF MEDICAL SCIENCES, Jinan City (CN)

( * ) Notice: Subject to any disclaimer, the term of this patent is extended or adjusted under 35 U.S.C. 154(b) by 368 days.

(21) Appl. No.: 18/540,293

(22) Filed: Dec. 14, 2023

(65) Prior Publication Data

US 2024/0166602 A1 May 23, 2024

Related U.S. Application Data

(63) Continuation of application No. PCT/CN2022/082764, filed on Mar. 24, 2022.

(30) Foreign Application Priority Data

Jun. 15, 2021 (CN) ........................ 202110658765.4

(51) Int. Cl.

| | |
|---|---|
| ***C07D 211/14*** | (2006.01) |
| ***A61P 35/00*** | (2006.01) |
| ***C07C 217/64*** | (2006.01) |
| ***C07D 207/06*** | (2006.01) |
| ***C07D 211/82*** | (2006.01) |

(52) U.S. Cl.
CPC ............ *C07D 211/14* (2013.01); *A61P 35/00* (2018.01); *C07C 217/64* (2013.01); *C07D 207/06* (2013.01); *C07D 211/82* (2013.01)

(58) Field of Classification Search
CPC .................................................. C07D 211/14
See application file for complete search history.

(56) References Cited

FOREIGN PATENT DOCUMENTS

JP 2017193527 A * 10/2017

* cited by examiner

*Primary Examiner* — Andrew D Kosar
*Assistant Examiner* — Connor K English
(74) *Attorney, Agent, or Firm* — JEEN IP LAW, LLC

(57) ABSTRACT

The invention relates to the field of medicinal chemistry, in particular to a substituted diaryl compound shown as a formula (I), a preparation method of the substituted diaryl compound, a medicinal preparation containing the substituted diaryl compound and medical application of the substituted diaryl compound. Pharmacological test results show that the substituted diaryl compound disclosed by the invention has a good inhibition effect on cells of human lung cancer (A549), human ovarian cancer (SKOV3), human melanoma (A375) and human colon cancer (LOVO). The formula (I) is shown in the specification.

Formula (I)

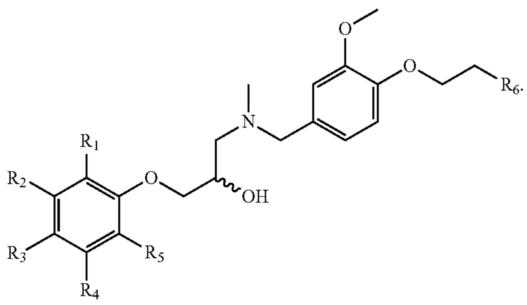

6 Claims, No Drawings

SUBSTITUTED DIARYL COMPOUND AS WELL AS PREPARATION METHOD AND APPLICATION THEREOF

TECHNICAL FIELD

The present invention relates to the field of medicinal chemistry, specifically to a type of substituted diaryl compounds, their preparation methods, their pharmaceutical preparations and their medicinal uses.

BACKGROUND 1-(2-ethoxyphenoxy)-3-(3-methoxy-4-(2-(4-methylpiperidin-1-yl)ethoxy)benxyl)(methyl)amino)propan-2-ol, CAS No: 2125657-10-3, molecular formula $C_{28}H_{42}N_2O_5$, structural formula:

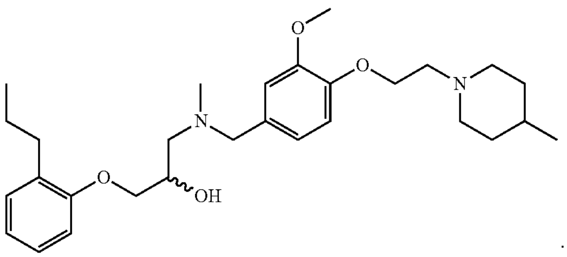 [SMILES: CCCc1ccccc1OCC(O)CN(C)Cc1ccc(OCCN2CCC(C)CC2)c(OC)c1]

.

The currently published literature only contains the physical and chemical properties of this compound, and there is no disclosure of its pharmacological effects, let alone any literature reports on its anti-tumor effects.

SUMMARY

The technical problem solved by the present invention is to provide a type of substituted diaryl compounds and pharmaceutically acceptable salts thereof, their optical isomers, their preparation methods, pharmaceutical compositions and their application in the preparation of drugs for treating cancer.

In order to solve the technical problems of the present invention, the present invention provides the following technical solutions.

The first aspect of the technical solution of the present invention is to provide a compound of general formula (I) or a pharmaceutically acceptable salt thereof, or an optical isomer thereof:

Formula (I)

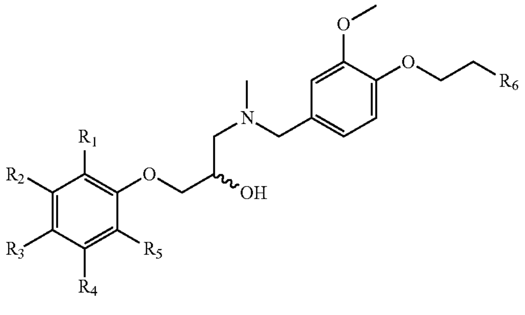

wherein, $R_1$ represents $-OC_2H_5$, $-H$, $-CH(CH_3)_2$, $-Br$, $-CF_3$, $-OCH_3$, $-F$, $-Cl$, or $-CH_3$;

$R_2$ represents $-F$, $-CF_3$, $-Br$, $-NHCOCH_3$, $-Cl$, $-H$, $-OCH_3$, or $-CH(CH_3)_2$;

$R_3$ represents $-H$, $-CH_3$, $-Cl$, $-Br$, $-NHCOCH_3$, $-C_3H_7$, $-F$, $-C_{14}H_{29}$, or $-OCH_3$;

$R_4$ represents $-H$, $-Br$, $-CF_3$, or $-Cl$;

$R_5$ represents $-H$, $-Cl$, $-I$, or $-Br$; $R_6$ represents

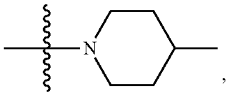
,
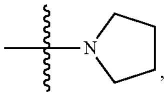
,
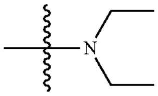
, or
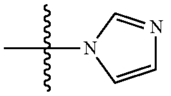
.

Preferably, the above-mentioned compound or its pharmaceutically acceptable salt or its optical isomer, $R_1$ represents $-H$, $-CH(CH_3)_2$, $-Br$, or $-Cl$;

$R_2$ represents $-F$, $-Br$, $-Cl$, $-H$, $-CH(CH_3)_2$, or $-CF_3$;

$R_3$ represents $-H$, $-CH_3$, $-Cl$, $-Br$, or $-C_{14}H_{29}$;

$R_4$ represents $-H$, $-Br$, $-CF_3$, or $-Cl$;

$R_5$ represents $-H$, $-Cl$, $-I$, or $-Br$;

$R_6$ represent:

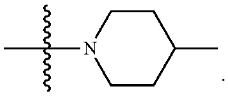 [SMILES: *N1CCC(C)CC1]
.

More preferably, the above-mentioned compound or its pharmaceutically acceptable salt or its optical isomer, $R_1$ represents $-H$; $R_2$ represents $-CF_3$; $R_3$ represents $-Br$; $R_4$ represents $-H$; $R_5$ represents $-H$; $R_6$ represents

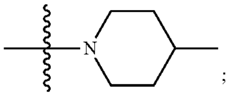 [SMILES: *N1CCC(C)CC1]
;

or $R_1$ represents $-H$; $R_2$ represents $-H$; $R_3$ represents $-C_{14}H_{29}$; $R_4$ represents $-H$; $R_5$ represents $-H$; $R_6$ represents

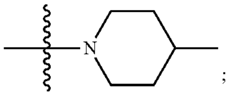 [SMILES: *N1CCC(C)CC1]
;

or $R_1$ represents $-H$; $R_2$ represents $-H$; $R_3$ represents $-Cl$; $R_4$ represents $-Br$; $R_5$ represents $-H$; $R_6$ represents

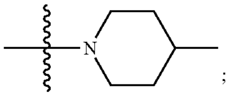
;

or $R_1$ represents —Br; $R_2$ represents —H; $R_3$ represents —Br; $R_4$ represents —H; $R_5$ represents —Br; $R_6$ represents

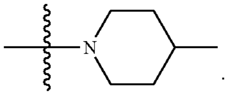 [SMILES: *N1CCC(C)CC1].

More preferably, the above-mentioned compound or its pharmaceutically acceptable salt or its optical isomer, $R_1$ represents —H; $R_2$ represents —$CF_3$; $R_3$ represents —Br; $R_4$ represents —H; $R_5$ represents —H; $R_6$ represents

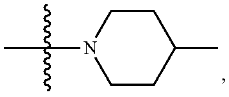 [SMILES: *N1CCC(C)CC1], or $R_1$ represents —H; $R_2$ represents —H; $R_3$ represents —$C_{14}H_{29}$; $R_4$ represents —H; $R_5$ represents —H; $R_6$ represents

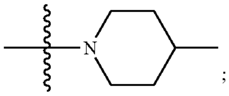;

or $R_1$ represents —Br; $R_2$ represents —H; $R_3$ represents —Br; $R_4$ represents —H; $R_5$ represents —Br; $R_6$ represents

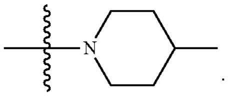 [SMILES: *N1CCC(C)CC1].

More preferably, the above-mentioned compound or its pharmaceutically acceptable salt or its optical isomer, $R_1$ represents —H; $R_2$ represents —$CF_3$; $R_3$ represents —Br; $R_4$ represents —H; $R_5$ represents —H; $R_6$ represents

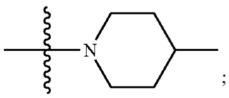;

or $R_1$ represents —Br; $R_2$ represents —H; $R_3$ represents —Br; $R_4$ represents —H; $R_5$ represents —Br; $R_6$ represents

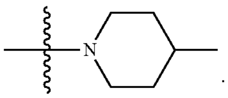 [SMILES: *N1CCC(C)CC1].

Pharmaceutically acceptable salts of any of the above compounds of the present invention include salt of organic acid, salt of inorganic acid, salt of organic alkali or salt of inorganic alkali. The organic acid includes acetic acid, trifluoroacetic acid, methylsulfonic acid, toluenesulfonic acid, maleic acid, succinic acid, tartaric acid, citric acid, fumaric acid; the inorganic acid includes hydrochloric acid, hydrobromic acid, nitric acid, sulfuric acid, phosphoric acid; the organic alkali includes meglumine, glucosamine; the inorganic alkali includes the alkaline compounds of sodium, potassium, barium, calcium, magnesium, zinc, and lithium.

Any of the above compounds in the invention is racemes or its optical isomer is its levoisomer or dextroisomer.

The second aspect of the technical solution of the present invention is to provide a preparation method for the compound described in the first aspect. The compound of general formula (I) of the present invention can be prepared by the following method:

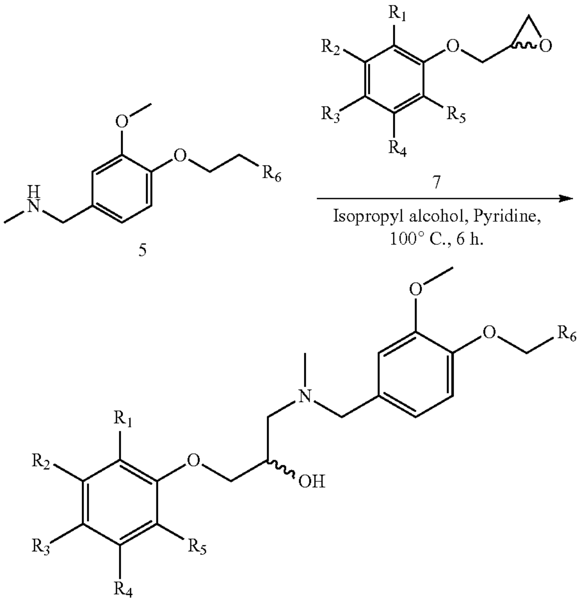

wherein, $R_1$ represents —$OC_2H_5$, —H, —$CH(CH_3)_2$, —Br, —$CF_3$, —$OCH_3$, —F, —Cl, or —$CH_3$;

$R_2$ represents —F, —$CF_3$, —Br, —$NHCOCH_3$, —$C_1$, —H, —$OCH_3$, or —$CH(CH_3)_2$;

$R_3$ represents —H, —$CH_3$, —Cl, —Br, —$NHCOCH_3$, —$C_3H_7$, —F, —$C_{14}H_{29}$, or —$OCH_3$;

$R_4$ represents —H, —Br, —$CF_3$, or —Cl;

$R_5$ represents —H, —Cl, —I, or —Br;

$R_6$ represents

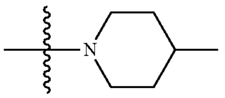, 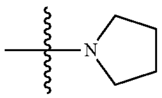, 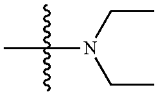, or 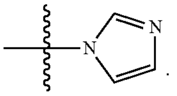.

Synthesis of the series of compounds of general formula (I): dissolve substituted phenoxymethyloxirane (7) (1.0 mmol) and compound (5) (1.2 mmol) in isopropanol (15 mL) under nitrogen protection, add a catalytic amount of pyridine, heat to reflux for 6 hours, and detect the disappearance of the raw material by TLC. The reaction solution was diluted with ethyl acetate, and the organic phase was washed with water and saturated brine in sequence, dried over anhydrous sodium sulfate, filtered, and the solvent was evaporated under reduced pressure. The crude product was separated and purified by silica gel column chromatography (mobile phase: dichloromethane-methanol=20:1) to obtain target compound (I) with a yield of 80%-90%.

The fourth aspect of the technical solution of the present invention provides the application of the compounds described in the first aspect and the pharmaceutical composition described in the third aspect to the preparation of a drug for treating cancer. The described cancer is lung cancer or ovarian cancer or melanoma or colon cancer.

The clinical method of administration of compound de scribed in the invention can be oral administration, injection, etc. The clinical dosage of the compound of the present invention is 0.01-1000 mg/day, and may deviate from this range depending on the severity of the disease or the dosage form.

Beneficial technical effects: The present invention provides a series of compounds with novel structures and anti-cancer effects, which compounds are effective against lung cancer, ovarian cancer, melanoma or colon cancer.

DETAILED DESCRIPTION OF EMBODIMENTS

The following specific embodiments will further illustrate the present invention so that those skilled in the art can better understand the present invention, but do not limit the present invention in this way.

Synthesis of the target compound in the embodiment of present invention: Dissolve substituted phenoxymethyloxirane (7) (1.0 mmol) and compound. (5) (1.2 mmol) in isopropanol (15 mL) under nitrogen protection, add a catalytic amount of pyridine, heat to reflux for 6 hours, and detect the disappearance of the raw material by TIC. The reaction solution was diluted with ethyl acetate, and the organic phase was washed with water and saturated brine in sequence, dried over anhydrous sodium sulfate, filtered, and the solvent was evaporated under reduced pressure. The crude product was separated and purified by silica gel column chromatography (mobile phase: dichloromethane-methanol=20:1) to obtain target compound.

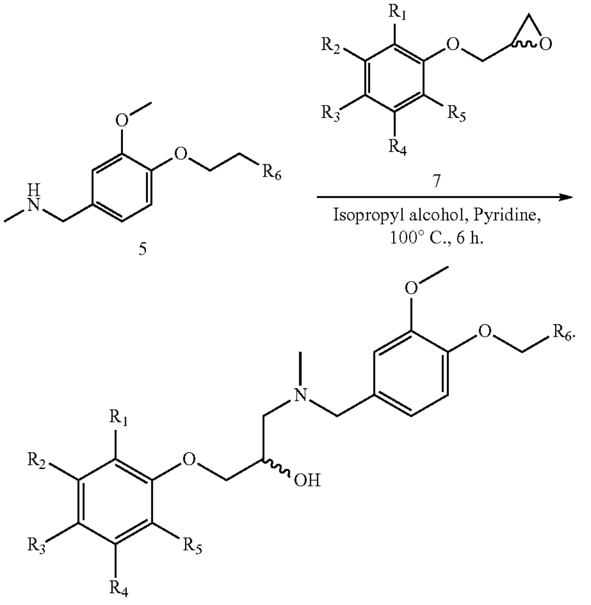

Compound (5) is synthesized through 4 steps of reaction using vanilline (1) as the raw material.

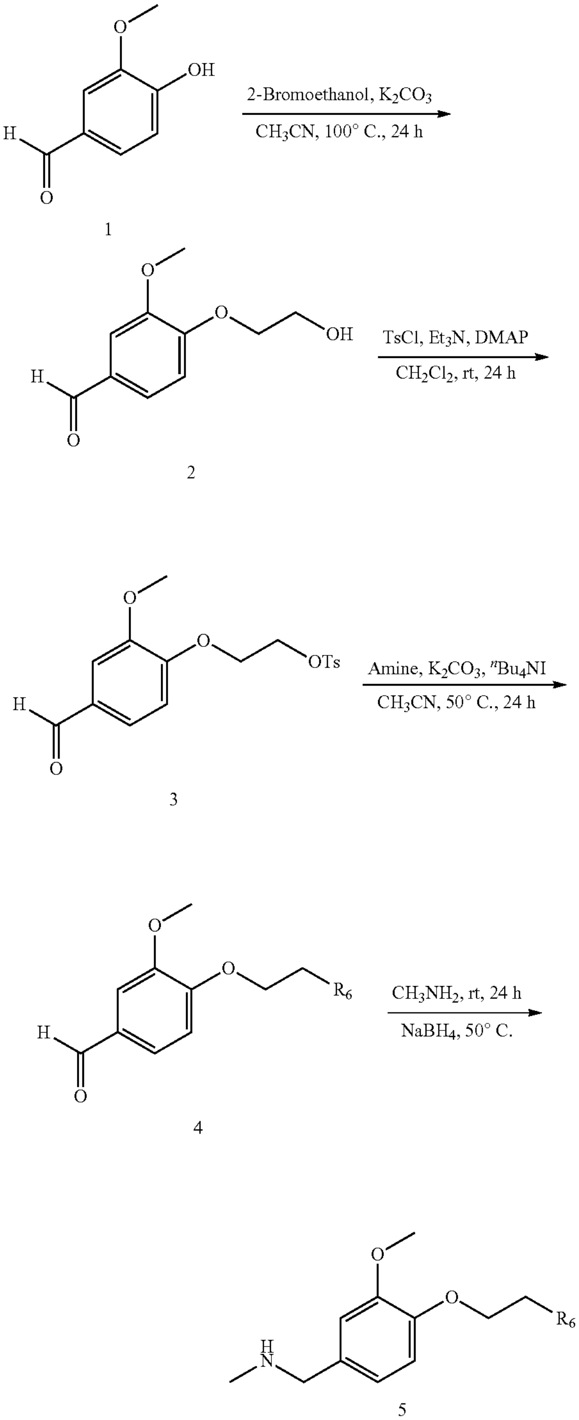

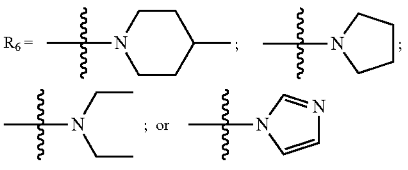

The 4 types of compound (5) obtained is shown in the following table:

TABLE 1
| Detailed Structure of Compound (5) | |
|---|---|
| No | Structure |
| 5-1 | 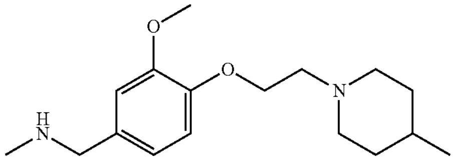 |
| 5-2 | 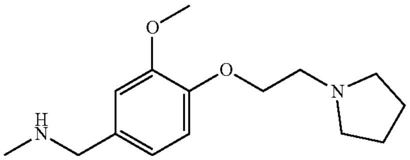 [SMILES: CNCc1ccc(OCCN2CCCC2)c(OC)c1] |
| 5-3 | 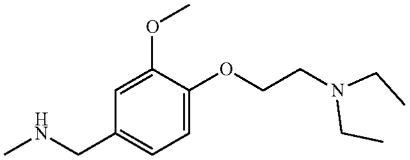 [SMILES: CCN(CC)CCOc1ccc(CNC)cc1OC] |
| 5-4 | 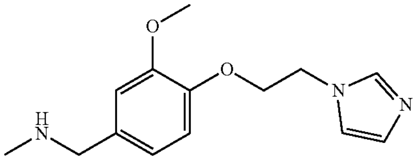 [SMILES: CNCc1ccc(OCCn2ccnc2)c(OC)c1] |
Substituted phenoxyl methyloxirane (7) is synthesized from the nucleophilic substitution between the phenol of different substitutions on the benzene ring and epibromohydrin. The compound series obtained is shown in the following table:
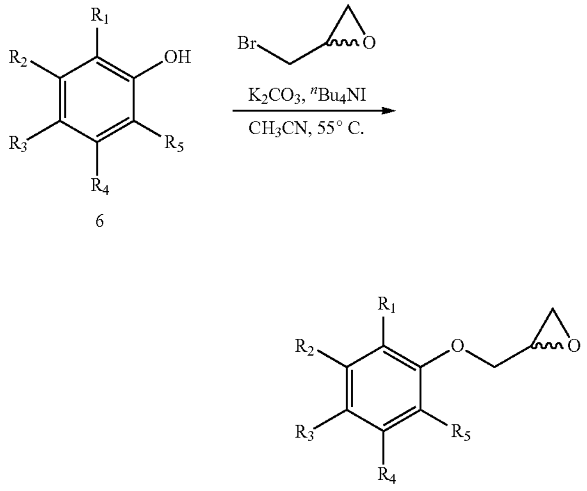
6
7
TABLE 2
| Detailed Structure of Compound (7) | |
|---|---|
| No | Structure |
| 7-1 | 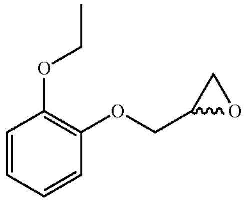 |
| 7-2 | 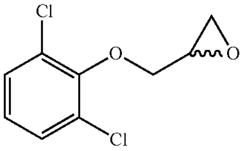 [SMILES: Clc1cccc(Cl)c1OCC1CO1] |
| 7-3 | 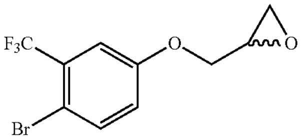 [SMILES: FC(F)(F)c1cc(OCC2CO2)ccc1Br] |
| 7-4 | 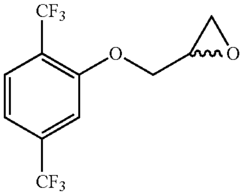 [SMILES: FC(F)(F)c1ccc(C(F)(F)F)c(OCC2CO2)c1] |
| 7-5 | 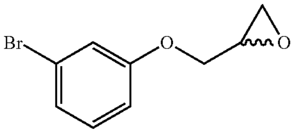 |
| 7-6 | 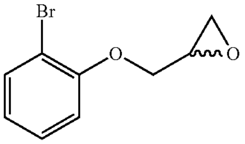 [SMILES: Brc1ccccc1OCC1CO1] |
| 7-7 | 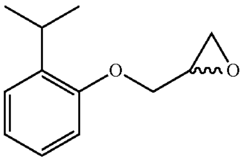 |
| 7-8 | 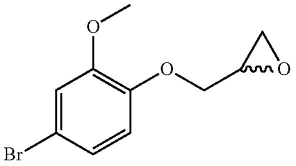 |

TABLE 2-continued
| Detailed Structure of Compound (7) | |
|---|---|
| No | Structure |
| 7-9 | 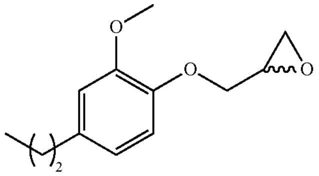 |
| 7-10 | 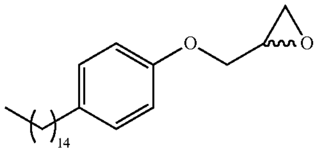 |
| 7-11 | 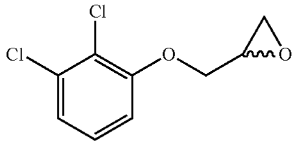 [SMILES: Clc1cccc(OCC2CO2)c1Cl] |
| 7-12 | 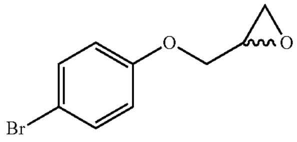 |
| 7-13 | 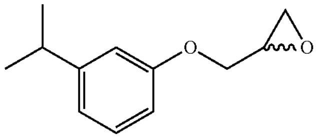 |
| 7-14 | 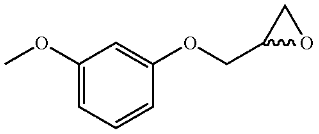 |
| 7-15 | 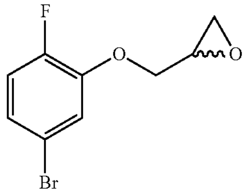 [SMILES: Fc1ccc(Br)cc1OCC1CO1] |
| 7-16 | 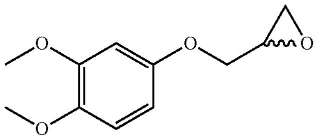 |
| 7-17 | 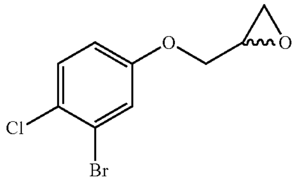 [SMILES: Clc1ccc(OCC2CO2)cc1Br] |
TABLE 2-continued
| Detailed Structure of Compound (7) | |
|---|---|
| No | Structure |
| 7-18 | 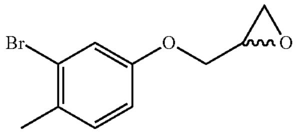 |
| 7-19 | 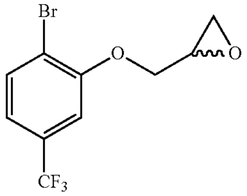 [SMILES: FC(F)(F)c1ccc(Br)c(OCC2CO2)c1] |
| 7-20 | 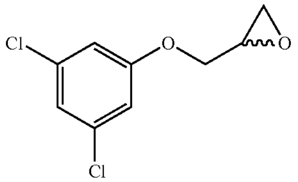 [SMILES: Clc1cc(Cl)cc(OCC2CO2)c1] |
| 7-21 | 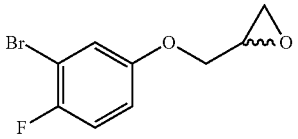 |
| 7-22 | 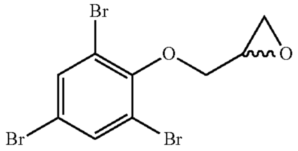 [SMILES: Brc1cc(Br)c(OCC2CO2)c(Br)c1] |
| 7-23 | 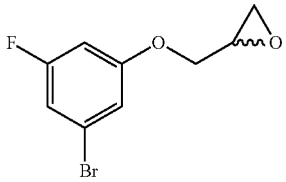 [SMILES: Fc1cc(Br)cc(OCC2CO2)c1] |
| 7-24 | 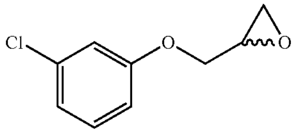 [SMILES: Clc1cccc(OCC2CO2)c1] |
| 7-25 | 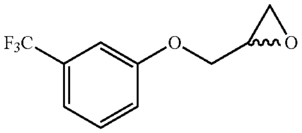 [SMILES: FC(F)(F)c1cccc(OCC2CO2)c1] |
| 7-26 | 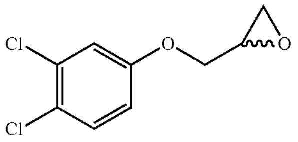 [SMILES: Clc1ccc(OCC2CO2)cc1Cl] |

TABLE 2-continued

| Detailed Structure of Compound (7) | |
|---|---|
| No | Structure |
| 7-27 | 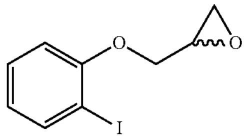 [SMILES: Ic1ccccc1OCC1CO1] |
| 7-28 | 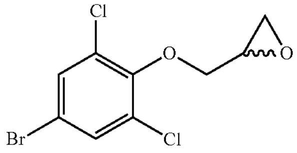 |
| 7-29 | 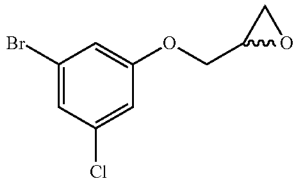 |
| 7-30 | 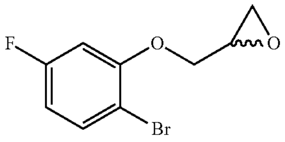 [SMILES: Fc1ccc(Br)c(OCC2CO2)c1] |
| 7-31 | 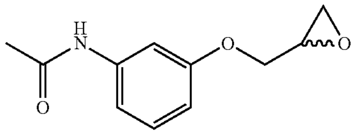 |
| 7-32 | 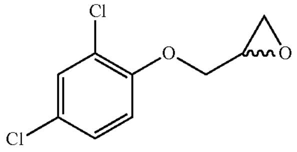 [SMILES: Clc1ccc(OCC2CO2)c(Cl)c1] |
| 7-33 | 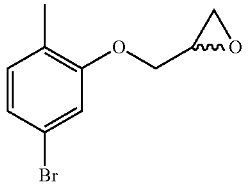 |
| 7-34 | 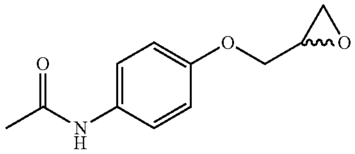 |
| 7-35 | 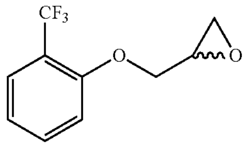 [SMILES: FC(F)(F)c1ccccc1OCC1CO1] |

TABLE 2-continued

| Detailed Structure of Compound (7) | |
|---|---|
| No | Structure |
| 7-36 | 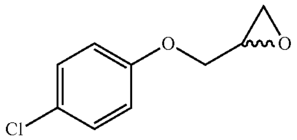 [SMILES: Clc1ccc(OCC2CO2)cc1] |
| 7-37 | 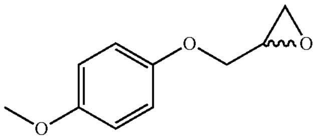 |
| 7-38 | 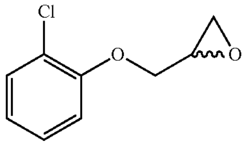 [SMILES: Clc1ccccc1OCC1CO1] |
| 7-39 | 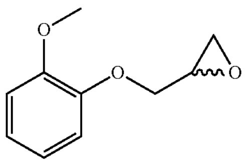 |

EMBODIMENT 1 synthesis of 1-(2-ethoxyphenoxy)-3-((3-methoxy-44-(4-tnethylpiperidin-1-yl)ethoxy)benzyl)(methyl)amino)propan-2-ol (SAMS10)

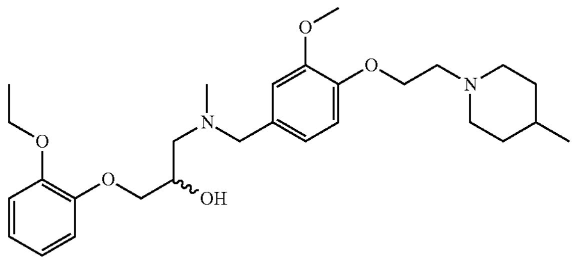 [SMILES: CCOc1ccccc1OCC(O)CN(C)Cc1ccc(OCCN2CCC(C)CC2)c(OC)c1]

Compound 5 used is 1-(3-methoxy-4-(2-(4-methylpiperidin-1-yl)ethoxy)phenyl)-N-methylmethanamine (5-1.1).

Compound 7 used is 2(2-methoxyphenoxy)methyl)oxirane(7-1).

Dissolve 2-((2-ethoxylphenoxyl) methyl) oxirane (7-1) (194 mg, 1.0 mmol) and 1-(3-methoxyl-4-(2-(4-methyl piperidine-1-base) ethoxyl) phenyl)-N-methyl methylamine (5-1) (354 mg, 1.2 mmol) in isopropanol (15 mL), and, with the protection of nitrogen, add pyridine (8.0 μL, 0.1 mmol.) of catalyst dosage. Apply heating reflux for 6 h and the TLC test (developer: dichloramethane-methanol=10:1) raw material disappears. Dilute the reaction liquid with ethyl acetate, and wash the organic phase with water and saturated saline solution in order. Dry it with anhydrous sodium sulfate and filter it. The solvent was evaporated under reduced pressure. The crude product was separated and purified by silica gel column chromatography (mobile phase: dichloromethane-methanol=20:1), a colorless oily substance (437.9 mg 90%) was obtained. $^1$H NMR ($CDCl_3$, 600 MHz) δ (ppm): 6.89 (m, 7H), 4.09 (m, 7H), 3.84 (s, 3H), 3.59 (d, J=19.80 Hz, 1H), 3.47 (d, J=19.80 Hz, 1H), 3.05 (d, J=17.40 Hz, 2H), 2.90 (t, J=9.60 Hz, 2H), 2.61 (m, 2H), 2.28 (s, 3H), 2.19 (m, 2H), 1.66 (d, J=21.0 Hz, 2H), 1.38 (m, 6H), 0.94 (d, J=8.40 Hz, 3H). $^{13}$C NMR ($CDCl_3$, 150 MHz) δ (ppm): 149.49, 149.39, 148.72, 147.33, 131.62, 122.12, 121.27, 121.10, 115.80, 113.84, 113.16, 112.48, 72.91, 66.61 (2C), 64.51, 62.45, 59.60, 57.25, 55.94, 54.37 (2C), 42.43, 33.84 (2C), 30.39, 21.76, 14.93, IR (KBr, $cm^{-1}$): 2924, 2871, 2851, 2794, 2360, 2340, 1592, 1512, 1494, 1460, 1419, 1368, 1321, 1272, 1217, 1138, 1035, 980, 863, 803, 772, 670. HRMS (ESI): m/z calcd. for $C_{28}H_{43}N_2O_5$ $(M+H)^+$: 487.3172. found: 487.3199.

The preparation method of compounds CHJ02029-CHJ05004 in Examples 2-58 is the same as that in Example 1. The difference is that different compounds 5 and 7 are used for synthesis. Specifically, the raw materials of compound 5 and compound 7 used in each embodiment are as follows in the corresponding embodiment record.

EMBODIMENT 2 synthesis of 1-(2,6-dichlorophenoxy)-3-((3-methoxy-4-(2-(4-methylpiperidin-1-yl)ethoxy)benzyl) (methyl)amino)propan-2-ol (CHJ02029)

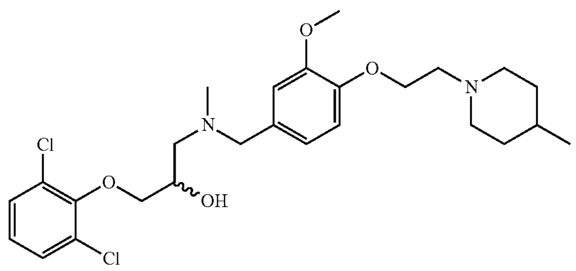 [SMILES: COc1cc(CN(C)CC(O)COc2c(Cl)cccc2Cl)ccc1OCCN1CCC(C)CC1]

Compound 5 used is 1-(3-methoxy-4-(2-(4-methylpiperldin-1-yl)ethoxy)phenyl)-N-methylmethanamine (5-1).

Compound 7 used is 2-((2,6-dichlorophenoxy)methyl) oxirane (7-2).

Colorless oil, yield 88%, $^1$H NMR ($CD_3OD$, 400 MHz) δ (ppm): 7.36 (d, J=8.0 Hz, 2H), 7.08 (t, j=8.0 Hz, 1H), 7.01 (s, 1H), 6.87 (m, 2H), 4.15 (m, 3H), 3.99 (m, 2H), 3.80 (s, 3H), 3.59 (m, 2H), 3.14 (d, J=11.20 Hz, 2H), 2.92 (t, J=5.60 Hz, 2H), 2.74 (m, 1H), 2.59 (dd, J=12.80, 7.60 Hz, 1H), 2.32. (m, 5H), 1.70 (d, J=12.80 Hz, 2H), 1.45 (s, 1H), 1.30 (m 2H), 0.95 (d, J=6.4 Hz, 3H). $^{13}$CNMR ($CD_3OD$, 100 MHz) δ (ppm) 151.27, 149.68, 147.30, 131.70, 129.04, 128.89 (3C), 125.31, 121.62, 113.84, 113.09, 75.76, 67.86, 66.25, 62.02, 59.27, 56.86, 55.00, 53.81 (2C), 41.86, 33.04 (2C), 29.92, 20.60. IR (KBr, $cm^{-1}$): 2947, 2926, 2872, 2841, 2792, 2360, 2340, 1651, 1592, 1511, 1475, 1455, 1367, 1286, 1262, 1230, 1127, 1036, 979, 937, 863, 807, 670. HRMS (ESI): m/z calcd for $C_{26}H_{37}Cl_2N_2O_4$ $(M+H)^+$: 511.2130. found: 511.2047.

EMBODIMENT 3 synthesis of 1-(4-bromo-3-(trifluoromethyl)phenoxy)-3-((3-methoxy-4-(2-(4-methylpiperidin-1-yl) ethoxy)benzyl)(methyl)amino)propan-2-ol (CHJ02049)

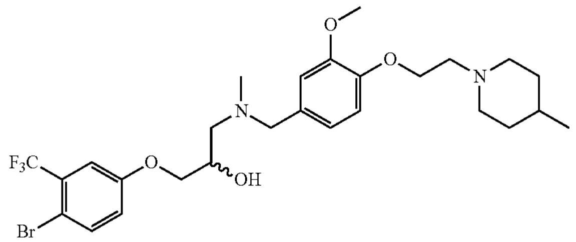 [SMILES: COc1cc(CN(C)CC(O)COc2ccc(Br)c(C(F)(F)F)c2)ccc1OCCN1CCC(C)CC1]

Compound 5 used is 1-(3-methoxy-4-(2-(4-methylpiperdin-1-yl)ethoxy)phenyl)-N-methylmethanamine (5-1).

Compound 7 used is 2-((4-bromo-3-(trifluoromethyl)phenoxy)methyl)oxirane (7-3).

Colorless oil, yield 87%, $^1$H NMR ($CD_2OD$, 400 MHz) δ (ppm): 7.64 (d, J=8.80 Hz, 1H), 7.26 (s, 1H), 7.02 (d, J=8.80 Hz, 1H), 6.95 (s, 1H), 6.83 (q, J=8.0 Hz, 2H), 4.08 (m, 4H), 3.91 (m, 1H), 3.75 (s, 3H), 3.50 (q, J=12.80 Hz, 2H), 3.03 (d, J=11.60 Hz, 2H), 2.80 (t, J=5.60 Hz, 2H), 2.62 (dd, J=12.40, 5.60 Hz, 1H), 2.48 (dd, J=12.40, 6.40 Hz, 1H), 2.32 (s, 3H), 2.17 (t, 11.60 Hz, 2H), 1.66 (d, J=12.40 Hz, 2H), 1.39 (s, 1H), 1.29 (m, 2H), 0.94 (d, J=6.40 Hz, 3H). $^{13}$CNMR ($CD_3OD$, 100 MHz) δ (ppm): 158.33, 149.62, 147.45, 135.7 (2C), 131.91, 121.46 (2C), 118.91, 114.35, 114.29, 113.48, 113.06, 70.99, 67.29, 66.69, 62.29, 58.70, 57.12, 54.94, 54.00 (2C), 42.25, 33.48 (2C), 33.25, 20.75. IR (KBr, $cm^{-1}$): 2926, 2872, 2849, 2793, 2370, 2323, 1684, 1651, 1556, 1512, 1474, 1455, 1419, 1367, 1330, 1313, 1260, 1235, 1139, 1035, 980, 936, 879, 809, 753. HRMS (ESI): m/z calcd for $C_{27}H_{37}BrF_3N_2O_4$ $(M+H)^+$: 589.1889. found: 589.2404.

EMBODIMENT 4 synthesis of 1-(2,5-bis(trifluoromethyl)phenoxy)-3-((3-methoxy-4-(2-(4-methylpiperidin-1-yl)ethoxy) benzyl)(methyl)amino)propan-2-ol (CHJ02050)

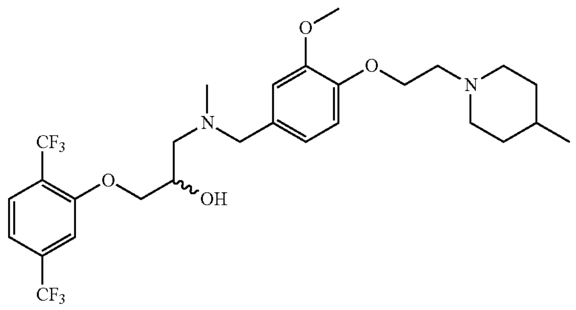 [SMILES: COc1cc(CN(C)CC(O)COc2cc(C(F)(F)F)ccc2C(F)(F)F)ccc1OCCN1CCC(C)CC1]

Compound 5 used is 1-(3-methoxy-4-(2-(4-methylpiperidin-1-yl)ethoxy)phenyl)-N-methylmethanamine (5-1).

Compound 7 used is 2-((2,5-bis(trifluoromethyl)phenoxy)methyl)oxirane (7-4).

White solid, yield 85%, mp: 7072° C., $^1$H NMR ($CD_3OD$, 400 MHz) δ (ppm): 7.77 (d, J=8.0 Hz, 1H), 7.46 (s, 1H), 7.38 (d, J=8.0 Hz, 6.96 (s, 1H), 6.83 (q, J=8.0 Hz, 2H), 4.13 (m, 5H), 3.76 (s, 3H), 3.51 (m, 2H), 3.03 (d, J=11.20 Hz, 2H), 2.80 (t, J=5.60 Hz, 2H), 2.63 (m, 2H), 2.30 (s, 3H) 2.17 (t, J=11.60 Hz, 2H), 1.66 (d, J=12.40 Hz, 2H), 1.40 (s, 1H), 1.29 (m, 2H), 0.94 (d, J=6.40 Hz. 3H), $^{13}$CNMR (CD3OD, 100 MHz) δ (ppm): 157.29, 149.66, 147.41, 131.89, 127.72, 127.67, 121.67, 121.40, 116.72, 116.68, 113.59, 112.97, 109.94, 109.90, 71.45, 67.17, 66.71, 62.28, 59.06, 57.11, 54.90, 53.98 (2C), 41.93, 33.46 (2C), 30.24, 20.73, IR (KBr, $cm^{-1}$): 3562, 3354, 2945, 2877, 2831, 2800, 1624, 1595, 1517, 1463, 1435, 1330, 1259, 1232, 1174, 1132, 1087, 1043, 1022, 962, 910, 866, 833, 804, 750, 673. HRMS. (EST): calcd for $C_{28}H_{37}F_6N_2O_4$ $(M+H)^+$: 579.2658. found: 579.2549.

EMBODIMENT 5 synthesis of 1-(3-bromophenoxy)-3-((3-methoxy-4-(2-(4-methylpiperidin-1-yl)ethoxy)benzyl) (methyl) amino)propan-2-ol (CHJ03001)

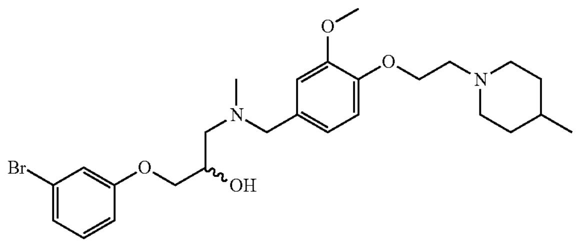

Compound 5 used is 1-(3-methoxy-4-(2-(4-methylpiperidin-1-yl)ethoxy)phenyl)-N-methylmethanamine (5-1).

Compound 7 used is 2-((3-bromophenoxy)methyl)oxirane (7-5).

Colorless oil, yield 86%, $^1$H NMR ($CDCl_3$, 400 MHz) δ (ppm): 7.10 (m, 3H), 6.82 (m, 4H), 4.14 (m, 3H), 3.94 (d, J=4.80 Hz, 2H), 3.85 (s, 3H), 3.62 (d, J=13.60 Hz, 1H), 3.45 (d, J=13.20 Hz, 1H), 2.98 (d, J=11.20 Hz, 2H), 2.84 (t, J=6.0 Hz, 2H), 2.62 (m, 1H), 2.49 (dd, J=12.40, 3.60 Hz, 1H), 2.29 (s, 3H), 2.11 (t, J=11.60 Hz, 2H), 1.64 (d, J=12.40 Hz, 2H), 1.30 (m, 3H), 0.93 (d, J=4.0 Hz, 3H). $^{13}$CNMR ($CDCl_3$, 100 MHz) δ (ppm): 159.54, 149.44, 147.60, 131.18, 130.53, 124.07, 122.76, 121.30, 117.86, 113.58, 112.97, 112.49, 70.63, 66.81, 66.04, 62.37, 59.25 57.40, 55.97, 54.49 (2C), 42.26, 34.19 (2C), 30.57, 21.87. IR (KBr, $cm^{-1}$): 2947, 2924, 2871, 2846, 2792, 2360, 2340, 11651, 1591, 1572, 1512, 1476, 1463, 1459, 1368, 1324, 1283, 1261, 1229, 1157, 1138, 1090, 1035, 991, 936, 861, 804, 800, 674. HRMS (ESI); calcd for $C_{26}H_{38}BrN_2O_4$ $(M+H)^+$: 521.2015. found: 521.1945.

EMBODIMENT 6 synthesis of 1-(2-bromophenoxy)-3-((3-methoxy-4-(2-(4-methylpiperidin-1-yl)ethoxy)benzyl) (methyl) amino)propan-2-ol (CHJ03003)

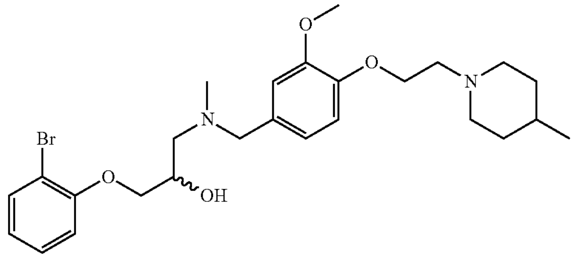 [SMILES: COc1cc(CN(C)CC(O)COc2ccccc2Br)ccc1OCCN1CCC(C)CC1]

Compound 5 used is 1-(3-methoxy-4-(2-(4-methylpiperidin-1-yl)ethoxy)phenyl)-N-methylmethanamine (5-1).

Compound 7 used is 2-((2-bromophenoxy)methyl)oxirane (7-6).

Colorless oil, yield 90%, $^1$H NMR ($CDCl^3$, 400 MHz) δ (ppm): 7.52 (d, J=7.60 Hz, 1H), 7.23 (d, J=8.0 Hz, 1H), 6.85 (m, 5H), 4.14 (t, J=6.0 Hz, 3H), 4.03 (d, J=4.40 Hz, 2H), 3.84 (s, 3H), 3.72 (q, J=7.20 Hz, 1H), 3.63 (d, J=12.80 Hz, 1H), 3.47 (d, J=12.80 Hz, 1H), 2.98 (d, J=11.20 Hz, 2H), 2.84 (t, J=6.40 Hz, 2H), 2.72 (m, 1H), 2.59 (dd, J=12.0, 3.60 Hz, 1H), 2.31 (s, 3H), 2.11 (t, J=11.20 Hz, 2H), 1.64 (d, J=12.40 Hz, 2H), 1.27 (m, 3H), 0.93 (d, J=6.0 Hz, 3H). $^{13}$CNMR ($CDCl_3$, 100 MHz) δ (ppm): 155.10, 149.41, 147.54, 133.30, 131.32, 128.46, 122.19, 121.33, 113.54, 112.94, 112.52, 112.41, 71.39, 66.74, 66.25, 62.47, 59.35, 58.43, 57.39, 55.96, 54.47, 42.43, 34.17, 30.57, 21.86, 18.45. IR (KBr, $cm^{-1}$):2947, 2924, 2871, 2844, 2792, 2361, 2340, 1589, 1513, 1480, 1462, 1417, 1368, 1323, 1276, 1261, 1232, 1158, 1138, 1084, 1053, 1030, 979, 939, 872, 806, 749. HRMS (ESI): m/z calcd for $C_{26}H_{38}BrN_2O_4$ $(M+H)^+$: 521.2015. found: 521, 1943.

EMBODIMENT 7 synthesis of 1(2-isopropylphenoxy)-3-((3-methoxy-4-(2-(4-methylpiperidin-1-yl)ethoxy)benzyl) (methyl)amino)propan-2-ol (CHJ03004)

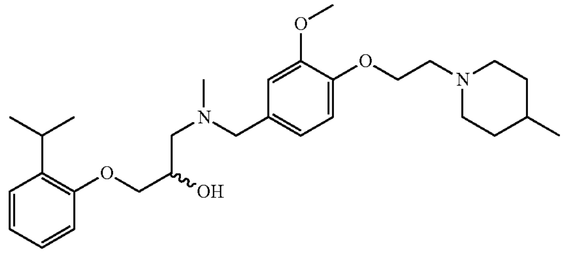 [SMILES: COc1cc(CN(C)CC(O)COc2ccccc2C(C)C)ccc1OCCN1CCC(C)CC1]

Compound 5 used is 1-(3-methoxy-4-(2-(4-methylpiperidin-1-yl)ethoxy)phenyl)-N-methylmethanamine (5-1).

Compound 7 used is 2-((2-isopropylphenoxy)methyl)oxirane (7-7).

Colorless oil, yield 87%, $^1$H NMR ($CDCl^3$, 400 MHz) δ (ppm): 7.2 (d, J=7.60 Hz, 1H), 7.13 (t, J=7.60 Hz, 1H), 6.92 (t, J=7.20 Hz, 1H), 6.82 (m, 4H, 4.14 (m, 3H), 3.00 (m, 2H), 3.94 (s, 3H), 3.65 (d, J=13.20 Hz, 1H), 3.45 (d, J=12.80 Hz 1H), 3.26 (m, 1H), 2.98 (d, J=11.20 Hz, 2H), 2.84 (t, J=6.40 Hz, 2H), 2.69 (m, 1H), 2.53 (dd, J=12.0, 3.20 Hz, 1H), 2.31 (s, 3H), 2.11 (t, J=11.2 Hz, 2H), 1.64 (d, J=12.0 Hz, 2H), 1.30 (m, 3H), 1.19 (d, J=6.80 Hz, 6H), 0.96 (d, J=6.0 Hz, 3H). $^{13}$CNMR ($CDCl_3$, 100 MHz) δ (ppm): 155.82, 149.43, 147.56, 137.05, 131.31, 126.55, 126.07, 121.26, 120.89, 112.93, 112.45, 111.30, 70.34, 66.78, 66.35, 62.47, 59.67, 57.40, 55.94, 54.48, (2C), 42.36, 34.19 (2C), 30.57, 26.90, 22.64 (2C), 21.88. IR (KBr, $cm^{-1}$): 2950, 2925, 2870, 2792, 2360, 2340, 1597, 1513, 1491, 1452, 1418, 1365, 1323, 1261, 1238, 1193, 1138, 1088, 1033, 1030, 980, 937, 878, 822, 805, 751. HRMS (ESI): m/z calcd for $C_{29}H_{45}N_2O_4$ $(M+H)^+$: 485.3379. found: 485.3330.

EMBODIMENT 8 synthesis of 1-(4-bromo-2-methoxyphenoxy)-3-((3-methoxy-4-(2-(4-methylpiperidin-1-yl)ethoxy) benzyl)(methyl)amino)propan-2-ol (CHJ03005)

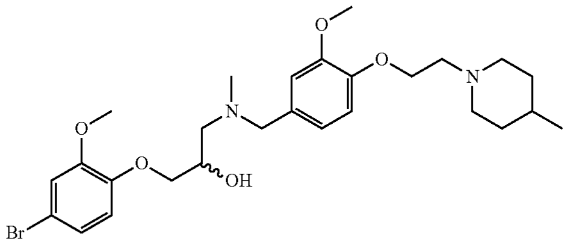 [SMILES: COc1cc(CN(C)CC(O)COc2ccc(Br)cc2OC)ccc1OCCN1CCC(C)CC1]

Compound 5 used is 1-(3-Methoxy-4-(2-(4-methylpiperidin-1-yl)ethoxy)phenyl)-N-methylmethanamine(5-1).

Compound. 7 used is 2-((4-bromo-2-methoxyphenoxy) methyl)oxirane (7-8).

Colorless oil, yield 90%, 1H NMR ($CD_3OD$, 400 MHz) δ (ppm): 7.06 (s, 1H), 7.00 (d, J=8.40 Hz, 1H), 6.95 (s, 1H), 6.83 (m, 3H), 4.10 (m, 3H), 3.96 (dd, J=9.60, 5.60 Hz, 1H), 3.85 (dd, J=9.60, 5.60 Hz, 1H), 3.77 (d, J=12.0 Hz, 6H), 3.53 (m, 2H), 3.06 (d, J=11.60 Hz, 2H), 2.83 (t, J=5.88 Hz, 2H), 2.63 (dd, J=13.44, 5.60 Hz, 1H), 2.49 (dd, J=13.44, 6.80 Hz, 1H), 2.31 (s, 3H), 2.20 (t, J=11.60 Hz, 2H), 1.67 (d, J=12.80 Hz, 2H), 1.40 (s, 1H), 1.28 (m, 2H), 0.94 (d, J=6.40 Hz, 3H). $^{13}$C NMR ($CD_3OD$, 100 MHz) δ (ppm): 150.42, 149.62, 147.91, 147.36, 131.88, 123.29, 121.47, 115.25, 114.88, 113.54, 113.05, 112.79, 71.91, 67.50, 66.61, 62.22, 58.89, 57.07, 55.34, 54.94, 53.96 (2C). 42.13, 33.39 (2C), 30.18, 20.71, IR (KBr, $cm^{-1}$): 2946, 2924, 2843, 2792, 2360, 2340, 1589, 1556, 1539, 1506, 1459, 1418, 1398, 1364, 1324, 1255, 1225, 1183, 1136, 1084, 1029, 936, 857, 797, 670. HRMS (ESI): m/z calcd for $C_{27}H_{40}BrN_2O_5$ $(M+H)^+$: 551.2101. found: 551.2094.

EMBODIMENT 9 synthesis of 1-((3-methoxy-4-(2-(4-methylpiperidin-1-yl)ethoxy)benzyl)(methyl)amino)-3-(2-methoxy-4-propylphenoxy)propan-2-ol (CHJ03011)

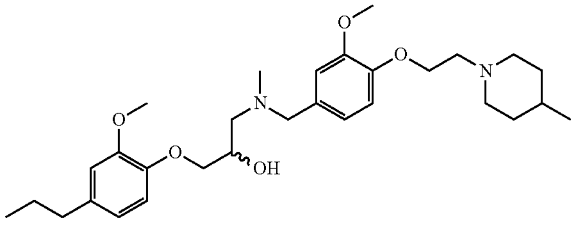 [SMILES: CCCc1ccc(OCC(O)CN(C)Cc2ccc(OCCN3CCC(C)CC3)c(OC)c2)c(OC)c1]

Compound 5 used is 1-(3-methoxy-4-(2-(4-methylpiperidin-1-yl)ethoxy)phenyl)-N-methylmethanamine (5-1).

Compound 7 used is 2-((2-methoxy-4-propylphenoxy) methyl)oxirane (7-9).

White solid, yield 83%, mp: 45-47° C., $^1$H NMR ($CD_3OD$, 400 MHz) δ (ppm): 6.97 (s, 1H), 6.87 (d, J=8.0 Hz, 1H), 6.80 (m, 3H), 6.69 (d, J=8.0 Hz, 1H), 4.10 (m, 3H), 3.96 (dd, J=9.60, 3.60 Hz, 1H), 3.84 (dd, J=9.60, 6.40 Hz, 1H), 3.78 (d, J=13.60 Hz, 6H), 3.54 (m, 2H), 3.05 (d, J=11.60 Hz, 2H), 2.82 (t, J=5.60 Hz, 2H), 2.61 (dd, J=12.80, 5.20 Hz, 1H), 2.51 (q, J=7.20 Hz, 3H), 2.30 (s, 3H), 2.19 (t, J=11.60 Hz, 2H), 1.63 (m, 4H), 1.40 (s, 1H), 1.28 (m, 2H), 0.94 (d, J=7.20 Hz, 6H). $^{13}$C NMR ($CD_3OD$, 100 MHz) δ (ppm): 1.49.66, 149.33, 147.40, 146.45, 136.1.0, 131.85, 121.50, 120.41, 113.95, 113.60, 113.07, 112.54, 72.26, 67.62, 66.67, 62.16, 59.08, 57.08, 55.14, 54.96, 53.97 (2C), 42.01, 37.26, 33.41 (2C), 30.19, 24.48, 20.71, 12.68. IR (1 (KBr, $cm^{-1}$): 2922, 2868, 2791, 2360, 2340, 1597, 1516, 1458, 1419, 1371, 1330, 1261, 1230, 1138, 1091, 1031, 970, 850, 804, 750, 646, 553, 489, HRMS (EST); m/z calcd for $C_{30}H_{47}N_{2d}O_5$ $(M+H)^+$: 515.3485. found: 515.3423.

EMBODIMENT 10 synthesis of 1-((3-methoxy-4-(2-(4-methylpiperidin-1-yl)ethoxy)benzyl)(methyl)amino-3-(4-pentadecylphenoxy)propan-2-ol (CHJ03012)

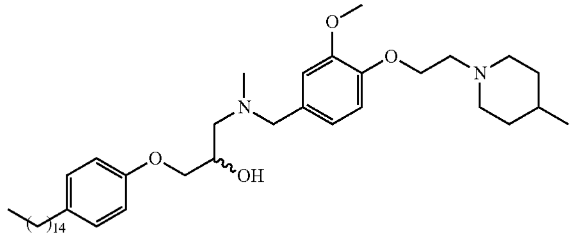

Compound 5 used is 1-(3-methoxy-4(2-(4-methylpiperidin-1-yl)ethoxy)phenyl)-N-methylmethanamine (5-1).

Compound 7 used is 2-((4-pentadecylphenoxy)methyl) oxirane (7-10).

White solid, yield 85%, mp: 40-42° C., $^1$H NMR ($CD_3OD$, 400 MHz) δ (ppm): 7.13 (t, K=7.60 Hz, 1H), 6.97 (s, 1H), 6.84 (m, 2H), 6.72 (m, 3H), 4.11 (m, 3H), 3.98 (m, 1H), 3.86 (m, 1H), 3.76 (s, 3H), 3.55 (m, 2H), 3.05 (d, J=11.60 Hz, 2H), 2.81 ((t, J=5.60 Hz, 2H), 2.59 (m, 4), 2.30

(m, 3H), 2.18 (t, J=11.60 Hz, 2H), 1.64 (m, 4H), 1.28 (s, 27H), 0.94 (d, J=6.40 Hz, 3H), 0.89 (t, J=6.0 Hz, 3H), $^{13}$C NMR ($CD_3OD$, 100 MHz) δ (ppm): 159.02, 149.69, 147.42, 144.23, 131.93, 128.79, 121.47, 120.62, 114.35, 113.65, 113.08, 111.38, 70.34, 67.53, 66.71, 62.22, 59.19, 57.11, 54.98, 53.98 (2C), 53.38, 42.07, 35.56, 33.43 (2C), 31.67, 31.21, 30.21, 29.35 (6C), 29.20, 29.07, 28.91, 22.33, 20.72, 13.04. (KBr, $cm^{-1}$): 2924, 2852, 2794, 2360, 2340, 1591, 1514, 1458, 1367, 1325, 1263, 1151, 1085, 1035, 937, 869, 806, 775, 694. HRMS (ESI): m/z calcd for $C_{41}H_{69}N_2O_4$ $(M+H)^+$: 653.5257, found: 653.5163.

EMBODIMENT 11 synthesis of 1-(2,3-dichlorophenoxy)-3-((3-methoxy-4-(2-(4-methylpiperidin-1-yl)ethoxy)benzyl)(methyl)amino)propan-2-ol (CHJ03013)

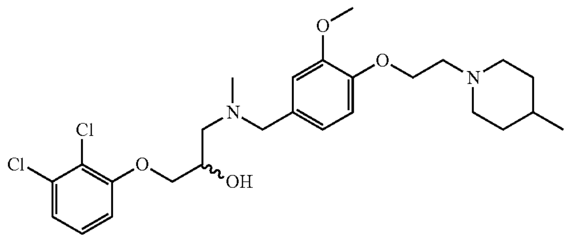 [SMILES: COc1cc(CN(C)CC(O)COc2cccc(Cl)c2Cl)ccc1OCCN1CCC(C)CC1]

Compound 5 used is 1-(3-methoxy-4-(2-(4-methylpiperidin-1-yl)ethoxy)phenyl)-N-methylmethanamine (5-1).

Compound 7 used is 2-((2,3-dichlorophenoxy)methyl) oxirane (7-11).

Colorless oil, yield 88% $^1$H NMR ($CD_3OD$, 400 MHz) δ (ppm): 7.20 (t, J=8.11 Hz, 1H), 7.08 (t, J=8.08 Hz, 1H) 6.96 (m, 2H), 6.82 (q, J=8.05 Hz, 2H), 4.05 (m, 5H), 3.75 (s, 3H), 3.52 (s, 2H), 3.03 (d, J=11.43 Hz, 2H), 2.80 (t, J=5.65 Hz, 2H), 2.69 (dd, J=12.82, 5.4 Hz, 1H), 2.56 (dd, J=12.73, 7.02 Hz, 1H), 2.32 (s, 3H), 2.17 (t, J=11.7 Hz, 2H), 1.65 (d, J=12.71 Hz, 2H), 1.38 (s, 1H), 1.27 (m, 2H), 0.93 (d, J=6.28 Hz, 3H). $^{13}$CNMR ($CD_3O$ D, 100 MHz) δ (ppm): 155.92, 149.65, 147.41, 133.15, 131.90, 127.52, 121.91, 121.45, 121.32, 113.56, 113.03, 111.43, 71.63, 67.36, 66.65, 62.35, 58.90, 57.11, 54.97, 53.97 (2C), 42.20, 33.46 (2C), 30.2.2, 20.76. IR (KBr, $cm^{-1}$): 2947, 2926, 2872, 2841, 2792, 2360, 2340, 1651, 1592, 1511, 1475, 1455, 1367, 1286, 1262, 1230, 1127, 1036, 979, 937, 863, 807, 670. HRMS (ESI): calcd for $C_{26}H_{37}Cl_2N_2O_4$ $(M+H)^+$: 511.2130. found: 511.2095.

EMBODIMENT 12 synthesis of 1-(4-bromophenoxy)-3-((3-methoxy-4-(2-(4-methylpiperidin-1-yl)ethoxy)benzyl) (methyl) amino)propan-2-ol (CHJ03014)

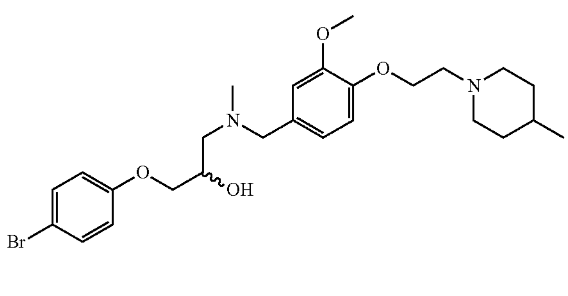

Compound 5 used is 1-(3-methoxy-4-(2-(4-methylpiperidin-1-yl)ethoxy)phenyl)-N-methylmethanamine (5-1).

Compound 7 used is 2-((4-bromophenoxy)methyl)oxirane (7-12).

Colorless oil, yield 81%, $^1$H NMR ($CD_3OD$, 400 MHz) δ (ppm): 7.35 (d, J=8.0 Hz, 2H), 6.95 (s, 1H), 6.82 (m, 4H), 4.10 (t, J=5.60 Hz, 2H), 4.05 (m, 1H), 3.95 (dd, J=9.60, 3.20 Hz, 1H), 3.84 (dd, J=9.60, 6.0 Hz, 1H), 3.77 (s, 3H), 3.50 (q, J=12.80 Hz, 2H), 3.03 (d, J=11.20 Hz, 2H), 2.80 (t, J=5.60 Hz, 2H), 2.61 (dd, J=12.83, 6.0 Hz, 1H), 2.48 (dd, J=12.80, 7.20 Hz, 1H), 2.30 (s, 3H), 2.17 (t, J=11.60 Hz, 2H), 1.65 (d, J=12.80 Hz, 2H), 1.40 (s, 1H), 1.28 (m, 2H), 0.93 (d, J=6.40 Hz, 3H). $^{13}$CNMR ($CD_3OD$, 100 MHz) δ ppm): 158.28, 149.64, 147.44, 131.89 (2C), 131.89, 121.49, 116.19 (2C), 113.56, 113.10, 112.35, 70.66, 67.42, 66.70, 62.27, 58.96, 57.12, 54.88, 53.99 (2C). 42.21, 33.47 (2C), 30.23, 20.76. IR (KBr, $cm^{-1}$): 2947, 2925, 2871, 2844, 2792, 2360, 2331, 1591, 1556, 1512, 1489, 1458, 1418, 1368, 1322, 1285, 1245, 1157, 1074, 1034, 980, 937, 879, 863, 821, 756, 647. HRMS (ESI): calcd for $C_{26}H_{38}BrN_2O_4$ $(M+H)^+$: 521.2015. found: 521.1975.

EMBODIMENT 13 synthesis of 1-(3-isopropylphenoxy)-3-((3-methoxy-4-(2-(4-methylpiperidin-1-yl)ethoxy)benzyl) (methyl)amino)propan-2-ol (CHJ03015)

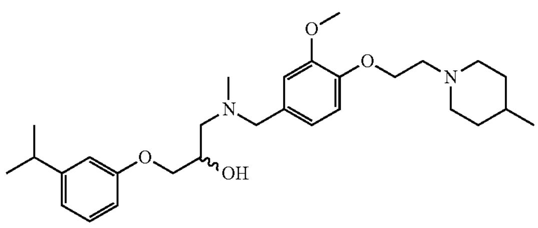 [SMILES: COc1cc(CN(C)CC(O)COc2cccc(C(C)C)c2)ccc1OCCN1CCC(C)CC1]

Compound. 5 used is 1-(3-methoxy-4-(2-(4-methylpiperidin-1-yl)ethoxy)phenyl)-N-methylmethanamine (5-1).

Compound 7 used is 2-((3-isopropylphenoxy)methyl)oxirane (7-13).

Colorless oil, yield 89%, $^1$H NMR ($CD_3OD$, 400 MHz) δ (ppm): 7.15 (t, J=7.60 Hz, 1H), 6.97 (s, 1H), 6.82 (m, 4H), 6.69 (d, J=8.0 Hz, 1H), 4.10 (m, 3H), 3.97 (m, 1H), 3.86 (m, 1H), 3.76 (s, 3H), 3.54 (m, 2H), 3.03 (d, J=11.20 Hz, 2H), 2.82 (m, 3H), 2.63 (dd, J=12.80, 5.60 Hz, 1H), 2.51 (dd, J=12.40, 6.8 Hz, 1H), 2.30 (s, 3H), 2.17 (t, J=11.60 Hz, 2H), 1.65 (d, J=12.40 Hz, 2H), 1.40 (s, 1H), 1.24 (m, 8H), 0.94 (d, J=6.0 Hz, $^3$H). $^{13}$CNMR($CD_3OD$, 100 MHz) δ (ppm): 159.09, 150.37, 149.68, 147.44, 131.90, 128.90, 121.47, 118.55, 113.62, 113.09, 112.54, 111.36, 70.39, 67.54, 66.74, 62.21, 59.25, 57.12, 54.99 (3C), 42.05, 34.05, 33.46 (2C), 30.23, 23.03 (2C), 20.75, IR (KBr, $cm^{-1}$): 2952, 2925, 2871, 2844, 2792, 2360, 2340, 1606, 1588, 1513, 1486, 1460, 1418, 1366, 1320, 1262, 1233, 1286, 1138, 1088, 1037, 1003, 980, 940, 870, 804, 789, 754, 700. HRMS (ESI): m/z calcd for $C_{29}H_{45}N_2O_4$ $(M+H)^{30}$: 485.3379. found: 485.3296.

EMBODIMENT 14 synthesis of 1-((3-methoxy-4-(2-(4-methylpiperidin-1-yl)ethoxy)benzyl)(methyl)amino)-3-(3-methoxyphenoxy)propan-2-ol (CHJ03017)

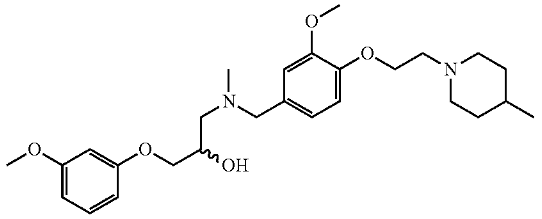

Compound 5 used is 1-(3-methoxy-4-(2(4-methylpiperidin-1-yl)ethoxy)phenyl)-N-methylmethanamine (5-1).

Compound 7 used is 2-((3-methoxyphenoxy)methyl)oxirane (7-14).

Colorless oil, yield 83%, $^1$H NMR ($CD_3OD$, 400 MHz) δ (ppm): 7.13 (t, J=8.0 Hz, 1H), 6.96 (s, 1H), 6.83 (m, 2H), 6.48 (m, 3H), 4.09 (m, 3H), 3.96 (dd, J=9.60, 6.80 Hz, 1H), 3.85 (dd, J=9.20, 6.0 Hz, 1H), 3.75 (d, J=7.60 Hz, 6H), 3.52. (m, 2H), 3.03 (d, J=11.60 Hz, 2H), 2.80 (t, J=5.60 Hz, 2H), 2.61 (dd, J=12.80, 5.60 Hz, 1H), 2.49 (dd, J=12.80, 720 Hz, 2H), 2.30 (s. 3H), 2.16 (t, J=11.60 Hz, 2H), 1.65 (dd, J=12.40 Hz, 2H), 1.40 (s, 1H), 1.27 (m, 2H), 0.93 (d, J=6.40 Hz, 3H). $^{13}$CNMR($CD_3OD$, 100 MHz) δ (ppm): 160.97, 160.23, 149.65, 147.42, 131.90, 129.48, 121.46, 113.58, 113.05, 106.35, 106.02, 100.65, 70.42, 67.48, 66.69, 62.23, 59.13, 57.12, 54.98, 54.28, 53.99 (2C). 42.10, 33.46 (2C), 30.23, 20.76.IR (KBr, $cm^{-1}$): 2947, 2925, 2872, 2837, 2792, 2360, 2340, 1593, 1559, 1513, 1492, 1455, 1418, 1368, 1334, 1287, 1264, 1231, 1201, 1154, 1083, 1036, 980, 940, 834, 807, 762, 687, HRMS (ESI): calcd for $C_{27}H_{41}N_2O_5$ $(M+J)^+$: 473.3015. found: 473.2947.

EMBODIMENT 15

1-(5-bromo-2-fluorophenoxy)-3-(3-methoxy-4-(2-(4-methylpiperidin-1-yl)ethoxy) benzyl)(methyl)amino)propan-2-ol (CHJ03018)

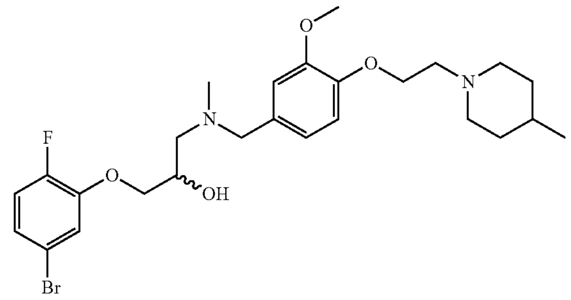

Compound 5 used is 1-(3-methoxy-4-(2-(4-methylpiperidin-1-yl)ethoxy)phenyl)-N-methylmethanamine (5-1).

Compound 7 used is 2-((5-bromo-2-fluorophenoxy) methyl)oxirane (7-15).

Colorless oil, yield 85%, $^1$H NMR ($CD_3OD$, 400 MHz) δ (ppm): 7.23 (d, J=7.20 Hz, 1H), 7.02 (m, 3H), 6.85 (dd, j=22.0, 8.0 Hz, 2H), 4.09 (m, 4H), 3.94 (dd, J=10.0, 5.60 Hz, 1H), 3.78 (s, 3H), 3.50 (m, 2H), 3.05 (d, J=11.60 Hz, 2H), 2.81 (t, J=5.60 Hz, 2H), 2.63 (dd, J=12.80, 5.60 Hz, 1H), 2.50 (dd, J=12.85, 6.51 Hz, 1H), 2.31 (s, 3H), 2.18 (t, J=12.0 Hz, 2H), 1.66 (d, J=13.20 Hz, 2H), 1.41 (s, 1H), 1.28 (m, 2H), 0.94 (d, J=6.0 Hz, 3H). $^1$CNMR($CD_3OD$), 100 MHz) δ (ppm): 150.62, 149.66, 147.40, 131.94, 123.66, 123.59, 121.44, 118.06, 117.16, 116.96, 115.94, 113.59, 112.97, 72.04, 67.36, 66.68, 62.24, 58.85, 57.10, 54.98, 53.98 (2C), 42.10, 33.44 (2C), 30.22, 20.72. IR (KBr, $cm^{-1}$): 2947, 2925, 2872, 2845, 2794, 2360, 2340, 1607, 1511, 1459, 1417, 1404, 1369, 1323, 1303, 1262, 1231, 1138, 1117, 1090, 1020, 962, 935, 877, 837, 803, 755, 627. HRMS (ESI): m/z calcd for $C_{26}H_{37}BrFN_2O_4$ $(M+H)^+$: 539.1921. found: 539.1911.

EMBODIMENT 16 synthesis of 1-(3,4-dimethoxyphenoxy)-3-((3-methoxy-4-(2-(4-methylpiperidin-1-yl)ethoxy)benzyl)(methyl)amino)propan-2-ol (CHJ03019)

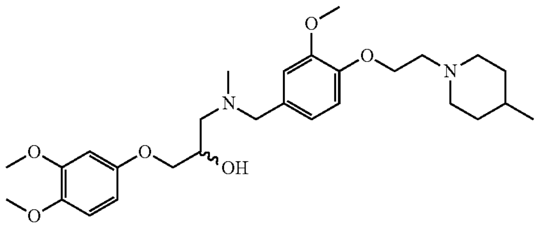

Compound 5 used is 1-(3-methoxy-4-(2-(4-methylpiperidin-1-yl)ethoxy)phenyl)-N-methylmethanamine (5-1).

Compound 7 used is 2-((3,4-dimethoxyphenoxy)methyl) oxirane (7-16).

Colorless oil, yield 87%, $^1$H NMR ($CD_3OD$, 400 MHz) δ (ppm): 6.97 (s, 1H), 6.84 (m, 3H), 6.54 (s, 1H), 6.40 (d, J=8.55 Hz, 1H), 4.08 (m, 3H), 3.93 (dd, J=9.57, 3.33 Hz, 1H), 3.83 (m, 1H), 3.77 (d, J=8.88 Hz, 9H), 3.52 (q, J=12.85 Hz, 2H), 3.05 (d, J=11.47 Hz, 2H), 2.82 (t, J=5.55 Hz, 2H), 2.62 (dd, J=12.84, 5.5 Hz, 1H, 1H), 2.49 (dd, J=12.77, 7.05 Hz, 1H), 2.31 (s, 3H), 2.19 (t, J=11.69 Hz, 2H), 1.66 (d, J=12.59 Hz, 2H), 1.40 (s, 1H), 1.27 (m, 2H), 0.94 (d, J=6.29 Hz, 3H). $^{13}$CNMR($CD_3OD$, 100 MHz) δ (ppm); 153.95, 150.09, 149.63, 147.39, 143.54, 131.88, 121.48, 113.57, 113.07, 112.86, 104.22, 100.91, 70.91, 67.53, 66.61, 62.22, 59.10, 57.08, 55.91, 54.97 (2C), 53.97 (20, 42.12, 33.39 (2C), 30.18, 20.72. IR (KBr, $cm^{-1}$): 2926, 2871, 2850, 2794, 2360, 2340, 1700, 1651, 1611, 1596, 1513, 1418, 1368, 1320, 1261, 1229, 1199, 1162, 1138, 1029, 981, 943, 875, 804, 764, HRMS (EST): m/z calcd for $C_{28}H_{43}N_2O_6$ $(M+H)^+$: 503.3121. found: 501.2817.

EMBODIMENT 17 synthesis of 1-(3-bromo-4-chlorophenoxy)-3-((3-methoxy-4-(2-(4-methylpiperidin-1-yl)ethoxy) benzyl)(methyl)amino)propan-2-ol (CHJ03043)

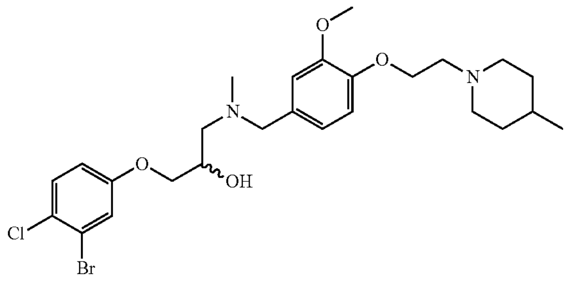 [SMILES: COc1cc(CN(C)CC(O)COc2ccc(Cl)c(Br)c2)ccc1OCCN1CCC(C)CC1]

Compound 5 used is 1-(3-methoxy-4(2-4-methylpiperidin-1-yl)ethoxy)phenyl)-N-methylmethanamine (5-1).

Compound 7 used is 2-((3-bromo-4-chlorophenoxy) methyl)oxirane(7-17).

Colorless oil, yield 89%, $^1H$ NMR ($CDCl_3$, 400 MHz) δ (ppm): 730 (m, 1H), 7.17 (s, 1H), 6.81 (m 4H), 4.11 (m, 3H), 3.91 (m, 2H), 3.84 (s, 3H), 3.61 (d, J=12.0 Hz, 1H), 3.45 (d, J=12.80 Hz, 1H) 2.98 (d, J=11.20 Hz, 2H), 2.84 (t, j=6.40 Hz, 2H), 2.61 (m, 1H) 2.47 (dd, J=12.40, 3.60 Hz, 1H), 2.29 (s, 3H), 2.11 (t, J=11.20 Hz, 2H), 1.63 (d, J=12.40 Hz, 2H), 1.29 (m, 3H), 0.93 (d, J=6.0 Hz, 3H). $^{13}$CNMR($CDCl_3$, 100 MHz) δ (ppm): 157.74, 149.48, 147.66, 131.13, 130.47, 126.18, 122.53, 121.31, 119.57, 115.31, 113.07, 112.55, 71.00, 66.93, 65.99, 62.37, 59.10, 57.39, 55.99, 54.50 (2C), 42.29, 34.21 (2C), 30.56, 21.87IR (KBr, $cm^{-1}$): 2923, 2846, 2360, 2340, 1700, 1651, 1613, 1590, 1559, 1539, 1511, 1470, 1460, 1418, 1373, 1337, 1288, 1262, 1229, 1157, 1138, 1083, 1035, 931, 859, 805, 669. HRMS (ESI): m/z calcd for $C_{26}H_{37}BrClN_2O_4$ $(M+H)^+$: 555.1.625. found: 555.1610.

EMBODIMENT 8 synthesis of 1-(3-bromo-4-methylphenoxy)-3-((3-methoxy-4-(2-(4-methylpiperidin-1-yl)ethoxy) benzyl)(methyl)amino)propan-2-ol (CHJ04010)

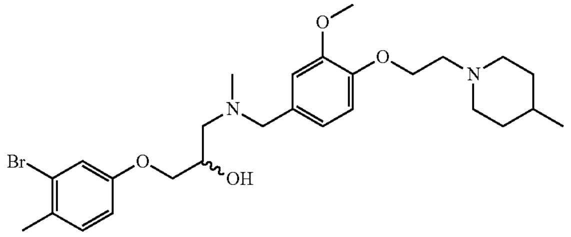

Compound 5 used is 1-(3-methoxy-4-(2-(4-methylpiperidin-1-yl)ethoxy)phenyl)-N-methylmethanamine (5-1).

Compound 7 used is 2-((3-bromo-4-methylphenoxy) methyl)oxirane (7-18).

Colorless oil, yield 82%, $^1H$ NMR ($CD_3OD$, 400 MHZ) δ (ppm): 7.15 (d, J=8.40 Hz, 1H), 7.09 (s, 1H), 6.96 (s, 1H), 6.82 (m, 3H), 4.11 (t, J=5.60 Hz, 2H), 4.04 (m, 1H), 3.95 (m, 1H), 3.83 (m, 1H) 3.77 (s, 3H), 3.51 (q, J=12.80 Hz, 2H), 3.03 (d, J=11.60 Hz, 2H), 2.80 (t, J=5.60 Hz, 2H), 2.60 (dd, J=12.40, 5.60 Hz, 1H), 2.48 (dd, J=13.20, 6.80 Hz, 1H), 2.30 (d, J=2.40 Hz, 6H), 2.17 (t, J=11.60 Hz, 2H), 1.65 (d, J=12.40 Hz, 2H), 1.40 (s, 1H), 1.27 (m, 2H), 0.94 (d, J=6.40 Hz, 3H). $^{13}$CNMR($CD_3OD$, 100 MHz) δ (ppm): 157.77, 149.67, 147.44, 131.94, 130.79, 129.42, 124.18, 121.46, 117.97, 113.65, 113.61, 113.06, 70.79, 67.42, 66.75, 62.25, 59.98, 57.13, 55.00, 53.99 (2C), 42.14, 33.47 (2C), 30.24, 20.74, 20, 50.1IR (KBr, $cm^{-1}$): 2946, 2923, 2871, 2792, 2360, 2340, 1651, 1604, 1579, 1539, 1511, 1492, 1458, 1418, 1368, 1323, 1289, 1262, 1236, 1158, 1138, 1086, 1030, 1003, 932, 866, 838, 806, 757, 671. HRMS (ESI); m/z calcd for $C_{27}H_{40}BrN_2O_O$ $(M+H)^+$: 535.2171. found: 535.2149.

EMBODIMENT 19 synthesis of 1-(2-bromo-5-(trifluoromethyl)phenoxy)-3-((3-methoxy-4-(2-(4-methylpiperidin-1-yl) ethoxy)benzyl)methyl)amino)propan-2-ol (CHJ04011)

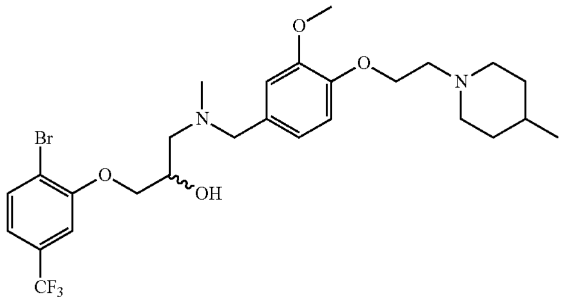

Compound 5 used is 1-(3-methoxy-4-(2-(4-methylpiperidin-1-yl)ethoxy)phenyl)-N-methylmethanamine (5-1).

Compound 7 used is 2-((2-bromo-5-(trifluoromethyl)phenoxy)methyl)oxirane (7-19).

Colorless oil, yield 85%, $^1H$ NMR ($CD_3OD$ 400 MHz) δ (ppm): 7.71 (d, J=8.0 Hz, 1H), 7.27 (s, 1H), 7.16 (d, J=8.40 Hz, 1H), 6.95 (s, 1H), 6.82 (q, J=8.0 Hz, 3H), 4.09 (m, 5H), 3.74 (s, 3H), 3.53 (s, 2H), 3.04 (d, J=11.20 Hz, 2H), 2.81 (t, J=5.60 Hz, 2H), 2.72 (dd, J=12.40, 4.80 Hz, 1H), (dd, J=12.80, 6.40 Hz, 1H), 2.33 (s, 3H), 2.18 (t, J=12.0 Hz, 2H), 1.66 (d, J=12.80 Hz, 2H), 1.40 (s, 1H), 1.29 (m 2H), 0.94 (d, J=6.0 Hz, 3H). $^{13}$CNMR($CD_3OD$, 100 MHz) δ (ppm): 155.81, 149.65, 147.39, 133.69, 131.95, 121.42, 118.16, 118.12, 116.09, 113.57, 112.96, 109.59, 109.55, 71.58, 67.30, 66.67, 62.39, 58.82, 57.10, 54.91, 53.97 (2C), 42.13, 33.45 (2C), 30.22, 20.73. IR (KBr, $cm^{-1}$): 3560, 3354, 2927, 2868, 2818, 1591, 1516, 1462, 1421, 1371, 1332, 1255, 1226, 1165, 1130, 1080, 1041, 1020, 935, 904, 862, 802, 752. HRMS (ESI): m/z calcd for $C_{27}H_{37}BrF_3N_2O_4$ $(M+H)^+$: 589.1889. found: 589.18.27.

EMBODIMENT 20 synthesis of 1-(3,5-dichlorophenoxy)-3-((3-methoxy-4-(2-(4-methylpiperidin-1-yl)ethoxy)benzyl) (methyl)amino)propan-2-ol (CHJ04012)

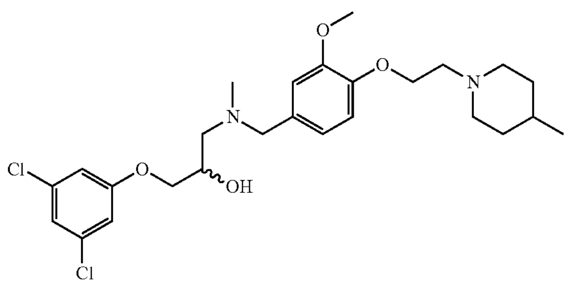 [SMILES: COc1cc(CN(C)CC(O)COc2cc(Cl)cc(Cl)c2)ccc1OCCN1CCC(C)CC1]

Compound 5 used is 1-(3-methoxy-4-(2-(4-methylpiperidin-1-yl)ethoxy)phenyl)-N-methylmethanamine (5-1).

Compound 7 used is 2-((3,5-dichlorophenoxy)methyl) oxirane (7-20).

Colorless oil, yield 88%, $^1$H NMR ($CD_3OD$, 400 MHz) δ (ppm): 6.96 (d, J=9.60 Hz, 2H), 6.84 (m, 4H), 4.10 (t, J=5.60 Hz, 2H), 4.02 (m, 2H), 3.87 (m, 1H), 3.78 (s, 3H). 3.48 (m, 2H), 3.03 (d, J=11.20 Hz, 2H), 2.80 (t, J=6.40 Hz, 2H), 2.60 (dd, J=12.80, 6.0 Hz, 1H), 2.46 (dd, J=12.806.40 Hz, 1H), 2.31 (s, 3H), 2.17 (t, J=12.0 Hz, 2H), 1.65 (d, J=12.75 Hz, 2H), 1.40 (s, 1H), 1.27 (m, 2H), 0.94 (d, J=6.40 Hz, 3H). $^{13}$CNMR ($CD_3OD$, 100 MHz) δ (ppm): 160.34, 149.66, 147.46, 135.12, 131.94, 121.46, 120.38, 113.52, 113.42 (3C), 113.04, 70.04, 67.26, 66.70, 62.29, 58.68, 57.13, 54.99, 54.00 (2C), 42.25, 33.47 (2C), 30.24, 20.75. IR(KBr, $cm^{-1}$): 2948, 2925, 2872, 2843, 2793, 2360, 2340, 1590, 1571, 1513, 1442, 1424, 1368, 13.23, 1303, 1262, 1192, 1157, 1138, 1039, 980, 938, 853, 831, 800, 756, 670. HRMS (ESI): m/z calcd for $C_{26}H_{37}Cl_2N_2O_4$ $(M+H)^+$: 511.2130. found: 511.2075.

EMBODIMENT 21 synthesis of 1-(3-bromo-4-fluorophenoxy)-3-((3-methoxy-4-(2-(4-methylpiperidin-1-yl)ethoxy) benzyl)(methyl)amino)propan-2-ol (CHJ04020)

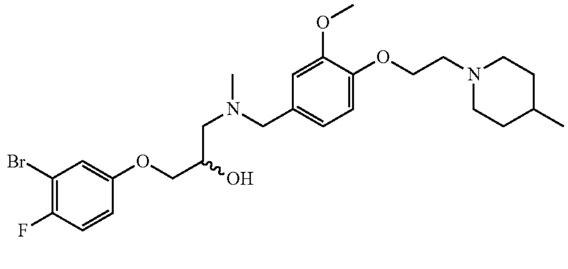

Compound 5 used is 1-(3-methoxy-4-(2-(4-methylpiperidin-1-yl)ethoxy)phenyl)-N-methylmethanamine (5-1).

Compound 7 used is 2-((3-bromo-4-fluorophenoxy) methyl)oxirane (7-21).

Colorless oil, yield 90%, $^1$H NMR (CD3ODD, 400 MHz) δ (ppm): 7.10 (m, 2H), 6.95 (s, 1H), 6.84 (m, 3H), 4.10 (m, 3H), 3.96 (m, 1H), 3.84 (m, 1H), 3.77 (s, 3H), 3.50 (q, J=12.0 Hz, 2H), 3.03 (d, J=11.20 Hz, 2H), 2.80 (t, J=5.20 Hz, 2H), 2.60 (dd, J=12.80, 6.0 Hz, 1H), 2.47 (dd, J=11.20, 6.80 Hz, 1H), 2.31 (s, 3H), 2.17 (t, J=11.60 Hz, 2H), 1.65 (d, 12.40 Hz, 2H), 1.41 (s, 1H), 1.28 (m, 2H), 0.93 (d, J=6.0 Hz, 3H). $^{13}$C NMR($CD_3OD$, 100 MHz) δ (ppm): 155.71, 149.65, 147.44, 131.92, 121.47, 118.73, 116.32, 116.08, 114.95, 114.88, 113.55, 113.07, 71.29, 67.38, 66.71, 62.27, 58.86, 57.12, 55.01, 54.00 (2C). 42.21, 33.47 (2C), 30.23, 20.76. IR (KBr, $cm^{-1}$): 2947, 2925, 2872, 2843, 2793, 2360, 2340, 1591, 1513, 1493, 1458, 1418, 1368, 1322, 1262, 1220, 1203, 1157, 1138, 1088, 1035, 979, 938, 862, 840, 806, 774. HRMS (ESI); calcd for $C_{26}H_{37}BrFN_2O_4$ $(M+H)^+$: 539.1921. found: 539.1888.

EMBODIMENT 22 synthesis of 1-((3-methoxy-4-(2-(4-methylpiperidin-1-yl)ethoxy)benzyl)(methy)amino)-3-(2,4,6-tribromophenoxy)propan-2-ol (CHJ04022)

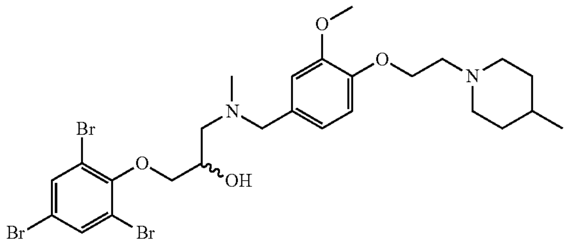

Compound 5 used is 1-(3-methoxy-4-(2-(4-methylpiperidin-1-yl)ethoxy)phenyl)-N-methylmethanamine (5-1).

Compound 7 used is 2-((2,4,6-tribromophenoxy)methyl) oxirane(7-22.

Colorless oil, yield 90%, $^1$H NMR. ($CD_3OD$, 400 MHz) δ (ppm): 7.75 (s, 2H), 6.98 (s, 1H), 6.85 (m, 2H), 4.10 (t, J=5.69 Hz, 2H), 4.22 (m, 1H), 4.12 (t, J=5.61 Hz, 2H), 3.79 (s, 3H), 3.54 (q, J=12.80 Hz, 2H), 3.03 (d, J=11.20 Hz, 2H), 2.80 (t, j=5.60 Hz, 2H), 2.72 dd, J=13.20, 5.20 Hz, 1H), 2.54 (dd, J=12.80, 7.20 Hz, 1H), 2.32 3H), (s, 3H), 2.16 (t, J=11.60 Hz 2H), 1.65 (d, J=12.40 Hz, 2H), 1.39 (s, 1H), 1.30 (m, 2H), 0.93 (d, J=6.40 Hz, 3H) $^{13}$CNMR($CD_3OD$, 100 MHz) δ (ppm): 152.75, 149.67, 147.45, 134.96 (3C), 131.75, 121.55, 118.54, 117.13, 113.66, 113.14, 75.83, 67.96, 66.75, 62.14, 59.34, 57.11, 55.06, 53.99 (2C), 42.08, 33.48 (2C), 30.24, 20.77. IR (KBr, $cm^{-1}$): 2923, 2846, 2360, 2340, 1700, 1651, 1613, 1590, 1559, 1539, 1511, 1470, 1460, 1418, 1373, 1337, 1288, 1262, 1229, 1157, 1138, 1083, 1035, 931, 859, 805. HRMS (ESI): m/z calcd for $C_{26}H_{36}Br_3N_2O_4$ $(M+H)^+$: 677.0225. found: 677.0256.

EMBODIMENT 23 synthesis of 1-(3-bromo-5-fluorophenoxy)-3-((3-methoxy-4-(2-(4-methylpiperidin-1-yl) benzyl) (methyl)amino)propan-2-ol (CHJ04023)

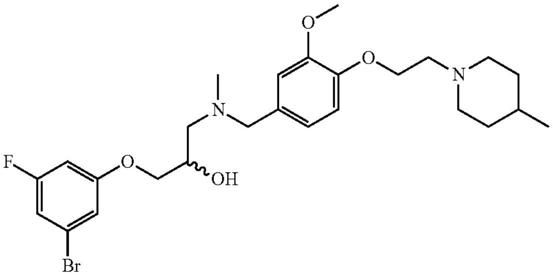 [SMILES: COc1cc(CN(C)CC(O)COc2cc(F)cc(Br)c2)ccc1OCCN1CCC(C)CC1]

Compound 5 used is 1-(3-methoxy-4-(2-(4-methylpiperidin-1-yl)ethoxy)phenyl)-N-methylmethanamine (5-1).

Compound 7 used is 2-((3-bromo-5-fluorophenoxy) methyl)oxirane(7-23.

Colorless oil, yield 85%, $^1$H NMR ($CD_3OD$, 400 MHz) δ (ppm): 6.95 (s, 1H), 6.85 (m, 4H), 6.65 (d, J=10.80 Hz, 1H), 4.11 (t, J=5.60 Hz, 2H), 4.02 (m, 2H), 3.87 (m, 1H), 3.78 (s, 3H), 3.50 (q, J=12.80 Hz, 2H), 3.03 (d, j=11.20 Hz, 2H), 2.81 (t, 5.60 Hz, 2H), 2.60 (dd, J=12.40, 5.60 Hz, 1H), 2.46 (dd, J=12.80, 6.40 Hz, 1H), 2.31 (s, 3H), 2.17 (t, j=12.0 Hz, 2H), 1.65 (d, J=12.80 Hz, 2H), 1.40 (s, 1H), 1.29 (m, 2H), 0.93 (d, J=6.0 Hz, 3H). $^{13}$CNMR($CD_3OD$, 100 MHz) δ (ppm): 164.64, 162.18, 161.02, 149.65, 147.45, 131.93, 122.34, 121.46, 113.83, 113.29, 110.85, 101.17, 71.09, 67.25, 66.68, 62.28, 58.72, 57.12, 55.00, 53.99 (2C), 42.23, 33.46 (2C), 30.23, 20.76. IR (KBr, $cm^{-1}$): 2947, 2925, 2872, 2841, 2792, 2360, 2340, 1605, 1583, 1512, 1454, 1418, 1367, 1318, 1280, 1263, 1231, 1280, 1263, 1231, 1146, 1084, 1039, 980, 941, 833. HRMS (ESI): m/z calcd for $C_{26}H_{37}BrFN_2O_4$ $(M+H)^+$: 539.1921. found: 539.1879.

EMBODIMENT 24 synthesis of 1-(3-chlorophenoxy-3-((3-methoxy-4-(2-(4-methylpiperidin-1-yl)ethoxy)benzyl) (methyl) amino)propan-2-ol (CHJ04024)

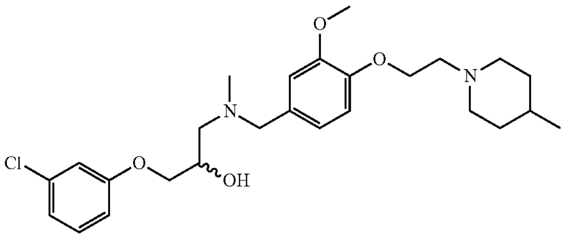 [SMILES: COc1cc(CN(C)CC(O)COc2cccc(Cl)c2)ccc1OCCN1CCC(C)CC1]

Compound 5 used is 1-(3-methoxy-4-(2-(4-methylpiperidin-1-yl)ethoxy)phenyl)-N-methylmethanamine (51).

Compound 7 used is 2-((3-chlorophenoxy)methyl)oxirane (7-24).

Colorless oil, yield 83%, $^1$H NMR ($CD_3OD$, 400 MHz) δ (ppm): 7.21 (t, J=8.40 Hz, 1H), 6.88 (m, 6H), 4.09 (m, 3H), 3.98 (m, 1H), 3.86 (m, 1H), 3.77 (s, 3.51 (q, J=12.80 Hz, 1H), 3.03 (d, J=11.20 Hz, 1H), 2.80 (t, J=5.60 Hz, 2H), 2.61 (dd, J=12.80, 6.80 Hz, 2H), 2.49 (dd, J=12.80, 6.80 Hz, 2H), 2.30 (s, 3H), 2.16 (t, J=11.60 Hz, 2H), 1.65 (d, J=12.80 Hz, 2H), 1.39 (s, 1H), 1.28 (m, 2H), 0.93 (d, J=6.0 Hz, 3H), $^{13}$CNMR ($CD_3OD$, 100 MHz) δ (ppm): 159.91, 149.66, 147.45, 134.44, 131.93, 130.12, 121.47, 120.46, 114.57, 113.58, 113.06, 112.81, 70.71, 67.38, 66.72, 62.26, 58.98, 57.13, 55.00, 53.99 (2C), 42.16, 33.48 (2C), 30.24, 20.76. IR (KBr, $cm^{-1}$): 2947, 2925, 2872, 2843, 2792, 2360, 2340, 1651, 1595, 1580, 1539, 1511, 1470, 1459, 1419, 1367, 1326, 1283, 1260, 1231, 1192, 1157, 1138, 1091, 1036, 979, 935, 870, 807, 770, 681, HRMS (ESI): m/z calcd for $C_{26}H_{38}ClN_2O_4$ $(M+H)^+$: 477.2520. found; 477.2476.

EMBODIMENT 25 synthesis of 1-((3-methoxy-4-(2-(4-methylpiperidin-1-yl)ethoxy)benzyl)(methyl)amino)-3-(3-(trifluoromethyl)phenoxy)propan-2-ol (CHJ04025)

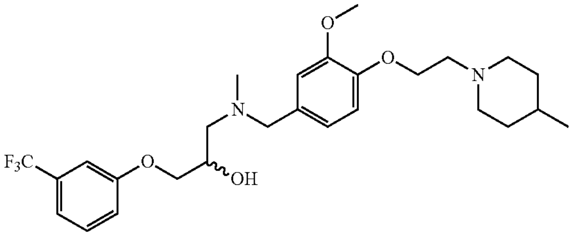 [SMILES: COc1cc(CN(C)CC(O)COc2cccc(C(F)(F)F)c2)ccc1OCCN1CCC(C)CC1]

Compound 5 used is 1-(3-methoxy-4-(2-(4-methylpiperidin-1-yl)ethoxy)phenyl)-N-methylmethanamine (51).

Compound 7 used is 2-((3-(trifluoromethyl)phenoxy) methyl)oxirane (7-25).

Colorless oil, yield 83%, $^1$H NMR ($CD_3OD$, 400 MHz) δ (ppm): 7.44 (t, J=8.0 Hz, 1H), 7.17 (m, 3H), 6.97 (s, 1H), 6.85 (m, 2H), 4.09 (m, 4H), 3.93 (m, 1H), 3.76 (s, 3H), 3.53 (m, 2H), 3.03 (d, J=11.20 Hz, 2H), 2.80 (t, J=5.60 Hz, 2H), 2.63 (dd, J=12.40, 5.20 Hz, 1H), 2.51 (dd, J=12.80, 6.80 Hz, 1H), 2.31 (s, 3H), 2.17 (t, J=11.60 Hz, 2H), 1.65 (d, J=12.80 Hz, 2H), 1.40 (s, 1H), 1.28 (m, 2H), 0.93 (d, J=6.40 Hz, 3H), $^{13}$CNMR ($CD_3OD$, 100 MHz) δ (ppm): 159.32, 149.66, 147.45, 131.92, 131.39, 131.55, 130.01, 121.46, 117.96, 116.91, 113.57, 113.06, 110.96, 70.71, 67.38, 66.72, 62.26, 58.98, 57.13, 55.00, 53.99 (2C), 42.16, 33.48 (2C), 30.24, 20.76. IR (KBr, $cm^{-1}$): 2947, 2926, 2873, 2845, 2794, 2360, 2340, 1651, 1593, 1557, 1539, 1513, 1493, 1453, 1419, 1367, 1330, 1289, 1262, 1234, 1165, 1096, 1065, 1037, 979,934, 880, 794, 753, 698. HRMS (ESI): m/z calcd for $C_{27}H_{38}F_3N_2O_4$ $(M+H)^+$: 511.2784. found: 511.2765.

EMBODIMENT 26 synthesis of 1-(3,4-dichlorophenoxy)-3-((3-methoxy-4-(2-(4-methylpiperidin-1-yl)ethoxy)benzyl) (methyl)amino)propan-2-ol (CHJ04026)

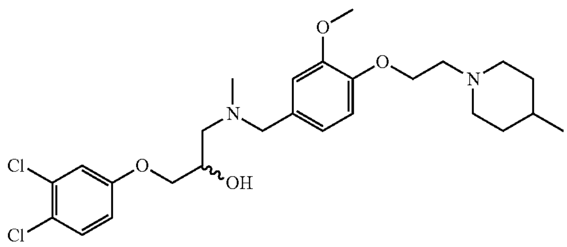 [SMILES: COc1cc(CN(C)CC(O)COc2ccc(Cl)c(Cl)c2)ccc1OCCN1CCC(C)CC1]

Compound 5 used is 1-(3-methoxy-4-(2-(4-methylpiperidin-1-yl)ethoxy)phenyl)-N-methylmethanamine (51).

Compound 7 used is 2-((3,4-dichlorophenoxy)methyl) oxirane (7-26).

Colorless oil, yield 81%, $^1$H NMR ($CD_3OD$, 400 MHz) δ (ppm): 7.36 (d, J=9.20 Hz, 1H), 7.05 (s, 1H), 6.95 (s, 1H), 6.84 (m, 3H), 4.10 (t, J=5.60 Hz, 2H), 4.04 (m, 1H), 3.97 (m, 1H), 3.86 (m, 1H), 3.77 (s, 3H), 3.50 (q, J=12.80 Hz, 1H), 3.03 (d, J=11.60 Hz, 2H), 2.80 (t, J=5.60 Hz, 2H), 2.61 (dd, J=12.80, 6.0 Hz, 1H), 2.47 (dd, J=12.80, 6.80 Hz, 1H), 2.31 (s, 3H), 2.16 (t, J=11.60 Hz, 2H), 1.65 (d, J=12.80 Hz, 2H), 1.40 (s, 1H), 1.27 (m, 2H), 0.94 (d, J=6.40 Hz, 3H). $^{13}$C NMR ($CD_3OD$, 100 MHz) δ (ppm); 158.36, 149.64, 147.45, 132.25, 131.93, 130.48, 123.33, 121.47, 116.16, 114.57, 113.52, 113.07, 70.99, 67.33, 66.70, 62.29, 58.76, 57.13, 54.98, 54.00 (2C), 42.26, 33.48 (2C), 30.24, 20.76. IR (KBr, $cm^{-1}$): 2947, 2926, 2872, 2841, 2792, 2360, 2340, 1651, 1592, 1570, 1539, 1511, 1475, 1455, 1419, 1367, 1286, 1262, 1230, 1191, 1156, 1127, 1092, 1036, 979, 937, 861, 807, 757, 670. HRMS (ESI): m/z calcd for $C_{26}H_{37}Cl_2N_2O_4$ $(M+H)^+$: 511.2130. found: 511.2115.

EMBODIMENT 27 synthesis of 1-(2-iodophenoxy)-3-((3-methoxy-4-(2-(4-methylpiperidin-1-yl)ethoxy)benzyl)(methyl) amino)propan-2-ol (CHJ04027)

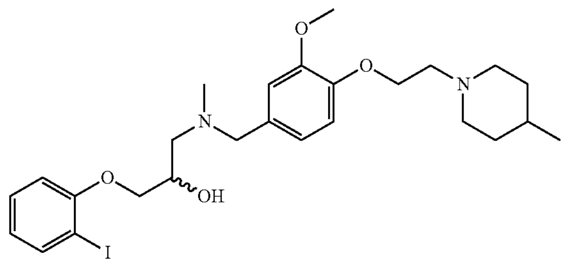 [SMILES: COc1cc(CN(C)CC(O)COc2ccccc2I)ccc1OCCN1CCC(C)CC1]

Compound 5 used is 1-(3-methoxy-4-(2-(4-methylpiperidin-1-yl)ethoxy)phenyl)-N-methylmethanamine (51).

Compound 7 used is 2-((2-iodophenoxy)methyl)oxirane (7-27).

Colorless oil, yield 90%, $^1$H NMR ($CD_3OD$, 400 MHz) δ (ppm): 7.72 (d, J=7.60 Hz, 1H) 7.30 (t, J=8.0 Hz, 1H), 6.96 (s, 1H), 6.90 (d, J=8.40 Hz, 1H), 6.83 (q, J=8.0 Hz, 2H), 6.70 (t, J=7.60 Hz, 1H), 4.09 (m, 3H), 3.98 (m, 2H), 3.74 (s, 3H), 3.55 (q, J=12.80 Hz, 2H), 3.03 (d, J=11.20 Hz, 2H), 2.80 (t, J=5.60 Hz), 2H), 2.74 (d, J=5.20 Hz, 1H), 2.64 (dd, J=12.80, 7.60 Hz, 1H), 2.32 (s, 3H), 2.17 (t, J=11.60 Hz, 2H), 1.65 (d, 12.80 Hz, 2H), 1.40 (s, 1H), 1.29 (m, 2H), 0.94 (d, J=6.40 Hz, 3H) $^{13}$CNMR ($CD_3OD$, 100 MHz) δ (ppm): 157.53, 149.66, 147.40, 139.11, 131.94, 129.30, 122.32, 121.47, 113.60, 113.07, 112.12, 85.66, 71.22, 67.40, 62.42, 59.28, 57.11, 55.00, 53.97 (3C), 42.07, 33.47 (2C), 30.23, 20.75 IR (KBr, $cm^{-1}$): 2946, 2923, 2871, 2844, 2792, 2360, 2340, 1584, 1513, 1471, 1441, 1418, 1368, 1323, 1261, 1231, 1192, 1158, 1138, 1084, 1050, 1030, 1019, 979, 962, 938, 873, 822, 806, 749. HRMS (ESI): m/z calcd for $C_{26}H_{38}IN_2O_4$ $(M+H)^+$: 569.1876. found: 569.1842.

EMBODIMENT 28 synthesis of 1-(4-bromo-2,6-dichlorophenoxy)-3-((3-methoxy-4-(2-(4-methylpiperidin-1-yl)ethoxy) benzyl)(methyl)amino)propan-2-ol (CHJ04033)

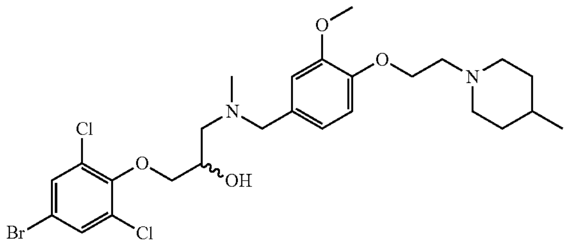 [SMILES: COc1cc(CN(C)CC(O)COc2c(Cl)cc(Br)cc2Cl)ccc1OCCN1CCC(C)CC1]

Compound 5 used is 1-(3-methoxy-4-(2-(4-methylpiperidin-1-yl)ethoxy)phenyl)-N-methylmethanamine (51).

Compound 7 used is 2-((4-bromo-2,6-dichlorophenoxy) methyl)oxirane (7-28).

Colorless oil, yield 84%, $^1$H NMR ($CD_3OD$, 400 MHz) δ (ppm): 7.56 (s, 2H), 6.97 (s, 1H), 6.85 (m, 2H), 4.16 (m, 1H), 4.12 (t, J=5.60 Hz, 2H), 3.99 (m, 2H), 3.79 (s, 3H), 3.52 (m, 2H), 3.04 (d, J=11.20 Hz, 2H), 2.81 (t, J=5.60 Hz, 2H), 2.67 (dd, J=13.20, 4.80 Hz 1H), 2.55 (dd, J=13.20, 7.60 Hz, 1H) 2.30 (s, 3H), 2.17 (t, J=12.0 Hz, 2H), 1.65 (d, J=12.40 Hz, 2H) 1.40 (s, 1H) 1.29 (m, 2H), 0.94 (d, J=6.0 Hz, 3H), $^{13}$CNMR ($CD_3OD$, 100 MHz) δ (ppm): 150.93, 149.67, 147.43, 131.79, 131.46 (3C), 129.99, 121.50, 116.13, 113.67, 113.08, 76.07, 67.97, 66.71, 62.14, 59.26, 57.09, 55.02, 53.97 (2C), 42.01, 33.44 (2C), 30.21, 20.76. IR. (KBr, $cm^{-1}$): 2947, 2924, 2872, 2840, 2794, 2360, 2340, 1544, 1511, 1459, 1419, 1375, 1320, 1259, 1231, 1193, 1158, 1138, 1084, 1031, 994, 933, 856, 803. HRMS (ESI): for $C_{26}H_{36}BrCl_2N_2O_4$ $(M+H)^+$: 589.1236. found: 589.1220.

EMBODIMENT 29 synthesis of 1-(3-bromo-5-chlorophenoxy)-3-((3-methoxy-4-(2-(4-methylpiperidin-1-yl)ethoxy) benzyl)(methyl)amino)propan-2-ol. (CHJ04034)

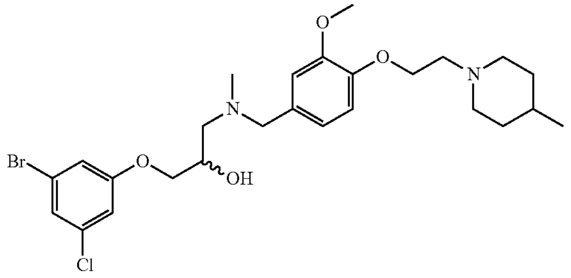

Compound 5 used is 1-(3-methoxy-4-(2-(4-methylpiperidin-1-yl)ethoxy)phenyl)-N-methylmethanamine (51).

Compound 7 used is 2-((3-bromo-5-chlorophenoxy) methyl)oxirane (7-29).

Colorless oil, yield 85%, $^1$H NMR ($CD_3OD$, 400 MHz) δ (ppm): 7.12 (s, 1H), 7.02, 6.95 (s, 1H), 6.91 (s, 1H), 6.83 (m, 2H), 4.10 (t, J=5.60 Hz, 2H), 4.02 (m, 2H), 3.87 (m, 1H), 3.78 (s, 3H), 3.48 (m, 2H), 3.04 (d, J=11.60 Hz, 2H), 2.81 (t, J=5.60 Hz, 2H), 2.60 (dd, J=12.40, 6.0 G), 2.46 (dd, J=12.40, 6.0 Hz, 1H), 2.31 (s, 3H), 2.18 (t, J=12.0 Hz, 2H), 1.66 (d, J=12.80 Hz, 2H), 1.40 (s, 1H), 1.27 (m, 2H), 0.94 (d, J=6.0 Hz, 3H). $^{13}$CNMR($CD_3OD$, 100 MHz) δ (ppm): 160.39, 149.66, 147.44, 135.27, 131.85, 123.18, 122.49, 121.46, 116.33, 113.87, 113.54, 113.04, 71.04, 67.26, 66.67, 62.29, 58.67, 57.11, 55.01, 53.99 (2C), 42.26, 33.45 (2C), 30.22, 20.74, IR (KBr, $cm^{-1}$): 2947, 2926, 2870, 2840, 2793, 2360, 2331, 1588, 1563, 1539, 1512, 1459, 1437, 1420, 1367, 1335, 1319, 1301, 1230, 1259, 1190, 1156, 1138, 1091, 1038, 978, 930, 912, 864, 831, 770, 670, HRMS (ESI): m/z calcd for $C_{26}H_{37}BrClN_2O_4$ $(M+H)^+$: 555.1625. found: 555.1600.

EMBODIMENT 30 synthesis of 1-(2-bromo-5-fluorophenoxy)-3-((3-methoxy-4-(2-(4-methylpiperidin-1-yl)ethoxybenzyl)(methyl)amino))propan-2-ol (CHJ04036)

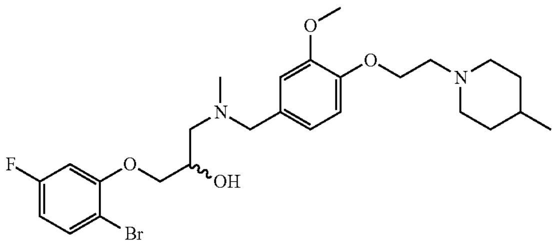 [SMILES: COc1cc(CN(C)CC(O)COc2cc(F)ccc2Br)ccc1OCCN1CCC(C)CC1]

Compound 5 used is 1-(3-methoxy-4-(2-(4-methylpiperidin-1-yl)ethoxy)phenyl)-N-methylmethanamine (51).

Compound 7 used is 2-((2-bromo-5-fluorophenoxy) methyl)oxirane (7-30).

Colorless oil, yield 82%, $^1$H NMR ($CD_3OD$, 400 MHz) δ (ppm): 7.48 (m, 1H), 6.95 (s, 1H), 6.82 (m, 3H), 6.63 (t, J=8.40 Hz, 1H), 4.11 (t, J=5.6 Hz, 3H), 4.01 (m, 2H), 3.76 (s, 3H), 3.53 (s, 2H), 3.04 (d, J=11.20 Hz, 2H), 2.81 (t, J=5.6 Hz, 2H), 2.71 (dd, J=12.80, 5.20 Hz, 1H), 2.58 (dd, J=12.80, 7.20 Hz, 1H), 2.32 (s, 3H), 2.18 (t, J=11.60 Hz, 2H), 1.66 (d, J=12.80 Hz, 2H), 1.41 (s, 1H), 1.29 (m, 2H), 0.94 (d J=6.40 Hz. 3H). $^{13}$CNMR ($CD_3OD$, 100 MHz) δ (ppm): 164.01, 161.58, 156.35, 149.65, 147.40, 133.34, 131.93, 121.47, 113.59, 107.89, 106.05, 101.44, 71.52, 67.28, 66.65, 62.36, 58.95, 57.09, 54.96, 53.96 (2C), 42.01, 33.43 (2C), 30.21, 20.73. IR (KBr, $cm^{-1}$): 3529, 3277, 3088, 2929, 2852, 2796, 2769, 2428, 1681, 1604, 1514, 1477, 1452, 1417, 1371, 1286, 1259, 1224, 1151, 1101, 1037, 960, 871, 833, 790, 748, 609, 451. HRMS (ESI): m/z calcd for $C_{26}H_{37}BrFN_2O_4$ $(M+H)^+$: 539.1921. found: 539.1914.

EMBODIMENT 31 synthesis of N-(3-(2-hydroxy-3-((3-methoxy-4-(2-(4-methylpiperidin-1-yl)ethoxy)benzyl)(methyl) amino)propoxy)phenyl)acetamide (CHJ04058)

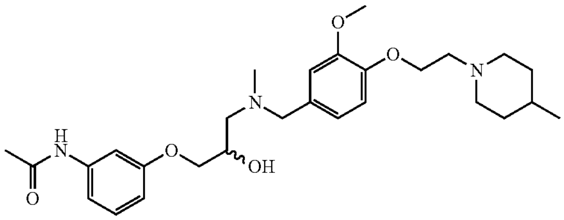 [SMILES: COc1cc(CN(C)CC(O)COc2cccc(NC(C)=O)c2)ccc1OCCN1CCC(C)CC1]

Compound 5 used is 1-(3-methoxy-4-(2-(4-methylpiperidin-1-yl)ethoxy)phenyl)-N-methylmethanamine (51).

Compound 7 used is N-(3-oxirane-2-ylmethoxy)phenyl) acetamide (7-31).

White solid, yield 90%, mp: 60-62° C., $^1$H NMR ($CD_3OD$, 400 MHz) δ (ppm): 7.27 (s, 1H), 7.17 (t, J=8.0 Hz, 1H), 7.05 (m, 2H), 6.86 (m 2H), 6.63 (d, J=8.0 Hz, 1H), 4.11 (m, 3H), 3.97 (m, 1H), 3.87 (m, 1H), 3.78 (s, 3H), 3.55 (s, 2H), 3.13 (dd, J=11.20 Hz, 2H), 2.91 (t, J=5.20 Hz, 1H), 2.65 (dd, J=12.40, 6.80 Hz, 1H), 2.53 (dd, J=12.40, 6.80 Hz, 1H), 2.32 (m, 5H), 2.11 (s, 3H), 1.70 (d, J=13.20 Hz, 2H), 1.46 (s, 1H), 1.32 (m, 3H), 0.94 (d, J=6.0 Hz, 3H), $^{13}$CNMR ($CD_1OD$, 100 MHz) δ (ppm): 170.23, 159.35, 149.61, 147.25, 139.66, 131.87, 129.11, 121.58, 113.73, 113.06, 112.11, 109.83, 106.29, 70.42, 67.37, 66.13, 62.12, 59.09, 56.86, 55.00, 53.79 (2C), 42.01, 33.02 (2C), 29.92, 22.53, 20.59, IR (KBr, cm−1); 2924, 2852, 2360, 2340, 1699, 1670, 1651, 1616, 1556, 1540, 1510, 1491, 1458, 1419, 1373, 1286, 1265, 1230, 1198, 1156, 1083, 1034, 980, 871, 768, 686, 669. HRMS (ESI): m/z calcd for $C_{28}H_{42}N_3O_5$ $(M+H)^+$: 500.3124. found: 500.3071.

EMBODIMENT 32 synthesis of 1-(2,4-dichlorophenoxy)-3-((3-methoxy-4-(2-(4-methylpiperidin-1-yl)ethoxy)benzyl) (methyl)amino)propan-2-ol (CHJ04059)

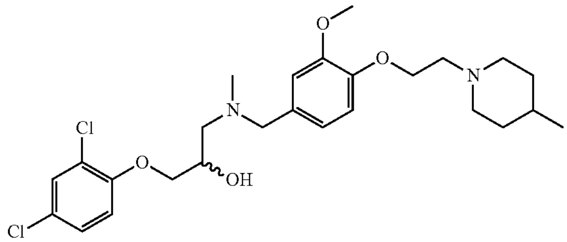 [SMILES: COc1cc(CN(C)CC(O)COc2ccc(Cl)cc2Cl)ccc1OCCN1CCC(C)CC1]

Compound 5 used is 1-(3-methoxy-4-(2-(4-methylpiperidin-1-yl)ethoxy)phenyl)-N-methylmethanamine (51).

Compound 7 used is 2-((2,4-dichlorophenoxy)methyl) oxirane (7-32).

Colorless oil, yield 81%, $^1$H NMR. ($CD_3OD$, 400 MHz) δ (ppm): 7.37 (s, 1H), 7.23 (d, J=8.40 Hz, 1H), 7.00 (d, J=8.80 Hz, 1H), 6.94 (s, 1H), 6.82 (q, J=8.0 Hz, 2H), 4.11 (t, J=5.60 Hz, 3H), 4.00 (m, 2H), 3.75 (s, 3H), 3.52 (s. 2H), 3.06 (d, J=11.60 Hz, 2H), 2.82 (t, J=5.60 Hz, 2H), 2.69 (dd, J=12.80, 5.60 Hz, 1H), 2.54 (dd, J=12.80, 6.80 Hz, 1H), 2.32 (s, 3H), 2.19 (t, J=12.0 Hz, 2H), 1.67 (d, J=12.80 Hz, 2H) (s, 1H), 1.29 (m, 2H), 0.94 (d, J=6.40 Hz, 3H). $^{13}$CNMR ($CD_3OD$, 100 MHz) δ (ppm): 153.47, 149.61, 147.37, 131.88, 129.29, 127.46, 125.32, 123.37, 121.45, 114.33, 113.50, 112.98, 71.53, 67.36, 66.58, 62.33, 58.86, 57.07, 54.92, 53.96 (2C), 42.19, 33.41 (2C), 30.20, 20.73. IR (KBr, cm−1): 2947, 2924, 2872, 2845, 2360, 2339, 1590, 1513, 1484, 1458, 1419, 1389, 1368, 1323, 1290, 1263, 1232, 1156, 1060, 1028, 1007, 938, 867, 846, 804, 745, 653, HRMS (ESI): calcd for $C_{26}H_{37}Cl_2N_2O_4$ $(M+H)^+$: 511.2130, found: 511.2120.

EMBODIMENT 33 synthesis of 1-(5-bromo-2-methylphenoxy)-3-((3-methoxy-4-(2-(4-methylpiperidin-1-yl)ethoxy)benzyl)(methyl)amino)propan-2-ol (CHJ04060)

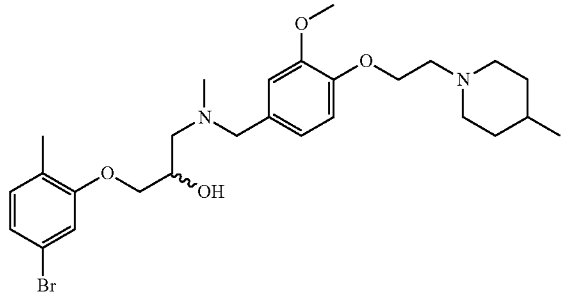 [SMILES: COc1cc(CN(C)CC(O)COc2cc(Br)ccc2C)ccc1OCCN1CCC(C)CC1]

Compound 5 used is 1-(3-methoxy-4-(2-(4-methylpiperidin-1-yl)ethoxy)phenyl)-N-methylmethanamine (51).

Compound 7 used is 2-((5-bromo-2-methylphenoxy) methyl)oxirane (7-33).

Colorless oil, yield 82%. 1H NMR ($CD_3OD$, 400 MHz) δ (ppm): 6.97 (m, 4H), 6.82 (q, j=8.0 Hz, 2H), 4.10 (t, J=5.20 Hz, 3H), 3.97 (dd, J=9.60, 2.80 Hz, 1H), 3.89 (dd, J=9.20, 5.2 Hz, 1H), 3.74 (s, 3H), 3.51 (q, J=12.8 Hz, 2H), 3.04 (d, J=11.20 Hz, 2H), 2.81 (t, J=5.20 Hz, 2H), 2.66 (dd, J=12.80, 6.0 Hz, 1H), 2.49 (dd, J=12.80, 6.0 Hz, 1H), 2.33 (s, 3H), 2.18 (t, J=11.60 Hz, 2H), 2.05 (s, 3H), 1.66 (d, J=12.80 Hz, 2H), 1.41 (s, 1H), 1.27 (m, 2H), 0.94 (d, J=6.0 Hz, 3H). $^{13}$CNMR($CD_3OD$, 100 MHz) δ (ppm): 157.70, 149.65, 147.37, 131.99, 131.30, 125.78, 122.88, 121.36, 119.06, 113.96, 113.48, 112.83, 70.39, 67.47, 66.64, 62.41, 58.80, 57.10, 54.91, 53.98 (2C), 42.28, 33.45 (2C), 30.23, 20.72, 14.59, (KBr, $cm^{-1}$): 2947, 2923, 2871, 2844, 2360, 2340, 1592, 1555, 1513, 1491, 1458, 1417, 1398, 1373, 1260, 1239, 1191, 1129, 1084, 1034, 984, 939, 870, 836, 800, 756. HRMS (ESI): calcd for $C_{27}H_{40}BrN_2O_4$ $(M+H)^+$: 535.2171. found: 535, 2170.

EMBODIMENT 34 synthesis of N-(4-2-hydroxy 3-((3-methoxy-4-(2-(4-methylpiperidin-1-yl)ethoxy)benzyl)(methyl)amino) propoxy)phenyl)acetamide (CHJ04061)

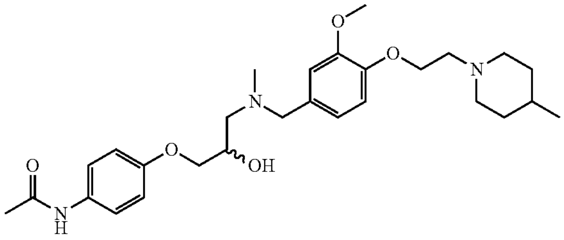 [SMILES: COc1cc(CN(C)CC(O)COc2ccc(NC(C)=O)cc2)ccc1OCCN1CCC(C)CC1]

Compound 5 used is 1-(3-methoxy-4-(2-(4-methylpiperidin-1-yl)ethoxy)phenyl)-N-methylmethanamine (51).

Compound 7 used is N-(4-(oxiran-2-ylmethoxy)phenyl) acetamide (7-34).

White solid, yield 90%, mp: 60-62° C., $^1$H NMR ($CD_3OD$, 400 MHz) δ (ppm): 7.41 (d, J=8.0 Hz, 2H), 6.98 (s, 1H), 6.86 (m, 4H), 4.14 (m, 3M), 3.96 (m, 1H), 3.85 (m, 1H), 3.78 (s, 3H), 3.54 (d, J=5.60 Hz, 2H), 3.14 (d, J=11.20 Hz, 2H), 2.92 (t, J=5.20 Hz, 1H), 2.64 (dd, J=12.80, 7.20 Hz 1H), 2.52 (dd, J=12.80, 7.20 Hz, 1H), 2.32 (m, 5H), 2.09 (s, 3H), 1.70 (d, J=13.20 Hz, 2H), 1.46 (s, 1H), 1.32 (m, 3H), 0.95 (d, J=6.40 Hz, 3H), $^{13}$CNMR ($CD_3OD$, 100 MHz) δ (ppm): 170.23, 159.35, 149.61, 147.25, 139.66, 131.87, 129.11, 121.58, 113.73, 113.06, 112.11, 109.83, 106.29, 70.42, 67.37, 66.13, 62.12, 59.09, 56.86, 55.00, 53.79 (2C), 42.01, 33.02 (2C), 29.92, 22.53, 20.59, IR (KBr, $cm^{-1}$): 2922, 2848, 2362, 2340, 2044, 1681, 1602, 1548, 1512, 1460, 1417, 1369, 1325, 1259, 1240, 1136, 1031, 931, 819, 750, 686, 669. HRMS (ESI) m/z calcd for $C_{28}H_{42}N_3O_5$ $(M+H)^+$: 500.3124. found: 500.3074.

EMBODIMENT 35 synthesis of 14(3-methoxy-4-(2(4-methylpiperidin-1-yl)ethoxy)benzyl)(methyl)amino)-3-(2-(trifluoromethyl)phenoxy)propan-2-ol (CHJ04082)

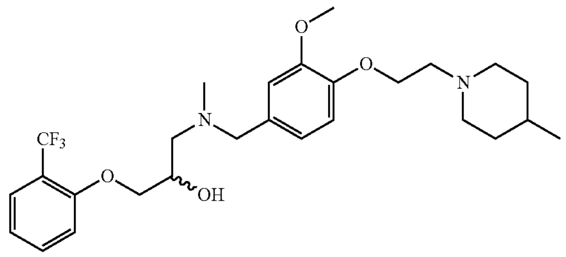

Compound 5 used is 1-(3-methoxy-4-(2-(4-methylpiperidin-1-yl)ethoxy)phenyl)-N-methylmethanamine (51).

Compound 7 used is 2-((2-trifluoromethyl)phenoxy) methyl)oxirane (7-35).

Colorless oil, yield 83%, $^1$H NMR ($CDCl_3$, 400 MHz) δ (ppm): 7.55 (d, J=7.60 Hz, 1H), 7.47 (t, J=8.0 Hz, 1H), 7.00 (t, J=8.40 Hz, 2H), 6.81 (m, 3H), 4.10 (m, 5H), 3.84 (s, 3H), 3.62 (d, J=12.80 Hz, 1H), 3.47 (d, J=12.80 Hz, 1H), 3.00 (d, J=10.80 Hz, 2H), 2.86 (t, J=6.0 Hz, 2H), 2.68 (m, 1H), 2.59 (m, 1H), 2.30 (s, 3H), 2.15 (t, J=10.80 Hz, 2H), 1.64 (d, J=12.0 Hz, 2H), 1.31 (m, 3H), 0.93 (d, J=5.60 Hz, 3H). $^1$C NMR($CDCl_3$, 100 MHz) δ (ppm): 156.61, 149.49, 147.54, 133.28, 131.37, 127.08, 121.34 (2C), 120.33 (2C), 113.18, 112.96, 112.61, 70.86, 66.82, 66.17, 62.45, 59.40, 57.34, 55.95, 54.43 (2C), 42.43, 34.08 (2C), 30.50, 21.81. IR (KBr, $cm^{-1}$): 2039, 2873, 2841, 2794, 2362, 1602, 1510, 1460, 1363, 1323, 1269, 1132, 1033, 974, 948, 879, 808, 758, 650. HRMS (ESI): m/z calcd for $C_{27}H_{38}F_3N_2O_4$ $(M+H)^+$: 511.2784. found: 511.2741.

EMBODIMENT 36 synthesis of 1-(4-chlorophenoxy)-3-((3-methoxy-4-(2-(4-methylpiperidin-1-yl)ethoxy)benzyl)(methyl) amino)propan-2-ol (CHJ04083)

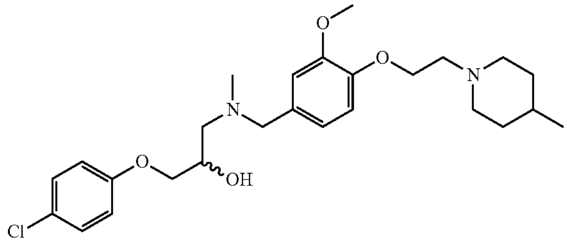 [SMILES: COc1cc(CN(C)CC(O)COc2ccc(Cl)cc2)ccc1OCCN1CCC(C)CC1]

Compound 5 used is 1-(3-methoxy-4-(2-(4-methylpiperidin-1-yl)ethoxy)phenyl)-N-methylmethanamine (51).

Compound 7 used is 2-((4-methoxyphenoxy)methyl)oxirane (7-36).

Colorless oil, yield 90%, $^1$H NMR ($CDCl_3$, 400 MHz) δ (ppm): 7.22 (d, J=15.2 Hz, 2H), 6.81 (m, 5H), 4.16 (t, J=6.0 Hz, 2H), 4.09 (m, 1H), 3.92. (d, J=4.40 Hz, 2H), 3.84 (s, 3H), 3.62 (d, J=13.20 Hz, 1H), 3.45 (d, J=13.20 Hz, 1H), 2.99 (d, J=10.8 Hz, 2H), 2.85 (t, J=6.0 Hz, 2H), 2.63 (t, J=11.60 Hz, 1H), 2.50 (m, 1H), 2.29 (s, 3H), 2.14 (t, J=10.80 Hz, 2H), 1.64 (d, J=12.40 Hz, 2H), 1.32 (m, 3H), 0.93 (d, J=5.60 Hz, 3H), $^{13}$CNMR($CDCl_3$, 100 MHz) δ (ppm): 157.41, 149.51, 147.6.2, 131.25, 129.30 (2C), 125.84, 121.32, 115.88 (2C), 113.16, 112.59, 70.74, 66.91, 66.11, 62.37, 59.29, 57.36, 55.99, 54.47 (2C), 42.28, 34.12 (2C), 30.52, 21.83. IR (KBr $cm^{-1}$): 2947, 2925, 2872, 2843, 2792, 2360, 2325, 1651, 1595, 1539, 1511, 1492, 1458, 1418, 1367, 1322, 1283, 1246, 1157, 1138, 1092, 1035, 1008, 824, 672. HRMS (ESI): calcd for $C_{26}H_{38}ClN_2O_4$ $(M+H)^+$: 477.2520. found: 477.2471.

EMBODIMENT 37 synthesis of 1-((3-methoxy-4-(2-(4-methylpiperidin-1-yl)ethoxy)benzyl)(methyl)amino)-3-(4-methoxyphenoxy)propan-2-ol (CHJ04084)

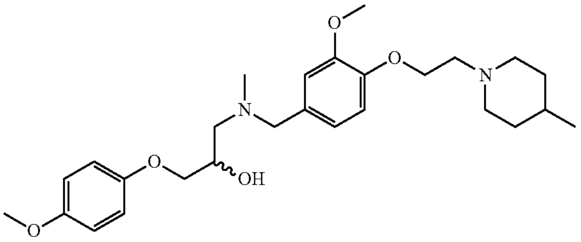

Compound 5 used is 1-(3-methoxy-4-(2-(4-methylpiperidin-1-yl)ethoxy)phenyl)-N-methylmethanamine (51).

Compound 7 used is 2-((4-methoxyphenoxy)methyl)oxirane (7-37).

Colorless oil, yield 90%, $^1$HNMR ($CDCl_3$, 400 MHz) δ (ppm): 6.82 (m, 7H), 4.17 (t, J=6.0 HZ, 2H), 4.09 (m, 1H), 3.91 (d, J=4.40 Hz, 2H), 3.84 (s, 3H), 3.76 (s, 3H), 3.62. (d, J=12.80 Hz, 1H), 3.46 (d, J=12.80 Hz, 1H), 3.01 (d, J=11.20 Hz, 2H), 2.86 (t, J=6.0 Hz, 2H), 2.63 (t, J=11.20, HZ, 1H), 2.51 (m, 1H), 2.28 (s, 3H), 2.16 (t, J=11.20 Hz, 2H), 1.65 (d, J=12.0 Hz, 2H), 1.31 (m, 3H), 0.93 (d, J=5.48 Hz, 3H), $^1$C NMR($CDCl_3$, 100 MHz) δ (ppm): 154.01, 152.97, 149.49, 147.52, 131.40, 121.31, 115.55 (2C), 114.64 (2C), 113.17, 112.57, 71.16, 66.78, 66.29, 62.37, 59.53, 57.34, 55.98, 55.73, 54.43 (2C) 42.25, 34.04 (2C), 30.48, 21.80. IR (KBr, $cm^{-1}$): 2947, 2925, 2871, 2834, 2792, 2360, 2325, 1595, 1510, 1459, 1418, 1368, 1322, 1262, 1231, 1156, 1138, 1036, 980, 937, 878, 824, 748. HRMS (ESI): m/z calcd for $C_{27}H_{41}N_2O_5$ $(M+H)^+$: 473.3015. found: 473.2975.

EMBODIMENT 38 synthesis of 1-(2-chlorophenoxy)-3-((3-methoxy-4-(2-(4-methylpiperidin-1-yl)ethoxy)benzyl) (methyl) amino)propan-2-ol (CHJ04085)

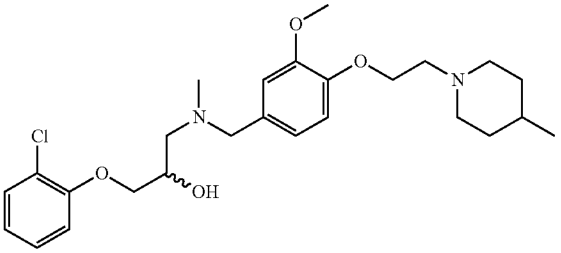

Compound 5 used is 1-(3-methoxy-4-(2-(4-methylpiperidin-1-yl)ethoxy)phenyl)-N-methylmethanamine (51).

Compound 7 used is 2-((2-chlorophenoxy)methyl)oxirane (7-38).

Colorless oil, yield 83%, $^1$H NMR (COCl$_3$, 400 MHz) δ (ppm): 7.34 (d, J=8.0 Hz, 1H), 7.19 (t, J=7.60 Hz, 1H), 6.86 (m, 5H), 4.15 (t, J=6.0 Hz, 3H), 4.03 (d, J=4.40 Hz, 2H), 3.84 (s, 3H), 3.63 (d, J=13.2 Hz, 1H), 3.47 (d, J=13.2 Hz, 1H), 3.00 (d, J=13.14 Hz, 2H), 2.85 (t, J=6.40 Hz, 2H), 2.70 (m, 1H), 2.58 (m, 1H), 2.30 (s, 3H), 2.13 (t, J=11.22 Hz, 2H), 1.64 (d, J=12.06 Hz, 2H), 1.30 (m, 3H), 0.93 (d, J=5.80 Hz, 3H). $^{13}$CNMR(CDCl$_3$, 100 MHz) δ ppm): 154.31, 149.41, 147.52, 131.30, 130.25, 127.69, 123.15, 121.72, 121.34, 113.80, 112.97, 112.53, 71.46, 66.64, 66.24, 62.42, 59.34, 57.36, 55.95, 54.41 (2C), 42.40, 34.08 (2C), 30.58, 21.83. IR (KBr, cm$^{-1}$): 2925, 2872, 2845, 2792, 2360, 2325, 1591, 1512, 1486, 1455, 1418, 1368, 1322, 1276, 1258, 1232, 1158, 1137, 1084, 1061, 980, 937, 877, 807, 749, 693. HRMS (ESI): m/z calcd for $C_{26}H_{38}ClN_2O_4$ (M+H)$^+$: 477.2520. found: 477.2506.

EMBODIMENT 39 synthesis of 1-((3-methoxy-4-(2-(4-methylpiperidin-1-yl)ethoxy)benzyl)(methyl)amino-3-(2-methoxy-phenoxy)propan-2-ol (CHJ04086)

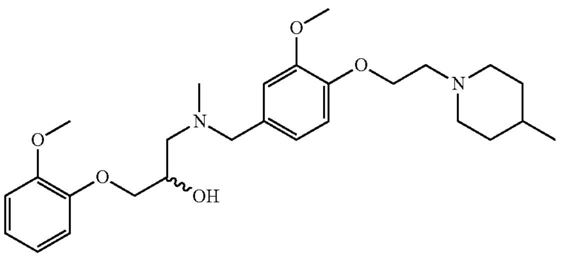 [SMILES: COc1cc(CN(C)CC(O)COc2ccccc2OC)ccc1OCCN1CCC(C)CC1]

Compound 5 used is 1-(3-methoxy-4-(2-(4-methylpiperidin-1-yl)ethoxy)phenyl)-N-methylmethanamine (51).

Compound 7 used is 2-((2-methoxyphenoxy)methyl)oxirane (7-39).

Colorless oil, yield 85%, $^1$H NMR (CDCl$_3$, 400 MHz) δ (ppm): 6.86 (m, 7H), 4.16 (t, J=6.0 Hz, 3H), 4.02 (m, 2), 3.84 (s, 6H), 3.60 (d, J'13.20 Hz, 1H), 3.47 (d, J=13.20 Hz, 1H), 3.03 (d, J=11.20 Hz, 2H), 2.87 (t, J=6.0 Hz, 2H), 2.63 (m, 1H), 2.54 (m, 1H), 2.28 (s, 3H), 2.16 (t, J=10.8 Hz, 2H), 1.65 (d, J=12.0 Hz, 2H), 1.33 (m, 3H), 0.94 (d, J=5.60 Hz, 3H). $^{13}$CNMR(CDCl$_3$100 MHz) δ (ppm): 149.80, 149.37, 148.39, 147.38, 131.50, 121.78, 121.30, 120.93, 114.58, 112.97, 112.50, 112.04, 72.39, 66.46, 66.41, 62.38, 59.50, 57.31, 55.88 (2C), 54.33 (2C), 42.35, 33.89 (2C), 30.45, 21.77. IR (KBr, cm$^{-1}$): 2925, 2872, 2838, 2792, 2360, 2340, 1593, 1556, 1510, 1458, 1418, 1368, 1328, 1250, 1226, 1258, 1157, 1125, 1090, 1030, 980, 939, 876, 807, 744. HRMS (ESI): (ESI): m/z calcd for $C_{27}H_{41}N_2O_5$ (M+H)$^+$: 473.2972. found: 473.2972.

EMBODIMENT 40 synthesis of 1-(3-bromo-4-methylphenoxy)-3-((3-methoxy-4-(2-(pyrrolidin-1-yl)ethoxy)benzyl)(methyl)amino)propan-2-ol (CHJ04064)

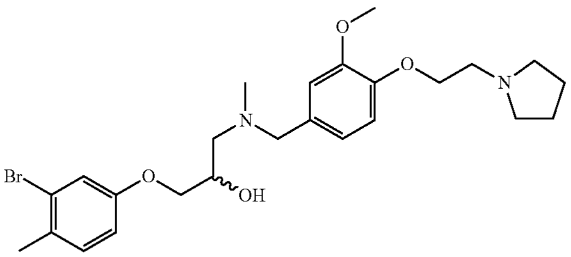 [SMILES: COc1cc(CN(C)CC(O)COc2ccc(C)c(Br)c2)ccc1OCCN1CCCC1]

Compound 5 used is 1-(3-methoxy-4-(2-(pyrrolidin-1-yl)ethoxy)phenyl)-N-methylmethanamine (52).

Compound 7 used is 2-((3-bromo-4-methylphenoxy)methyl)oxirane 7-18).

Colorless oil, yield 80%, $^1$H NMR (CD$_3$OD, 400 MHz) δ (ppm): 7.15 (d, J=8.40 Hz, 1H), 7.09 (s, 1H), 6.98 (s, 1H), 6.3 (m, 3H), 4.13 (t, J=5.20 Hz, 2H), 4.05 (m, 1H), 3.96 (m, 1H), 3.82 (m, 4H); 3.54 (m, 2H), 3.04 (t, J=5.20 Hz, 2H), 2.83 (s, 4H), 2.61 (dd, J=12.40, 5.6 Hz 1H), 2.49 (dd, J=12.80, 6.80 Hz, 1H), 2.30 (d, J=6.80 Hz, 6H), 1.87 (s, 4H). $^{13}$CNMR (CD$_3$OD, 100 MHz) δ (ppm): 157.76, 149.69, 147.25, 132.08, 130.80, 129.43, 124.18, 121.47, 117.94, 113.75, 113.64, 112.98, 70.76, 67.36, 67.27, 62.21, 58.95, 54.94, 54.50, 54.23 (2C), 42.08, 22.77 (2C). 20.50, IR (KBr, cm$^{-1}$) 2924, 2873, 2850, 2793, 2360, 2339, 1604, 1513, 1492, 1459, 1418, 1369, 1325, 1263, 1235, 1139, 1031, 976, 928, 863, 805, 750, 669. HRMS (ESI): (ESI): m/z calcd for $C_{25}H_{36}BrN_2O_4$ (M+H)$^+$: 507.1858. found: 507.1858.

EMBODIMENT 41 synthesis of 1-(2-bromo-5-(trifluoromethyl)phenoxy)-3-((3-methoxy-4-(2-(pyrrolidin-1-yl)ethoxy)benzyl)(methyl)amino)propan-2-ol (CHJ04065)

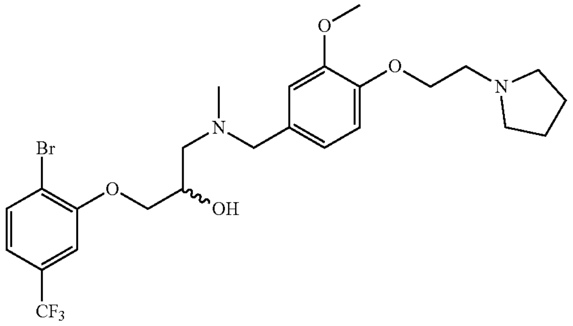 [SMILES: COc1cc(CN(C)CC(O)COc2cc(C(F)(F)F)ccc2Br)ccc1OCCN1CCCC1]

Compound 5 used is 1-(3-methoxy-4-(2-pyrrolidin-1-yl)ethoxy)phenyl)-N-methylmethanamine (52).

Compound 7 used is 2-((2-bromo-5-(trifluoromethyl)phenoxy)methyl)oxirane 7-19).

Colorless oil, yield 82%, $^1$H NMR (CD$_3$OD, 400 MHz) δ (ppm): 7.71 (d, J=8.0 Hz, 1H), 7.27 (s, 1H), 7.16 (d, J=8.0 Hz, 1H), 6.97 (s, 1H), 6.84 (m, 2H), 4.10 (m, 5H), 3.75 (s, 3H), 3.55 (s, 2H), 3.07 (t, J=5.20 Hz, 2H), 2.87 (s, 4H), 2.73 (dd, J=12.80, 4.80 Hz, 1H), 2.60 (dd, J=12.40, 6.40 Hz, 1H), 2.34 (s, 3H), 1.89 (s, 4H), 13CNMR (CD30D, 100 MHz) δ (ppm): 155.80, 149.68, 147.16, 133.70, 132.16, 130.42, 121.44, 118.14, 116.09, 113.78, 112.88, 109.57, 71.55, 67.09, 62.34, 58.80, 54.86, 54.45, 54.22 (2C), 42.08, 23.39, 22.76 (2C), 12.54, IR (KBr, $cm^{-1}$): 2968, 2938, 2879, 2793, 2361, 2323, 1734, 1700, 1518, 1492, 1459, 1419, 1398, 1328, 1268, 1252, 1167, 1137, 1080, 1035, 977, 906, 861, 748, 670. HRMS (ESI): m/z calcd for $C_{25}H_{33}BrF_3N_2O_4$ $(M+H)^+$: 561.1576. found: 561.1569.

EMBODIMENT 42 synthesis of 1-(3,5-dichlorophenoxy)-3-((3-methoxy-4-(2-(pyrrolidin-1-yl)ethoxy)benzyl)(methyl) amino)propan-2-ol (CHJ04066)

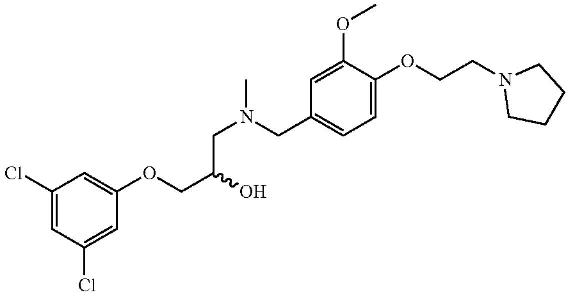 [SMILES: COc1cc(CN(C)CC(O)COc2cc(Cl)cc(Cl)c2)ccc1OCCN1CCCC1]

Compound 5 used is 1-(3-methoxy-4-(2-(pyrrolidin-1-yl) ethoxy)phenyl)-N-methylmethanamine (52).

Compound 7 used is 2-((3,5-dichlorophenoxy)methyl) oxirane 7-20).

Colorless oil, yield 84%, $^1$H NMR ($CD_3OD$ 400 MHz) δ (ppm): 6.98 (d, J=3.60 Hz, 2H), 6.87 (m, 3H), 6.82 (d, J=8.40 Hz, 1H), 4.13 (t, J=4.80 Hz, 2H), 4.03 (m, 2H), 3.88 (m, 1H), 3.79 (s, 3H), 3.52 (q, J=12.80 Hz, 2H), 3.06 (t, J=5.20 Hz, 2H), 2.85 (s, 4H), 2.62 (dd, J=12.40, 6.0 Hz, 1H), 2.47 (dd, J=12.40, 6.40 Hz, 1H), 2.32 (s, 3H), 1.88 (s, 4H). $^{13}$CNMR ($CD_3OD$, 100 MHz) δ (ppm): 160.34, 149.67, 147.23, 135.12, 132.16, 121.46, 120.37, 113.68, 113.40 (3C), 112.94, 71.00, 67.21, 67.17, 62.25, 58.63, 54.92, 54.48, 54.24 (2C), 42.20, 22.76 (2C). IR (KBr, cm−1): 2933, 2877, 2843, 2787, 2361, 2340, 1591, 1514, 1454, 1421, 1330, 1290, 1261, 1230, 1165, 1130, 1089, 1028, 964, 908, 875, 808, 752, 692, 661, 617. HRMS (ESI): m/z calcd for $C_{24}H_{33}Cl_2N_2O_4$ $(M+H)^+$: 483.1817. found: 483.1801.

EMBODIMENT 43 synthesis of 1-((3-methoxy-4-(2-(pyrrolidin-1-yl) ethoxy)benzyl)(methyl)amino)-3-(2,4,6-tribromophenoxy)propan-2-ol (CHJ04068)

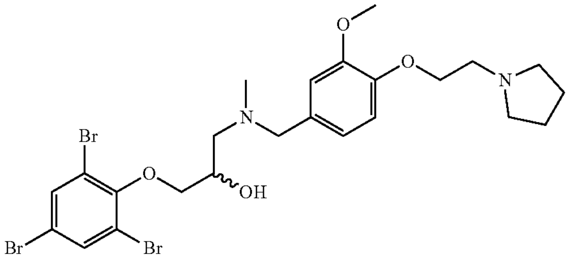 [SMILES: COc1cc(CN(C)CC(O)COc2c(Br)cc(Br)cc2Br)ccc1OCCN1CCCC1]

Compound 5 used is 1-(3-methoxy-4-(2-pyrrolidin-1-yl) ethoxy)phenyl)-N-methylmethanamine (52).

Compound 7 used is 2-((2,4,6-tribromophenoxy)methyl) oxirane 7-22).

White solid, yield 84%, mp: 60-70° C., $^1$H NMR ($CD_3OD$, 400 MHz) δ (ppm): 7.76 (s, 2H), 6.99 (s, 1H), 6.86 (m, 2H), 4.23 (m, 1H), 4.11 (t, J=5.20 Hz, 2H), 3.97 (s, 2H), 3.79 (s, 3H), 3.54 (q, J=12.80 Hz, 2H), 2.94 (t, J=5.60 Hz, 2H), 2.72 (s. 5H), 2.55 (dd, J=12.80, 7.60 Hz, 1H), 2.32 (s, 3H), 1.83 (s, 4H). $^{13}$CNMR (CD3OD, 100 MHz) δ (ppm): 152.74, 149.66, 147.42, 134.96 (2C), 134.96, 131.75, 121.53, 118.54, 117.14, 113.56, 113.07, 75.82, 67.94, 67.68, 62.12, 59.35, 55.01, 54.58, 54.23 (2C), 42.05, 22.83 (2C). IR (KBr, $cm^{-1}$): 3103, 2924, 2873, 2808, 1695, 1597, 1514, 1435, 1371, 1334, 1253, 1138, 1031, 989, 852, 798, 734, 684, 570, HRMS. (ESI): m/z calcd for $C_{24}H_{32}Br_3N_2O_4$ $(M+H)^+$: 648.9912. found: 648.9938.

EMBODIMENT 44 synthesis of 1-(3,4-dichlorophenoxy)-3-((3-methoxy-4-(2-(pyrrolidin-1-yl)ethoxy)benzyl)(methyl) amino)propan-2-ol (CHJ04072)

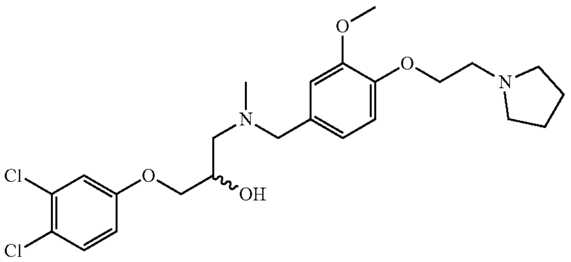 [SMILES: COc1cc(CN(C)CC(O)COc2ccc(Cl)c(Cl)c2)ccc1OCCN1CCCC1]

Compound 5 used is 1-(3-methoxy-4-(2-(pyrrolidin-1-yl) ethoxy)phenyl)-N-methylmethanamine (5-2).

Compound 7 used is 2-((3,4-dichlorophenoxy)methyl) oxirane (7-26).

Colorless oil, yield 85%, $^1$H NMR ($CD_3OD$, 400 MHz) δ (ppm): 7.37 (d, J=8.80 Hz, 1H), 7.06 (s, 1H), 6.96 (s, 1H), 6.85 (m, 3H), 4.11 (t, J=5.20 Hz, 2H), 4.04 (m, 1H) 3.98 (m, 1H), 3.86 (m, 1H), 3.77 (s, 3H), 3.51 (q, J=12.80 Hz, 2H), 2.97 (t, j=5.20 Hz, 2H), 2.76, (s, 4H), 2.61 (dd, J=6.0 Hz, 1H), 2.47 (dd, J=12.80, 6.80 Hz, 1H), 2.32 (s, 3H), 1.85 (s, 4H). $^{13}$CNMR($CD_3OD$, 100 MHz) δ (ppm): 158.36, 149.64, 147.37, 132.25, 131.99, 130.48, 123.32, 121.45, 116.13, 114.57, 113.50, 112.99, 70.96, 67.30, 62.27, 58.73, 54.92, 54.56, 54.24 (2C). 53.40, 42.22, 22.81 (2C), IR (KBr, $cm^{-1}$): 2926, 2875, 2851, 2802, 2361, 2340, 1736, 1651, 1593, 1563, 1512, 1475, 1462, 1418, 1368, 1328, 1284, 1262, 1230, 1127, 1035, 976, 932, 902, 860, 805, 752, 671. HRMS (ESI): m/z calcd for $C_{24}H_{33}Cl_2N_2O_4$ $(M+H)^+$: 483.1817. found: 483.1790.

EMBODIMENT 45 synthesis of 1-(4-bromo-2,6-dichlorophenoxy)-3-((3-methoxy-4-(2-(pyrrolidin-1-yl)ethoxy)benzyl)(methyl)amino)propan-2-ol (CHJ04074)

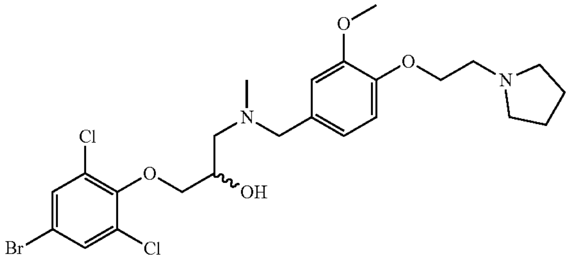 [SMILES: COc1cc(CN(C)CC(O)COc2c(Cl)cc(Br)cc2Cl)ccc1OCCN1CCCC1]

Compound 5 used is 1-(3-methoxy-4-(2-(pyrrolidin-1-yl)ethoxy)phenyl)-N-methylmethanamine (5-2).

Compound 7 used is 2-((4-bromo-2,6-dichlorophenoxy)methyl)oxirane (7-28).

Colorless oil, yield 85%, $^1$H NMR ($CD_3OD$, 400 MHz) δ (ppm): 7.59 (s, 2H), 7.00 (s, 1H), 6.91 (d, J=8.04 Hz, 1H), 6.85 (d, J=8.09 Hz, 1H), 4.16 (m, 3H), 4.00 (m, 2H), 3.81 (s, 3H), 3.56 (d, J=6.47 Hz, 2H), 3.09 (t, J=5.24 Hz, 2H), 2.89 (s, 4H), 2.69 (dd, J=5.54, 4.71 Hz, 1H) 2.57 (dd, J=12.76, 7.5 Hz, 1H), 2.32 (s, 3H), 1.90 (s, 4H). $^{13}$CNMR ($CD_3OD$, 100 MHz) δ (ppm): 150.90, 149.71, 147.19, 131.98, 131.46 (3C), 129.99, 121.53, 116.16, 113.92, 113.01, 76.00, 67.88, 67.09, 62.06, 59.18, 54.95, 54.44, 54.23 (2C), 41.93, 22.75 (2C). IR (KBr, cm−1): 2953, 2920, 2866, 2765, 1726, 1651, 1593, 1516, 1458, 1419, 1373, 1327, 1261, 1230, 1136, 1085, 1028, 964, 875, 842, 800, 752, 557. HRMS (ESI): m/z calcd for $C_{24}H_{32}BrCl_2N_2O_4$ $(M+H)^+$: 561.0923. found: 561.0882.

EMBODIMENT 46 synthesis of 1-(3-bromo-5-chlorophenoxy)-3-((3-methoxy-4-(2-(pyrrolidin-1-yl)ethoxy)benzyl)methyl)aminopropan-2-ol (CHJ04075)

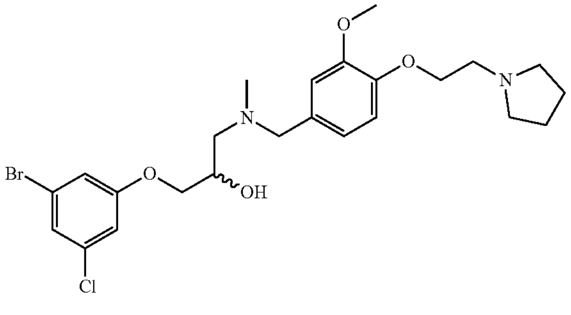

Compound 5 used is 1-(3-methoxy-4-(2-pyrrolidin-1-yl)ethoxy)phenyl)-N-methylmethanamine (5-2).

Compound 7 used is 2-((3-bromo-5-chlorophenoxy)methyl)oxirane (7-29).

Colorless oil, yield 87%, $^1$H NMR ($CD_3OD$, 400 MHz) δ (ppm); 7.13 (s, 1H), 7.03 (s, 1H), 6.98 (s, 1H), 6.90 (m, 2H), 6.82 (d, J=8.07 Hz, 1H), 4.15 (t, J=5.54 Hz, 2H), 4.03 (m, 2H), 3.88 (m, 1H), 3.80 (s, 3H), 3.52 (q, J=12.86 Hz, 2H), 3.12 (t, J=5.24 Hz, 2H), 2.92 (s, 4H), 2.62 (dd, J=12.72, 6.12 Hz, 1H), 2.48 (dd, J=12.71, 6.44 Hz, 1H), 2.33 (s, 3H), 1.91 (s, 4H), $^{13}$CNMR ($CD_{36}l$ OD, 100 MHz) δ (ppm): 160.38, 149.69, 147.13, 135.27, 132.25, 123.18, 122.49, 121.48, 116.32, 113.84 (2C), 112.93, 70.99, 67.18, 62.23, 58.61, 54.94, 54.42, 54.25 (2C), 42.19, 22.74 (2C), 12.54. IR (KBr, $cm^{-1}$): 2974, 2934, 2379, 2309, 1716, 1651, 1593, 1557, 1539, 1510, 1475, 1419, 1393, 1339, 1231, 1124, 1038, 854, 670, 520. HRMS (ESI): m/z calcd for $C_{24}H_{33}BrClN_2O_4$ $(M+H)^+$: 527.1312. found: 527.1275.

EMBODIMENT 47 synthesis of 1-((4-(2-(diethylamino)ethoxy)-3-methoxybenzyl)(methyl)amino)-3-(2-isopropylphenoxy)propan-2-ol (CHJ04089)

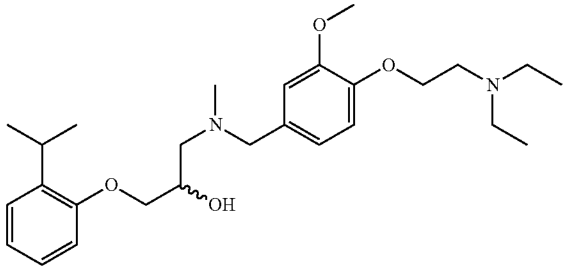 [SMILES: CCN(CC)CCOc1ccc(CN(C)CC(O)COc2ccccc2C(C)C)cc1OC]

Compound 5 used is N,N-diethyl-2-(2-methoxy-4-((methylamino)methyl)phenoxy)ethan-1-amine 5-3).

Compound 7 used is 2-((2-isopropylphenoxy)methyl)oxirane (7-7).

Colorless oil, yield 82%, $^1$H NMR ($CDCl_3$, 400 MHz) δ (ppm): 7.20 (d, J=7.60 Hz, 1H), 7.13 (t, J=8.0 Hz, 1H), 6.93 (t, J=07.20 Hz, 1H), 6.82 (m, 4H), 4.11 (m, 3H), 3.98 (m, 2H), 3.84 (s, 3H), 3.65 (d, J=12.80 Hz, 1H), 3.46 (d, J=12.80 Hz, 1H), 3.26 (m, 1H), 2.94 (t, J=6.80 Hz, 2H), 2.66 (m, 5H), 2.54 (m, 1H), 2.31 (s, 3H), 1.20 (d, J=7.20 Hz, 6H), 1.08 (t, J=7.20 Hz, 6H). $^{13}$CNMR($CDCl_3$, 100 MHz) δ (ppm): 155.82, 149.38, 147.59, 137.05, 131.20, 126.55, 126.07, 121.26, 120.89, 112.69, 112.41, 111.30, 70.35, 67.24, 66.34, 62.47, 59.66, 55.94, 51.66, 47.85 (2C), 42.36, 26.89, 22.63 (2C), 11.78 (2C). IR (KBr, cm−1): 3035, 2965, 2933, 2871, 2360, 1598, 1513, 1491, 1451, 1417, 1368, 1286, 1261, 1239, 1197, 1139, 1088, 1034, 983, 938, 881, 823, 751. HRMS (ESI): m/z calcd for $C_{27}H_{43}N_2O_4$ $(M+H)^+$: 459.3223. found: 459.3166.

EMBODIMENT 48 synthesis of 1-(2-bromo-5-(trifluoromethyl)phenoxy)-3-((4-(2-(diethylamino)ethoxy)-3-methoxy benzyl)(methyl)amino)propan-2-ol (CHJ04090)

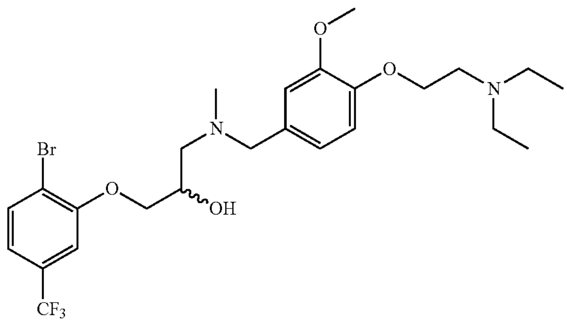 [SMILES: CCN(CC)CCOc1ccc(CN(C)CC(O)COc2cc(C(F)(F)F)ccc2Br)cc1OC]

Compound 5 used is N,N-diethyl-2-(2-methoxy-4-((methylamino)methyl)phenoxy)ethan-1-amine (5-3).

Compound 7 used is 2-((2-bromo-5-(trifluoromethyl)phenoxy)methyl)oxirane (7-19).

Colorless oil, yield 81%, $^1$H NMR ($CDCl_3$, 400 MHz) δ (ppm): 7.63 (d, J=8.40 Hz, 1H), 7.10 (m, 2H), 6.81 (m, 3H), 4.11 (m, 5H), 3.84 (s, 3H), 3.65 (d, J=12.80 Hz, 1H), 3.47 (d, J=13.20 Hz, 1H), 2.94 (t, J=6.80 Hz, 2H), 2.67 (m, 5H), 2.55 (m, 1H) 2.32 (s, 3H), 1.08 (t, J=7.20 Hz, 6H). $^{13}$CNMR ($CDCl_3$, 100 MHz) δ (ppm): 155.44, 149.39, 147.63, 133.70 (2C), 131.09, 121.31 (2C), 118.73, 116.43, 112.73, 112.45, 109.89, 71.63, 67.28, 66.10, 62.48, 58.95, 55.94, 51.65, 47.85 (2C), 42.42, 11.77 (2C). IR (KBr, $cm^{-1}$): 2969, 2936, 2876, 2837, 2360, 2340, 1651, 1597, 1539, 1512, 1488, 1461, 1420, 1329, 1296, 1263, 1231, 1169, 1128, 1081, 1036, 979, 934, 857, 814, 751, 656, 565. HRMS (ESI): m/z calcd for $C_{25}H_{35}BrF_3N_2O_4$ $(M+H)^+$: 563.1676. found: 563.1676.

EMBODIMENT 49 synthesis of 1-(3,4-dichlorophenoxy)-3-((4-(2-(diethylamino)ethoxy)-3-methoxybenzyl)(methyl)amino)propan-2-ol (CHJ04091)

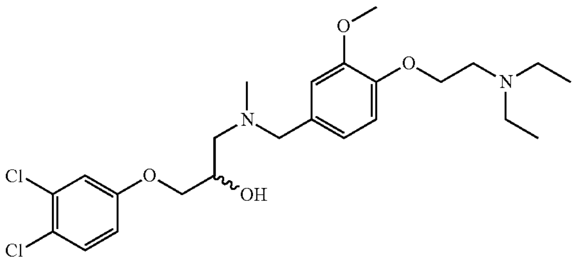 [SMILES: CCN(CC)CCOc1ccc(CN(C)CC(O)COc2ccc(Cl)c(Cl)c2)cc1OC]

Compound 5 used is N,N-diethyl-2-(2-methoxy-4-((methylamino)methyl)phenoxy)ethan-1-amine (5-3).

Compound 7 used is 2-((3,4-dichlorophenoxy)methyl) oxirane (7-26).

Colorless oil, yield 85%, $^1$H NMR ($CDCl_3$, 400 MHz) δ (ppm): 7.31 (d, J=8.8 Hz, 1H), 7.00 (s, 1H), 6.80 (m, 4H), 4.09 (m, 3H), 3.91 (m, 2H), 3.85 (s, 3H), 3.62 (d, J=12.80 Hz, 1H), 3.45 (d, J=12.80 Hz, 1H), 2.95 (t, J=6.40 Hz, 2H), 2.67 (m, 5H), 2.47 (m, 1H), 2.29 (s, 3H), 1.08 (t, J=7.20 Hz, 6H). $^{13}$CNMR($CDCl_3$, 100 MHz) δ (ppm): 157.83, 149.37, 147.63, 132.81, 131.03, 130.65, 124.20, 121.31, 116.45, 114.63, 112.73, 112.46, 70.97, 67.20, 65.97, 62.37, 59.08, 55.96, 51.65, 47.80 (2C), 42.28, 11.70 (2C). IR (KBr, cm−1): 2970, 2936, 2874, 2832, 2360, 2326, 1700, 1651, 1593, 1559, 1539, 1511, 1475, 1459, 1418, 1337, 1285, 1263, 1230, 1158, 1126, 1090, 1126, 1035, 930, 865, 806, 671. HRMS (ESI): m/z calcd for $C_{24}H_{35}Cl_2N_2O_4$ $(M+H)^+$: 485.1974. found: 485.1904.

EMBODIMENT 50 synthesis of 1-(3-bromo-4-fluorophenoxy)-3-((4-(2-(diethylamino)ethoxy)-3-methoxybenzyl)(methyl) amino)propan-2-ol (CHJ04092)

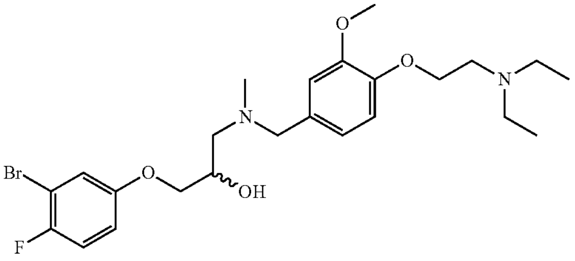

Compound 5 used is N,N-diethyl-2-(2-methoxy-4-((methylamino)methyl)phenoxy)ethan-1-amine (5-3).

Compound 7 used is 2-((3-bromo-4-fluorophenoxy) methyl)oxirane (7-21).

Colorless oil, yield 82%, $^1$H NMR ($CDCl_3$, 400 MHz) δ (ppm): 7.09 (m, 1H), 7.02 (t, J=8.80 Hz, 1H), 6.81 (m, 4H), 4.09 (m, 3H), 3.90 (m, 2H), 3.85 (s, 3H), 3.62 (d, J=12.80 Hz, 1H), 3.46 (d, J=12.80 Hz, 1H), 2.95 (t, J=7.20 Hz, 2H), 2.67 (m, 5H), 2.47 (m, 1H), 2.29 (s, 3H), 1.09 (t, J=7.20 Hz, 6H). $^{13}$CNMR($CDCl_3$, 100 MHz) δ (ppm): 155.25, 149.38, 147.62, 131.06, 121.3 (2C), 119.02 (2C), 116.52, 114.98, 112.58, 109.01, 71.29, 67.19, 66.04, 62.37, 59.14, 55.96, 51.64, 47.80 (2C), 42.27, 11.69 (2C). IR (KBr, $cm^{-1}$): 2969, 2936, 2875, 2832, 2360, 2340, 1651, 1592, 1556, 1539, 1511, 1493, 1459, 1418, 1373, 1333, 1262, 1220, 1203, 1158, 1139, 1092, 1036, 929, 864, 805, 752. HRMS (ESI): m/z calcd for $C_{24}H_{35}BrFN_2O_4$ $(M+H)^+$: 513.1764. found: 513.1710.

EMBODIMENT 51 synthesis of 1-(4-bromo-3-(trifluoromethyl)phenoxy)-3-((4-(2-(diethylamino)ethoxy)-3-methoxybenzyl)(methyl)amino)propan-2-ol (CHJ04093)

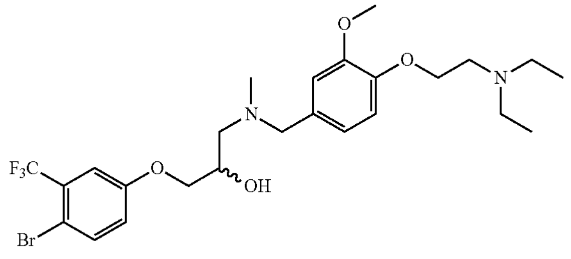 [SMILES: CCN(CC)CCOc1ccc(CN(C)CC(O)COc2ccc(Br)c(C(F)(F)F)c2)cc1OC]

Compound 5 used is N,N-diethyl-2-(2-methoxy-4-((methylamino)methyl)phenoxy)ethan-1-amine (5-3).

Compound 7 used is 2-((4-bromo-3-(trifluoromethyl)phenoxy)methyl)oxirane (7-3).

Colorless oil, yield 83%, $^1$H NMR ($CDCl_3$400 MHz) δ (ppm): 7.57 (d, J=8.80 Hz, 1H), 7.24 (s, 1H), 6.92 (d, J=8.80 Hz, 1H), 6.82 (m, 3H), 4.11 (t, J=6.40 Hz, 3H), 3.96 (m, 2H) 3.84 (s, 3H), 3.63 (d, J=12.80 Hz, 1H), 3.46 (d, J=12.80 Hz, 1H), 2.97 (t, J=6.4 Hz, 2H), 2.67 (m, 5H), 2.48 (m, 1H), 2.30 (s, 3H), 1.10 (t, J=7.20 Hz, 6H), $^{13}$CNMR($CDCl_3$, 100 MHz) δ (ppm): 157.82, 149.40, 147.62, 135.72 (2C), 131.02, 121.32 (2C), 118.88 (2C), 114.64, 112.77, 110.18, 71.29, 67.19, 66.04, 62.37, 59.14, 55.96, 51.64, 47.80 (2C), 42.27, 11.69 (2C). IR (KBr, $cm^{-1}$): 2969, 2936, 2875, 2800, 2360, 2340, 1603, 1512, 1475, 1462, 1419, 1373, 1330, 1313, 1260, 1233, 1171, 1139, 1097, 1036, 1017, 980, 932, 880, 810, 752, 702. HRMS (ESI): m/z calcd for $C_{25}H_{35}BrF_3N_2O_4$ $(M+H)^+$: 563.1732. found: 563.1695.

EMBODIMENT 52 synthesis of 1-(4-bromo-2,6-dichlorophenoxy)-3-((4-(2-(diethylamino)ethoxy)-3-methoxybenzyl)(methyl)amino)propan-2-ol (CHJ04094)

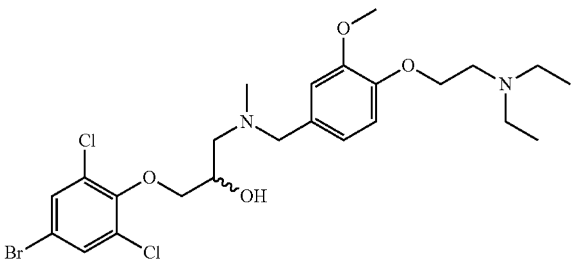 [SMILES: CCN(CC)CCOc1ccc(CN(C)CC(O)COc2c(Cl)cc(Br)cc2Cl)cc1OC]

Compound 5 used is N,N-diethyl-2-(2-methoxy-4-((methylamino)methyl)phenoxy)ethan-1-amine (5-3).

Compound 7 used is 2-((4-bromo-2,6-dichlorophenoxy)methyl)oxirane (7-28).

Colorless oil, yield 87%, $^1$H NMR ($CDCl_3$, 400 MHz) δ (ppm): 7.44 (s, 2H), 6.81 (m, 3H), 4.06 (m, 5H), 3.84 (s, 3H), 3.61 (d, J=12.80 Hz, 1H), 3.49 (d, J=12.80 Hz, 1H), 2.96 (t, J=6.80 Hz, 2H), 2.69 (m, 5H), 2.59 (m, 1H), 2.28 (s, 3H), 1.09 (t, J=7.20 Hz, 6H). $^{13}$CNMR($CDCl_3$, 100 MHz) δ (ppm): 150.74, 149.36, 147.52, 131.62 (3C), 131.24, 130.16, 121.30, 116.51, 112.76, 112.45, 71.29, 67.19, 66.04, 62.37, 59.14, 55.96, 51.64, 47.80 (2C), 42.27, 11.69 (2C). IR, (KBr, $cm^{-1}$): 2966, 2935, 2875, 2800, 2362, 2340, 1597, 1548, 1514, 1456, 1375, 1328, 1261, 1134, 1031, 995, 929, 854, 802, 748, 702, 569. HRMS (ESI): m/z calcd for $C_{24}H_{34}BrCl_2N_2O_4$ $(M+H)^+$: 563.1079. found: 563.1039.

EMBODIMENT 53 synthesis of 1-((4-(2-(1H-imidazol-1-yl)ethoxy)-3-methoxybenzyl)(methyl)amino)-3-(4-bromo-3-(trifluoromethyl)phenoxy)propan-ol (CHJ04097)

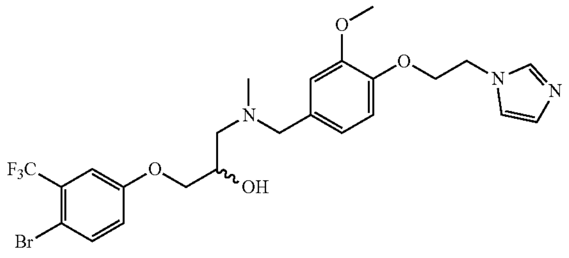 [SMILES: COc1cc(CN(C)CC(O)COc2ccc(Br)c(C(F)(F)F)c2)ccc1OCCn1ccnc1]

Compound 5 used is 1-(4-(2-(1H-imidazol-1-yl)ethoxy)-3-methoxyphenyl)-N-methylmethanamine (5-4).

Compound 7 used is 2-((4-bromo-3-(trifluoromethyl)phenoxy)methyl)oxirane. (7-3).

White solid, yield 85%, $^1$H NMR ($CDCl_3$, 400 MHz) δ (ppm): 7.64 (s, 1H), 7.56 (d, J=8.80 Hz, 1H), 7.23 (s, 1H), 7.10 (s, 1H), 7.05 (s, 1H), 6.92 (d, J=8.8 Hz, 1H), 6.84 (s, 1H), 6.74 (m, 2H) 4.34 (m, 2H), 4.24 (m, 2H), 4.10 (m 1H), 3.96 (m, 2H), 3.84 (s, 3H), 3.62 (d, J=12.80 Hz, 1H), 3.46 (d, J=12.80 Hz, 1H), 2.62 (t, J=11.20 Hz, 1H), 2.49 (m, 1H), 2.30 (s, 3H). $^{13}$CNMR($CDCl_3$, 100 MHz) δ (ppm): 157.80, 149.88, 146.88, 137.64, 135.73, 132.45, 130.69, 129.26, 121.25, 119.59, 118.87, 114.63, 114.58, 114.18, 112.82, 110.21, 70.88, 68.92, 66.00, 62.35, 59.07, 55.95, 46.69, 42.35. IR (KB, $cm^{-1}$): 3111, 2929, 2877, 2787, 2362, 2340, 1600, 1514, 1473, 1419, 1321, 1261, 1230, 1170, 1138, 1093, 1026, 962, 908, 871, 810, 759, 663. HRMS (ESI): m/z calcd for $C_{24}H_{28}BrF_3N_3O_4$ $(M+H)^+$: 558.1215. found: 558.1172.

EMBODIMENT 54 synthesis of 1-((4-(2-(1H-imidazol-1-yl)ethoxy)-3-methoxybenzyl)(methyl)amino)-3-(2-bromo-5-(trifluoromethyl)phenoxy)propan-2-ol (CHJ04099)

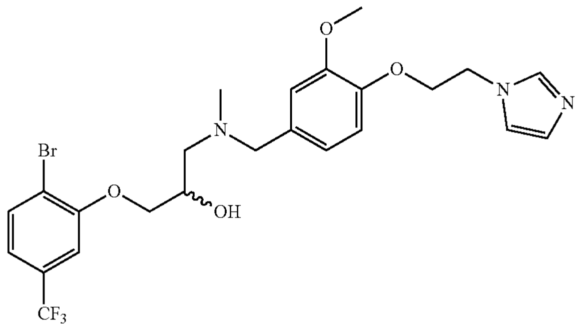 [SMILES: COc1cc(CN(C)CC(O)COc2cc(C(F)(F)F)ccc2Br)ccc1OCCn1ccnc1]

Compound 5 used is 1-(4-(2-(1H-imidazol-1-yl)ethoxy)-3-methoxyphenyl)-N-methylmethanamine (5-4).

Compound 7 used is 2-((2-bromo-5-(trifluormethyl)phenoxy)methyl)oxirane (7-19)

White solid, yield 90%, $^1$H NMR ($CDCl^3$, 400 MHz) δ (ppm): 7.62 (d, J=12.40 Hz, 2H), 7.08 (m, 4H), 6.85 (s, 1H), 6.78 (d, J=8.0 Hz, 1H), 6.71 (d, J=8.0 Hz, 1H), 4.34 (m, 2H), 4.23 (m, 2H), 4.09 (m, 3H), 3.83 (s, 3H), 3.64 (d, J=12.80 Hz, 1H), 3.47 (d. J=13.20 Hz, 1H), 2.73 (t, J=11.60 Hz, 1H), 2.55 (m, 1H), 2.32 (s, 3H). $^{13}$CNMR(CDCl$_3$, 100 MHz) δ (ppm): 155.41, 149.90, 146.85, 137.67, 133.71, 132.57, 130.71, 129.39, 122.28, 121.25, 119.58, 118.81, 116.41, 114.19, 112.80, 109.89, 71.55, 68.94, 66.15, 62.45, 58.93, 55.94, 46.65, 42.52. IR (KBr, cm$^{-1}$): 3118, 2879, 2845, 2787, 2362, 2340, 1676, 1595, 1516, 1460, 1421, 1388, 1332, 1290, 1259, 1138, 1114, 1085, 1029, 964, 906, 819, 752. HRMS (ESI): m/z calcd for $C_{24}H_{28}BrF_3N_3O_4$ $(M+H)^+$: 558.1215. found: 558.1160.

EMBODIMENT 55 synthesis of 1-((4-(2-(1H-imidazol-1-yl)ethoxy)-3-methoxybenzyl)(methyl)amino-3-(4-bromophenoxy) propan-2-ol (CHJ05001)

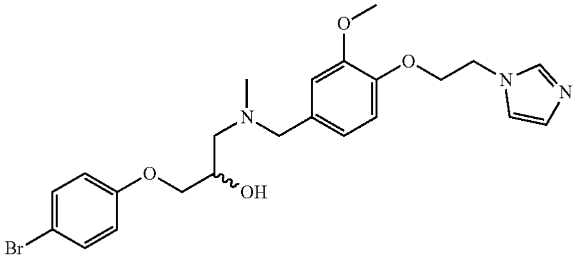 [SMILES: COc1cc(CN(C)CC(O)COc2ccc(Br)cc2)ccc1OCCn1ccnc1]

Compound 5 used is 1-(4-(2-(1H-imidazol-1-yl)ethoxy)-3-methoxyphenyl)-N-methylmethanamine (5-4).

Compound 7 used is 2-((4-bromophenoxy)methyl)oxirane (7-12).

White solid, yield 85%, $^1$H NMR (CDCl$_3$, 400 MHz) δ (ppm): 7.63 (s, 1H) 7.35 (d, J=8.40 Hz, 2H), 7.08 (d, J=14.80 Hz, 2H), 6.78 (m, 5H), 4.34 (m, 2H), 4.23 (m, 2H), 4.09 (m, 1H), 3.92 (d, J=4.40 Hz, 2H), 3.83 (s, 3H), 3.61 (d, J=13.20 Hz, 1H), 3.45 (d, J=12.80 Hz, 1H), 2.62 (t, J=11.60 Hz, 1H), 2.49 (m, 1H), 2.29 (s, 3H). $^{13}$CNMR(CDCl$_3$, 100 MHz) δ (ppm): 157.89, 149.88, 146.84, 137.67, 132.56, 132.24 (2C), 129.38, 121.23, 119.58, 116.36 (2C), 114.19, 113.12, 112.81, 70.60, 68.95, 66.12, 62.34, 59.31, 55.96, 46.65, 42.34. IR (KBr, cm$^{-1}$): 3111, 2931, 2879, 2843, 2771, 2362, 2340, 1712, 1587, 1514, 1487, 1456, 1419, 1355, 1325, 1242, 1139, 1099, 1064, 1028, 999, 960, 910, 883, 858, 819, 754, 692, 663, 615. HRMS (ESI): m/z calcd for $C_{23}H_{29}BrN_3O_4$ $(M+H)^+$: 490.1341. found: 490.1341.

EMBODIMENT 56 synthesis of 1-((4-(2-(1H-imidazol-1-yl)ethoxy)-3-methoxybenzyl)(methyl)amino)-3-(3-bromo-4-methylphenoxy)propan-2-ol (CHJ05002)

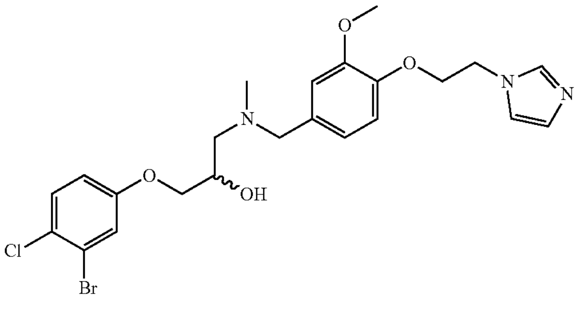 [SMILES: COc1cc(CN(C)CC(O)COc2ccc(Cl)c(Br)c2)ccc1OCCn1ccnc1]

Compound 5 used is 1-(4-(2-(1H-imidazol-1-yl)ethoxy)-3-methoxyphenyl)-N-methylmethanamine (5-4).

Compound 7 used is 2-((3-bromo-4-chlorophenoxy) methyl)oxirane (7-17).

White solid, yield 90%, $^1$H NMR (CDCl$_3$, 400 MHz) δ (ppm): 7.63 (s, 1H), 7.30 (d, J=8.80 Hz, 1H), 7.16 (s, 1H), 7.08 (d, J=16.0 Hz, 2H), 6.78 (m, 4H) 4.34 (m, 2H), 4.23 (m 2H) 4.09 (m, 1H), 3.92 (m, 2H), 3.84 (s, 3H), 3.61 (d, J=13.2 Hz, 1H), 3.45 (d, J=13.2 Hz, 1H), 2.61 (t, J=11.60 Hz, 1H), 2.48 (m, 1H), 2.29 (s, 3H). $^{13}$CNMR(CDCl$_3$, 100 MHz) δ (ppm): 157.73, 1.49.89, 146.87, 137.67, 132.50, 130.48, 129.37, 126.16, 122.52, 121.24, 119.55 (2C), 115.30, 114.19, 112.81, 70.74, 68.95, 66.04, 62.35, 59.12, 55.97, 46.66, 42.37. IR (KBr, cm−1): 3113, 2927, 2877, 2845, 2785, 2362, 2340, 1589, 1564, 1512, 1467, 1419, 1384, 1323, 1261, 1239, 1141, 1089, 1029, 960, 906, 858, 808, 754, 666. HRMS (ESI): m/z calcd for $C_{23}H_{28}BrClN_3O_4$ $(M+H)^+$: 524.0952. found: 524.0916.

EMBODIMENT 57 synthesis of 1-((4-(2-(1H-imidazol-1-yl)ethoxy)-3-methoxybenzyl)(methyl)amino)-3-(3-bromo-4-methylphenoxy)propan-2-ol (CHJ05003)

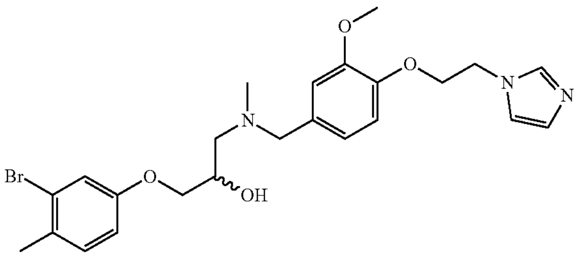 [SMILES: COc1cc(CN(C)CC(O)COc2ccc(C)c(Br)c2)ccc1OCCn1ccnc1]

Compound 5 used is 1-(4-(2-(1H-imidazol-1-yl)ethoxy)-3-methoxyphenyl)-N-methylmethanamine (5-4).

Compound 7 used is 2-((3-bromo-4-methylphenoxy) methyl)oxirane (7-18).

White solid, yield 90%, $^1$H NMR CDCl$_3$, 400 MHz) δ (ppm): 7.64 (s, 1H), 7.10 (s, 3H), 7.06 (s, 1H), 6.86 (s, 1H), 6.73 (m, 3H), 4.34 (m, 2H), 4.24 (m, 2H), 4.09 (m, 1H), 3.92 (m, 2H), 3.84 S, 3H), 3.61 (d, J=12.80 Hz, 1H), 3.46 (d, J=13.20 Hz, 1H), 2.62 (t, J=12.0 Hz, 1H), 2.48 (m, 1H), 2.30 (d, J=10.40 Hz, 6H), $^{13}$CNMR($CDCl_3$, 100 MHz) δ (ppm): 157.34, 149.86, 146.83, 137.67, 132.49, 130.99, 130.04, 129.37, 124.80, 121.24, 119.60, 118.30, 114.15, 113.90, 112.77, 70.68, 68.93, 66.11, 62.33, 59.30, 55.96, 46.64, 42.30, 21.84. IR (KBr, cm−1): 3112, 2924, 2877, 2844, 2777, 2361, 2340, 1605, 1564, 1511, 1492, 1454, 1418, 1264, 1239, 1226, 1158, 1141, 1091, 1029, 962, 896, 866, 815, 800, 764, 739, 658, 614. HRMS (ESI): m/z calcd for $C_{24}H_{31}BrN_3O_4$ $(M+H)^+$: 504.1498. found: 504.1460.

EMBODIMENT 58 synthesis of 1-((4-(2-(1H-imidazol-1-yl)ethoxy)-3-methoxybenzyl)(methyl)amino)-3-(3-5-chlorophenoxy)propan-2-ol (CHJ05004)

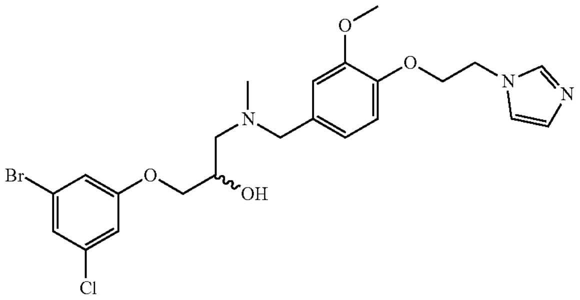 [SMILES: COc1cc(CN(C)CC(O)COc2cc(Cl)cc(Br)c2)ccc1OCCn1ccnc1]

Compound 5 used is 1-(4-(2-(1H-imidazol-1-yl)ethoxy)-3-methoxyphenyl)-N-methylmethanamine (5-4).

Compound 7 used is 2-((3-bromo-5-chlorophenoxy) methyl)oxirane (7-29).

White solid, yield 88%, $^1$H NMR ($CDCl_3$, 400 MHz) δ (ppm): 7.63 (s, 1H), 7.10 (s, 2H), 7.06 (s, 1H), 6.96 (s, 1H) 6.84 (s, 2H), 6.73 (m, 2H), 4.35 (m, 2H), 4.24 (m, 2H) 4.07 (m, 1H) 3.93 (m, 2H), 3.84 (s, 3H), 3.61 (d, J=12.94 Hz, 1H), 3.45 (d, J=13.35 Hz, 1H), 2.60 (t, J=11.55 Hz, 1H), 2.47 (m, 1H), 2.29 (s, 3H). $^{13}$CNMR($CDCl_3$, 100 MHz) δ (ppm): 159.85, 149.91, 146.89, 137.67, 135.53, 132.46, 129.39, 124.03, 122.83, 121.24, 119.58, 116.57, 114.21 (2C), 112.79, 70.90, 68.95, 65.96, 62.35, 59.05, 55.97, 46.66, 42.37. HRMS (ESI): m/z calcd for $C_{23}H_{28}BrClN_3O_4$ $(M+H)^+$:524.0952. found: 524.0913.

Experiment on Compounds in the Invention in Inhibiting the Activity of Tumor Cell Growth

1 Experiment Materials

Dissolve CHJ compound series with dimethyl sulfoxide (DMSO, final concentration 0.4%), and use RPMI-1640 culture medium containing 15% fetal calf serum to prepare 1 mg/mL solution for future use. During drug administration in groups, use the culture medium to dilute it to the concentration needed.

Experiment reagent

| Reagent name | Specification | Manufacturer |
|---|---|---|
| Cis-platinum | 10 mg/bottle | Qilu Pharmaceutical Co., Ltd. |

-continued

Experiment reagent

| Reagent name | Specification | Manufacturer |
|---|---|---|
| DMEM (High Glucose) | 500 mL | Biological Industries in Isreal |
| Fetal calf serum | 500 mL | Biological Industries in Isreal |
| Dimethyl sulfoxide | 50 mL | Beijing Solarbio Life Sciences Co., Ltd.: |
| MTT | 5 mL | Sigma in America |
| EDTA pancreatic enzyme | 100 mL | Beijing Solarbio Life Sciences Co., Ltd.: |

Cell lines: human lung cancer (A549), Inman ovarian cancer (SKOV3), human melanoma (A375) and human colon cancer (LOVO) cell lines, all purchased from the Cell Bank of the Chinese Academy of Sciences, DMEM containing 15% fetal bovine serum (High Glucose) culture medium, placed in a 37° C., 5% CO2 incubator.

2. Experimental Methods

MTT is an oxidizing yellow dye with the chemical name of 3-(4,5-dimethyl-2-thiazolyl)-2,5-diphenyl-2-H-tetrazoliumbromide tetrazole bromide. The MMT method, also known as the MTT colorimetric method, can test the survival and growth of cells. The method is simple and easily accessible and often used to screen the substance with cytotoxic activity. The basic principle of testing, is that succinodehydrogenase can reduce exogenous MIT so that MTT is reduced to blueviolet crystal Formazan insoluble to water. The crystal deposits in cells. The succinodehydrogenase exists in the mitochondria of living cells, not in the dead cells. Therefore, the chromogenic reaction can only take place in living cells. Then, dissolve the blueviolet crystal Formazan contained in cells with dimethyl sulfoxide (DMSO), and measure its absorbency with microplate reader so that the count of living cells is reflected indirectly. Within the scope of certain cell count, the amount of blueviolet crystal Formazan formed is positively correlated to the count of living cells.

MTT is efficient, accurate, convenient, economical and highly repeatable. It has been extensively applied to the screening of antitumor drugs, activity detection of medical bioactive factor, cytotoxic activity test, and the measurement of tumor radiosensitivity.

Preparation of 5 mg/mL MTT solution: weigh 500.0 mg MTT powder and dissolve it in 100 ml warm PBS. Use the millipore filter of 0.22 μm aperture to screen the bacteria and obtain the filtrate. Divide the filtrate into small doses and put them the centrifugal tube which has gone through autoclaved sterilization. Freeze them in a dark place under −20° C.

Fetch the frozen tube containing the tumor cells from liquid nitrogen and put it swiftly into the 37° C. incubator. Keep shaking till it melts. Rub the rim of the cover of frozen tube with 75% alcohol, suck in the cell suspension and transfer it to 10 mL centrifugal tube. Add 5 ml culture medium. Apply low-speed centrifugation (25° C. 3000 r/min, 5 min), discard the supernatant, add culture medium, and then repeat the centrifugation once more. After proper amount of culture medium is added for the purpose of dilution, blow away the cells with straw to form suspension. Transfer the suspension to the culture bottle, and place the bottle in the 37° C. cell incubator containing 5% $CO_2$.

Change the culture solution the next day and place the bottle in the 37° C. cell incubator containing 5% $CO^2$ for continued culture.

Human lung cancer (A549), human ovarian cancer (SKOV3), human melanoma (A375) and human colon cancer (LOVO) cells are all adherent. Based on the growth rate of tumor cells, wash the adherent tumor cells in the logarithmic phase and digest them in 0.25% EDTA pancreatic enzyme. Adjust the cell count to 1×105/mL and inoculate the cells in 96-pore plate, each pore containing 100 μL. Culture the cells in the 37° C. $CO_2$ incubator, and administer the drug 24 h later. Add pharmaceutical (CJH compound series) of different concentrations to the administration group. Set up 5 dosage groups for each pharmaceutical, respectively 100, 10, 1, 0.1, 0.01 μmol/L. Set up three complex pores for each concentration. Set up blank control, DMSO (0.8%) solvent control and cis-platinum positive control. After 48 h of culture in the 37° C. incubator containing 5% $CO_2$, measure the OD value through MTT method and calculate the cell inhibition ratio.

2.3 Calculation of $IC_{50}$

After 48 h of culture of human lung cancer (A549), human ovarian cancer (SKOV3), human melanoma (A375) and human colon cancer (LOVO) cells, stop it and add 10 μL 0.5% MTT solution to each pore. Place it in the $CO_2$ incubator for 4 h. Remove the liquid from each pore, respectively add 0.2 mL DMSO solution, and oscillate it adequately on the table concentrator under low frequency so that the blueviolet crystal Formazan is dissolved adequately. Place it in the microplate reader and record the OD value at the wavelength of 490 mm. Calculate the average OD value of three parallel pores of different concentrations, and calculate the cell inhibition ratio and $IC_{50}$ of each tested pharmaceutical under different concentrations based on the average.

Inhibition ratio (%)=[1-tested sample OD/negative control group OD]×100%.

$IC_{50}$ value of target compound against cancer cell proliferation

| | $IC_{50}$ (μM) | | | |
|---|---|---|---|---|
| Compound | A549 | SKOV3 | A375 | LOVO |
| SAMS10 | 14.64 ± 0.06 | 21.07 ± 0.18 | 27.11 ± 0.66 | 8.48 ± 0.07 |
| CHJ02029 | 3.55 ± 0.06 | 6.30 ± 0.16 | 2.43 ± 0.12 | 1.87 ± 0.02 |
| CHJ02049 | 0.52 ± 0.23 | 0.62 ± 0.08 | 0.62 ± 0.04 | 1.25 ± 0.03 |
| CHJ02050 | 1.09 ± 1.55 | 4.04 ± 0.06 | 1.87 ± 0.07 | 3.88 ± 1.80 |
| CHJ03001 | 1.30 ± 1.03 | 2.48 ± 10.63 | 1.95 ± 0.33 | 1.26 ± 0.53 |
| CHJ03003 | 6.08 ± 0.90 | 3.00 ± 0.99 | 5.95 ± 0.42 | 0.70 ± 0.26 |
| CHJ03004 | 2.10 ± 1.25 | 6.19 ± 0.25 | 0.72 ± 0.80 | 2.54 ± 0.10 |
| CHJ03005 | 15.58 ± 0.16 | 3.99 ± 0.21 | 5.60 ± 0.81 | 6.66 ± 0.11 |
| CHJ03011 | 10.56 ± 0.02 | 21.21 ± 1.08 | 1.82 ± 1.23 | 15.19 ± 1.78 |
| CHJ03012 | 2.19 ± 1.04 | 3.54 ± 1.02 | 0.16 ± 0.33 | 1.95 ± 0.43 |
| CHJ03014 | 1.09 ± 0.06 | 6.19 ± 0.62 | 1.63 ± 0,72 | 0.53 ± 0.15 |
| CHJ03015 | 1.03 ± 0.13 | 4.47 ± 1.62 | 3.22 ± 0,42 | 0.55 ± 0.21 |
| CHJ03017 | 17.25 ± 0.79 | 6.21 ± 1.04 | 8.68 ± 0.11 | 2.44 ± 0.03 |
| CHJ03018 | 18.76 ± 1.06 | 1.79 ± 0.23 | 3.13 ± 0.06 | 1.72 ± 1.58 |
| CHJ03043 | 2.50 ± 1.32 | 2.90 ± 0.19 | 0.54 ± 0.26 | 0.95 ± 0.41 |
| CHJ04010 | 4.51 ± 1,29 | 4.96 ± 1.26 | 0.45 ± 0.46 | 2.78 ± 0.23 |
| CHJ04011 | 4.05 ± 1.12 | 2.41 ± 1.03 | 0.48 ± 0.28 | 1.01 ± 0.08 |
| CHJ04012 | 6.38 ± 0.07 | 4.34 ± 0.32 | 1.24 ± 1.01 | 2.12 ± 0.04 |
| CHJ04020 | 1.38 ± 1.14 | 3.40 ± 1.17 | 1.60 ± 0.92 | 3.83 ± 1.80 |
| CHJ04022 | 1.88 ± 0.19 | 1.03 ± 0.24 | 0.05 ± 0.01 | 0.69 ± 0.03 |
| CHJ04023 | 5.44 ± 2.54 | 8.03 ± 2.77 | 0.81 ± 0.33 | 3.07 ± 1.62 |
| CHJ04024 | 5.45 ± 1.03 | 1.37 ± 0.34 | 0.98 ± 0.76 | 18.61 ± 3.22 |
| CHJ04025 | 4.21 ± 2.24 | 3.32 ± 1.02 | 2.34 ± 1.63 | 2.55 ± 1.65 |
| CHJ04026 | 0.97 ± 0.21 | 7.45 ± 2.26 | 1.50 ± 0.06 | 0.82 ± 0.42 |
| CHJ04027 | 6.22 ± 1.34 | 3.02 ± 1.76 | 0.73 ± 0.13 | 2.35 ± 1.04 |
| CHJ04033 | 0.95 ± 0.37 | 6.22 ± 3.05 | 0.92 ± 0.07 | 2.23 ± 1.26 |
| CHJ04034 | 0.86 ± 0.45 | 3.06 ± 1.10 | 0.65 ± 0.14 | 1.16 ± 0.94 |
| CHJ04036 | 17.84 ± 3.62 | 15.5 ± 2.56 | 18.36 ± 1.10 | 3.67 ± 0.41 |
| CHJ04058 | 245.31 ± 2.40 | 101.71 ± 1.48 | 56.21 ± 0.55 | 53.96 ± 2.14 |
| CHJ04059 | 10.63 ± 3.37 | 3.26 ± 1.21 | 3.23 ± 0.49 | 3.92 ± 0.56 |
| CHJ04060 | — | — | — | — |
| CHJ04061 | 333.10 ± 2.7 | 143.47 ± 3.1 | 62.13 ± 4,21 | 97.14 ± 4.21 |
| CHJ04064 | 21.50 ± 3.65 | 17.05 ± 0.24 | 9.24 ± 2.65 | 3.55 ± 2.14 |
| CHJ04065 | 25.48 ± 2.11 | 27.07 ± 1.62 | 10.82 ± 1,79 | 3.14 ± 1.06 |
| CHJ04066 | 29.90 ± 2.45 | 77.07 ± 4.07 | 10.29 ± 1.40 | 2.50 ± 0.65 |
| CHJ04068 | 5.46 ± 1.76 | 4.21 ± 1.23 | 1.54 ± 1.34 | 0.52 ± 0.40 |
| CHJ04072 | 12.53 ± 2.44 | 9.62 ± 4.23 | 2.26 ± 0.37 | 5.21 ± 2.31 |
| CHJ04082 | 22.26 ± 1.98 | 28.54 ± 5.22 | 7.51 ± 2.62 | 2.82 ± 1.05 |
| CHJ04083 | 13.35 ± 2.02 | 10.36 ± 1.43 | 2.44 ± 1.03 | 1.23 ± 0.17 |
| CHJ04084 | 42.69 ± 3.06 | 96.38 ± 2.72 | 16.70 ± 2.48 | 7.54 ± 1.02 |
| CHJ04085 | 28.83 ± 5.12 | 49.22 ± 1.97 | 7.32 ± 1.80 | 1.94 ± 0.79 |
| CHJ04086 | — | — | 34.7 ± 3.42 | — |
| CHJ04089 | 27.78 ± 1.73 | 42.71 ± 2.61 | 15.03 ± 2.37 | 49.50 ± 3.54 |
| CHJ04090 | 35.01 ± 2.21 | 36.4 ± 2.17 | 11.70 ± 2.12 | 34.05 ± 2.59 |
| CHJ04091 | 11.05 ± 1.33 | 17.8 ± 3.11 | 4.01 ± 3.11 | 10.63 ± 3.20 |
| CHJ04092 | 30.16 ± 2.76 | 34.5 ± 2.70 | 11.23 ± 1.05 | 47.91 ± 3.43 |
| CHJ04093 | 20.12 ± 2.01 | 10.24 ± 1.69 | 2.60 ± 1.22 | 14.45 ± 2.14 |
| CHJ04094 | 18.40 ± 3.17 | 15.86 ± 2.11 | 2.05 ± 1.01 | 28.51 ± 4.42 |
| CHJ04097 | 24.38 ± 2.78 | 33.59 ± 2.47 | 14.85 ± 2.77 | 32.10 ± 3.39 |

-continued

| IC$_{50}$ value of target compound against cancer cell proliferation | | | | |
|---|---|---|---|---|
| | IC$_{50}$ (μM) | | | |
| Compound | A549 | SKOV3 | A375 | LOVO |
| CHJ04098 | 35.92 ± 2.09 | 47.40 ± 3.20 | 19.48 ± 2.15 | 29.80 ± 3.72 |
| CHJ04099 | 23.10 ± 2.58 | 37.39 ± 2.48 | 16.16 ± 2.11 | 38.24 ± 2.94 |
| CHJ05001 | 30.69 ± 3.12 | 40.12 ± 3.02 | 15.78 ± 1.73 | 49.10 ± 2.71 |
| CHJ05002 | 35.66 ± 2.71 | 42.96 ± 2.37 | 13.66 ± 2.06 | 33.10 ± 3.27 |
| CHJ05003 | 33.97 ± 2.11 | 35.11 ± 1.35 | 24.92 ± 1.93 | 52.49 ± 1.22 |
| cisplatin | 4.21 ± 1.31 | 1.91 ± 0.43 | 5.91 ± 1.64 | 2.64 ± 1.12 |

3. Experiment Result

It is found by observing the above experiment data that the majority of the target compounds perform well in inhibiting human lung cancer (A549), human ovarian cancer (SKOV3), human melanoma (A375) and human colon cancer (LOVO) cells. Moreover, it can be seen from the data that the compounds with tetramethyl piperidine on the right are usually more active than those with tetrahydropyrrole, diethylin or pyrrole on the right in fighting off cancer. When the length of chain on the hydrophobic side increases on the left of the compound (CHJ03011 and CHJ03012), the compound is still effective against cancer. Nonetheless, the anti-cancer activity of compound can be lowered prominently by introducing large polar compound to the aromatic ring on the left (CHJ04068 and CHJ04061). It is worth noting that the compound with 3 Br atoms as substitute on the aromatic ring on the left (CHJ04022 and CHJ04068) are the most active, as active as the cis-platinum in the control group.

What is claimed is:

1. A compound of general formula (I), or its pharmaceutically acceptable salt or its optical isomer, Formula (I)

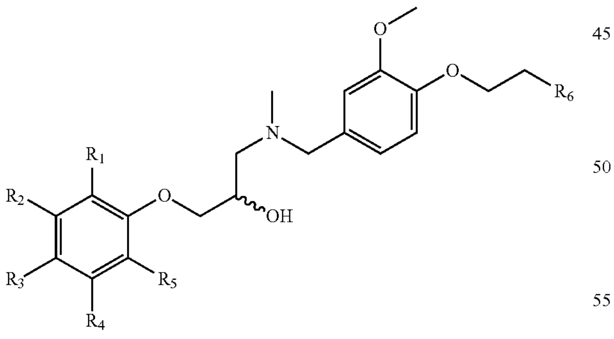

wherein, $R_1$ represents $—OC_2H_5$, —H, $—CH(CH_3)_2$, —Br, $—CF_3$, $—OCH_3$, —F, —Cl, or $—CH_3$;

$R_2$ represents —F, $—CF_3$, —Br, $—NHCOCH_3$, $—C_1$, —H, $—OCH_3$, or $—CH(CH_3)_2$;

$R_3$ represents —H, $—CH_3$, $—C_1$, —Br, $—NHCOCH_3$, $—C_3H_7$, —F, $—C_{14}H_{29}$, or $—OCH_3$;

$R_4$ represents —H, —Br, $—CF_3$, or —Cl;

$R_5$ represents —H, —Cl, —I, or —Br;

$R_6$ represents

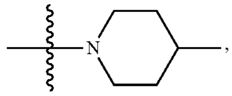 , 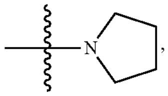 ,

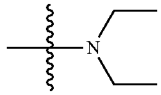 , or 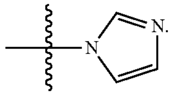

2. The compound described in claim 1 or its pharmaceutically acceptable salt or its optical isomer, wherein:

$R_1$ represents —H, $—CH(CH_3)_2$, —Br, or —Cl;

$R_2$ represents —F, —Br, —Cl, —H, $—CH(CH_3)_2$, or $—CF_3$;

$R_3$ represents —H, $—CH_3$, —Cl, —Br, or $—C_{14}H_{29}$;

$R_4$ represents —H, —Br, $—CF_3$, or —Cl;

$R_5$ represents —H, —Cl, —I, or —Br;

$R_6$ represents

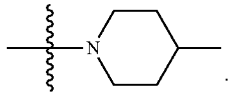 [SMILES: *N1CCC(C)CC1] .

3. The compound described in claim 2 or its pharmaceutically acceptable salt or its optical isomer, wherein:

$R_1$ represents —H; $R_2$ represents $—CF_3$; $R_3$ represents —Br; $R_4$ represents —H;

$R_5$ represents —H;

$R_6$ represents

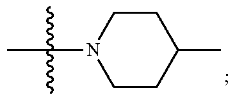 [SMILES: *N1CCC(C)CC1] ;

or $R_1$ represents —H; $R_2$ represents —H; $R_3$ represents $—C_{14}H_{29}$; $R_4$ represents —H; $R_5$ represents —H;

$R_6$ represents

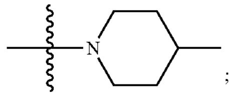 ;

or $R_1$ represents —H; $R_2$ represents —H; $R_3$ represents —Cl; $R_4$ represents —Br; $R_5$ represents —H;

$R_6$ represents

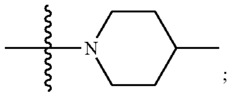

;

or $R_1$ represents —Br; $R_2$ represents —H; $R_3$ represents —Br; $R_4$ represents —H; $R_5$ represents —Br;

$R_6$ represents

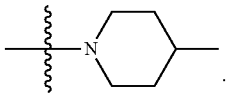 [SMILES: *N1CCC(C)CC1]

.

4. The compound described in claim 3 or its pharmaceutically acceptable salt or its optical isomer, wherein:

the described $R_1$ represents —H; $R_2$ represents —$CF_3$; $R_3$ represents —Br; $R_4$ represents —H;

$R_5$ represents —H;

$R_6$ represents

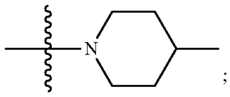 [SMILES: *N1CCC(C)CC1]

;

or $R_1$ represents —H; $R_2$ represents —H; $R_3$ represents —$C_{14}H_{29}$; $R_4$ represents —H; $R_5$ represents —H;

$R_6$ represents

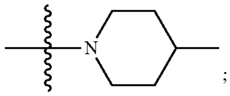

;

or $R_1$ represents —Br; $R_2$ represents —H; $R_3$ represents —Br; $R_4$ represents —H; $R_5$ represents —Br;

$R_6$ represents

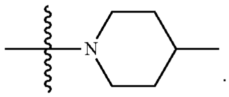

.

5. The compound described in claim 3 or its pharmaceutically acceptable salt or its optical isomer, wherein:

$R_1$ represents —H; $R_2$ represents —$CF_3$; $R_3$ represents —Br; $R_4$ represents —H; $R_5$ represents —H;

$R_6$ represents

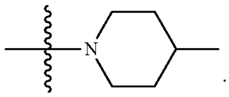 [SMILES: *N1CCC(C)CC1]

.

6. The compound described in claim 3 or its pharmaceutically acceptable salt or its optical isomer, wherein:

$R_1$ represents —Br; $R_2$ represents —H; $R_3$ represents —Br; $R_4$ represents —H;

$R_5$ represents —Br;

$R_6$ represents

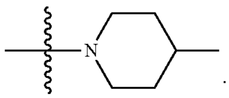 [SMILES: *N1CCC(C)CC1]

.

* * * * *